United States Patent
Barajas et al.

(10) Patent No.: US 12,053,183 B2
(45) Date of Patent: Aug. 6, 2024

(54) NEUROVASCULAR FLOW DIVERTER AND DELIVERY SYSTEMS

(71) Applicant: eLum Technologies, Inc., Fremont, CA (US)

(72) Inventors: Victor Barajas, Pleasanton, CA (US); Quang Tran, Atherton, CA (US); Yen Tu, Fremont, CA (US); Noelle Bagnall, Irvine, CA (US)

(73) Assignee: eLum Technologies, Inc., Fremont, CA (US)

( * ) Notice: Subject to any disclaimer, the term of this patent is extended or adjusted under 35 U.S.C. 154(b) by 0 days.

(21) Appl. No.: 18/112,963

(22) Filed: Feb. 22, 2023

(65) Prior Publication Data

US 2023/0263529 A1 Aug. 24, 2023

Related U.S. Application Data

(60) Provisional application No. 63/313,205, filed on Feb. 23, 2022.

(51) Int. Cl.
*A61B 17/12* (2006.01)
*A61B 90/00* (2016.01)

(52) U.S. Cl.
CPC .......... *A61B 17/12118* (2013.01); *A61B 17/12172* (2013.01); *A61B 2017/12054* (2013.01); *A61B 2090/3966* (2016.02)

(58) Field of Classification Search
CPC ........ A61B 17/12113; A61B 17/12118; A61B 17/12172; A61B 2017/12054; A61F 2/95; A61F 2002/9534
See application file for complete search history.

(56) References Cited

U.S. PATENT DOCUMENTS

| | | | |
|---|---|---|---|
| 5,746,769 A * | 5/1998 | Ton | A61B 17/12145 606/198 |
| 7,309,351 B2 | 12/2007 | Escamilla et al. | |
| 7,867,267 B2 | 1/2011 | Sullivan et al. | |
| 7,942,894 B2 | 5/2011 | West | |
| 8,172,891 B2 | 5/2012 | Shelso | |
| 8,211,141 B2 | 7/2012 | Davis, III et al. | |
| 8,241,345 B2 | 8/2012 | Phung | |

(Continued)

FOREIGN PATENT DOCUMENTS

| | | |
|---|---|---|
| CA | 3051087 A1 | 2/2020 |
| CN | 106214205 A | 12/2016 |

(Continued)

*Primary Examiner* — Diane D Yabut
*Assistant Examiner* — Christina C Lauer
(74) *Attorney, Agent, or Firm* — Kilpatrick Townsend & Stockton LLP

(57) ABSTRACT

Neurovascular flow diverter and delivery systems, and methods of using the same are disclosed herein. The systems can include an introducer sheath, a catheter, a deployable flow diverter that can be contained in the introducer sheath or in the catheter, a core wire, and one or several deployment features coupled to the core wire and engaging the flow diverter. The deployment features can include one or more of a pusher, one or several friction bumps, one or several deployment coils, a claw mechanism, a self-expanding element, a supporting coil, a tip coil, and/or an atraumatic tip. One or more of the deployment features can be radiopaque.

27 Claims, 24 Drawing Sheets

(56) References Cited

U.S. PATENT DOCUMENTS

| | | | |
|---|---|---|---|
| 8,317,859 B2 * | 11/2012 | Snow | A61F 2/95 623/6.12 |
| 8,523,887 B2 | 9/2013 | Grayzel et al. | |
| 8,636,760 B2 * | 1/2014 | Garcia | A61B 17/12109 606/200 |
| 8,784,466 B2 | 7/2014 | Igaki | |
| 8,986,362 B2 | 3/2015 | Snow et al. | |
| 9,017,365 B2 | 4/2015 | Lagodzki et al. | |
| 9,119,738 B2 | 9/2015 | Fish | |
| 9,119,948 B2 | 9/2015 | Lee et al. | |
| 9,192,499 B2 | 11/2015 | Gibbons, Jr. | |
| 9,326,876 B2 | 5/2016 | Acosta et al. | |
| 9,675,488 B2 | 6/2017 | Newell et al. | |
| 9,877,856 B2 | 1/2018 | Liang et al. | |
| 9,943,313 B2 | 4/2018 | Jones et al. | |
| 9,980,837 B2 | 5/2018 | Clerc | |
| 10,034,670 B2 | 7/2018 | Elgård et al. | |
| 10,064,747 B2 | 9/2018 | Berez et al. | |
| 10,315,011 B2 | 6/2019 | Vongphakdy et al. | |
| 10,426,612 B2 | 10/2019 | Costello | |
| 10,888,331 B2 | 1/2021 | Pederson et al. | |
| 10,898,356 B2 | 1/2021 | Longo et al. | |
| 10,932,933 B2 | 3/2021 | Bardsley et al. | |
| 10,945,867 B2 | 3/2021 | Nageswaran et al. | |
| 11,051,822 B2 | 7/2021 | Divino et al. | |
| 11,065,138 B2 | 7/2021 | Schreck et al. | |
| 11,071,637 B2 | 7/2021 | Dawson et al. | |
| 11,083,611 B2 | 8/2021 | Loganathan | |
| 11,129,738 B2 | 9/2021 | Gorochow | |
| 2002/0016597 A1 | 2/2002 | Dwyer et al. | |
| 2012/0226343 A1 | 9/2012 | Vo et al. | |
| 2014/0180387 A1 | 6/2014 | Khenansho et al. | |
| 2014/0277099 A1 * | 9/2014 | Wallace | A61B 17/12168 606/200 |
| 2014/0277360 A1 | 9/2014 | Girnary et al. | |
| 2016/0100965 A1 | 4/2016 | Nishigishi | |
| 2016/0302794 A1 | 10/2016 | Torp et al. | |
| 2018/0049892 A1 | 2/2018 | Henkes et al. | |
| 2019/0290458 A1 | 9/2019 | Slazas et al. | |
| 2019/0314179 A1 | 10/2019 | Nageswaran et al. | |
| 2019/0374228 A1 | 12/2019 | Wallace et al. | |
| 2020/0038209 A1 * | 2/2020 | Slazas | A61F 2/2436 |
| 2020/0368049 A1 | 11/2020 | Vong et al. | |
| 2021/0330332 A1 | 10/2021 | Chou et al. | |

FOREIGN PATENT DOCUMENTS

| | | |
|---|---|---|
| CN | 111528956 B | 6/2021 |
| EP | 3250157 A4 | 10/2018 |
| FR | 2939637 A1 | 6/2010 |
| WO | 2020134024 A1 | 7/2020 |

* cited by examiner

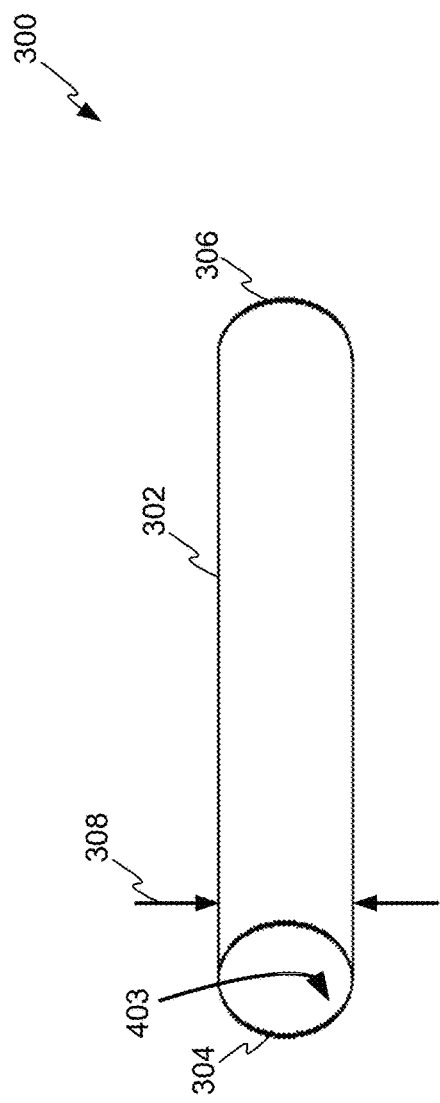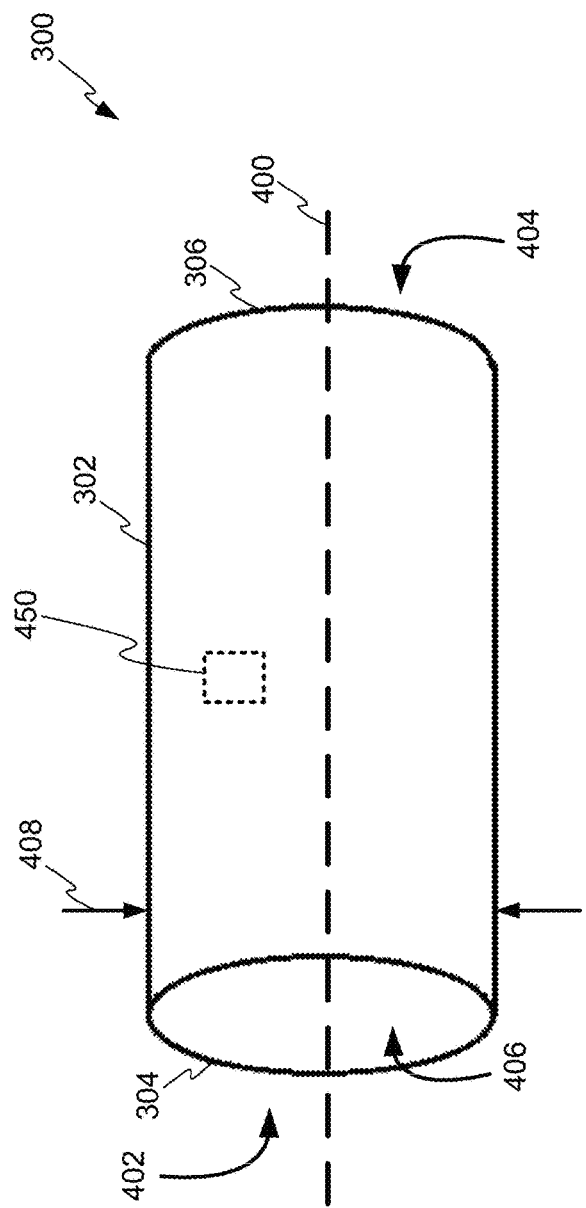

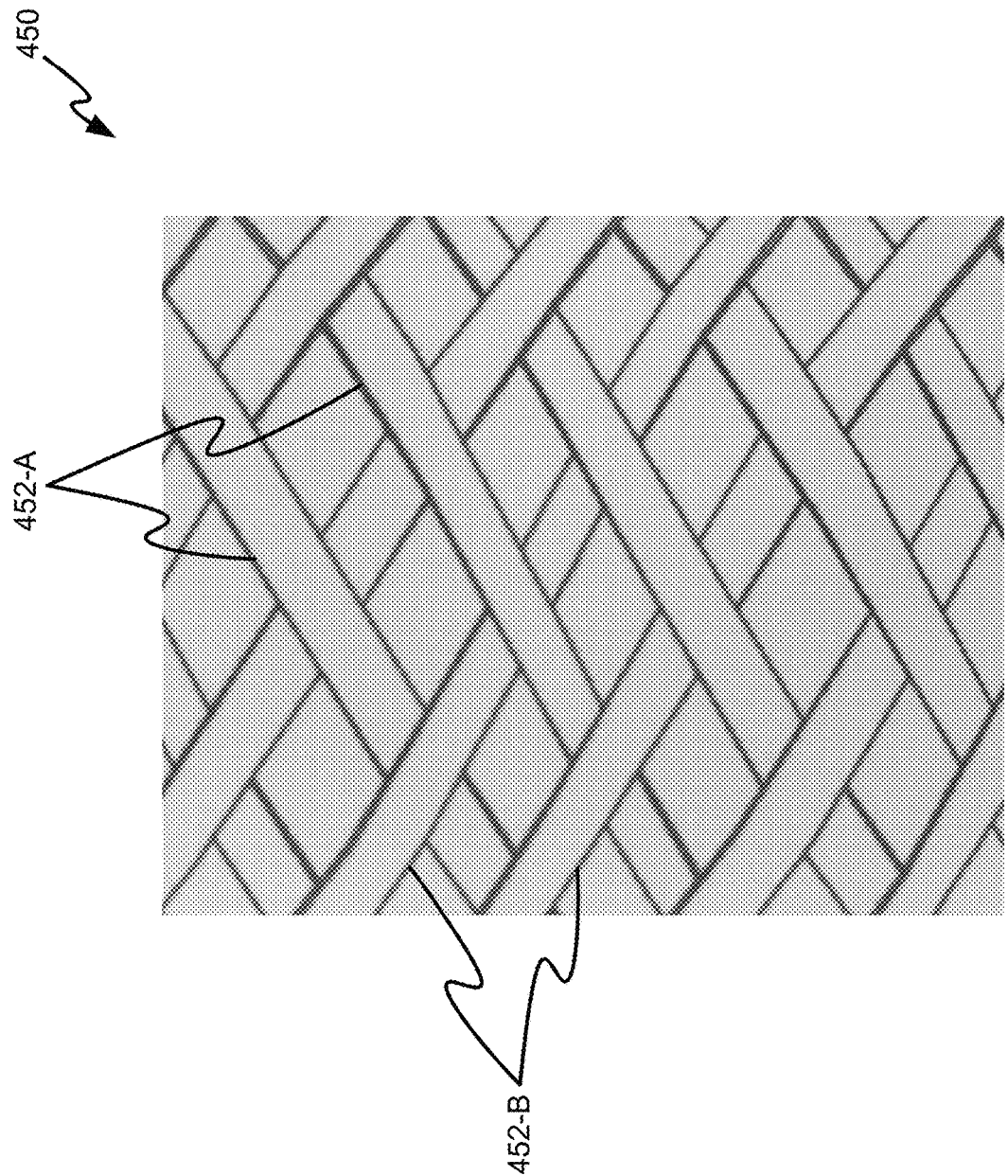

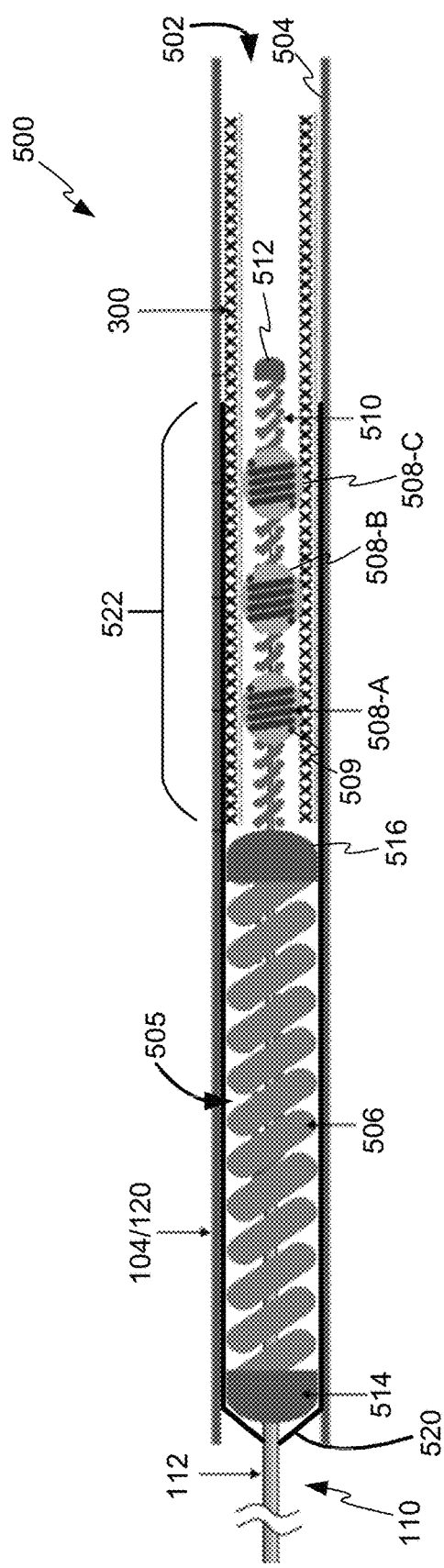
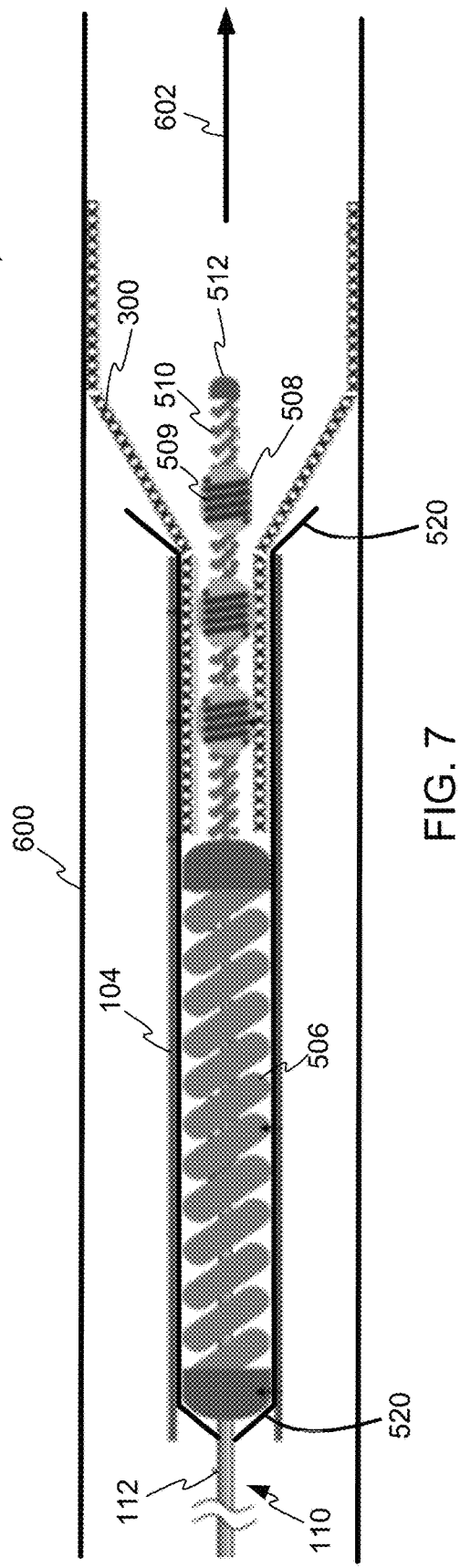
FIG. 6
FIG. 7

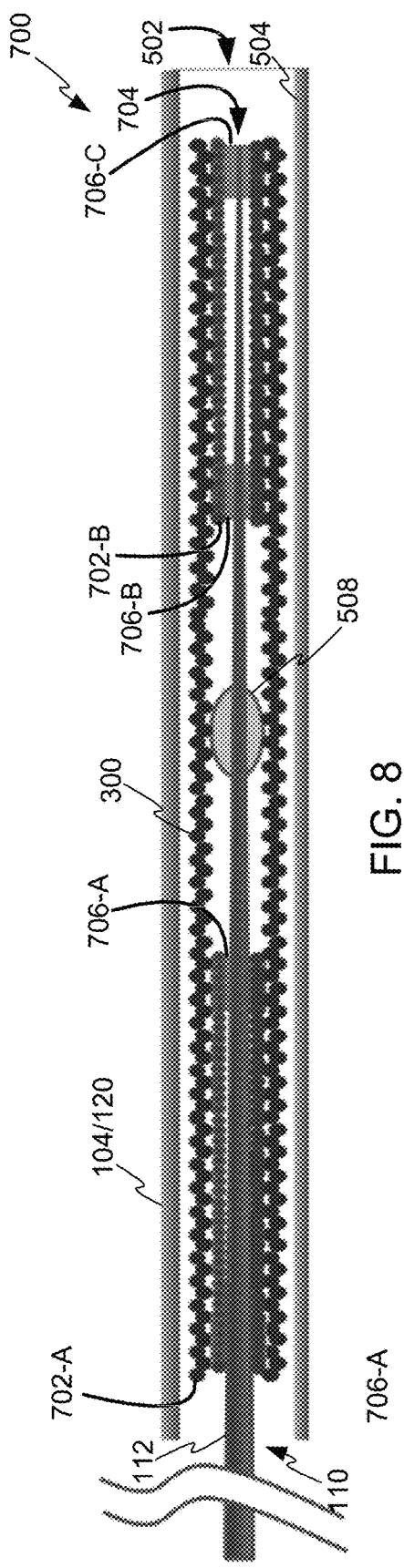
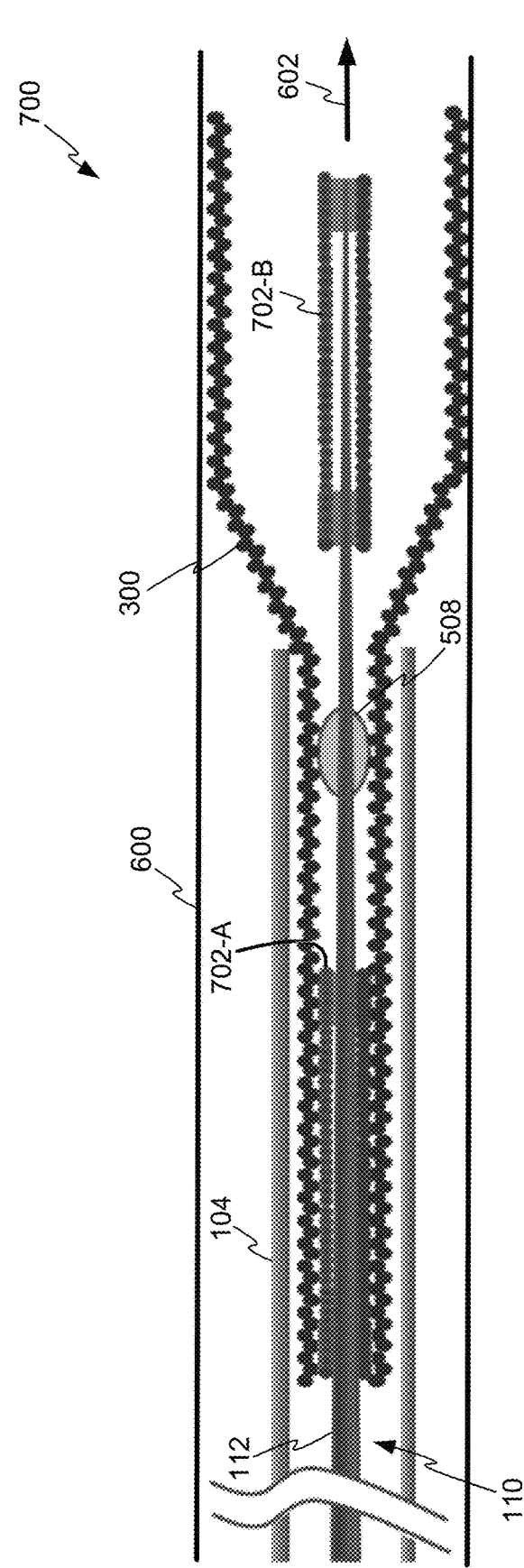

NEUROVASCULAR FLOW DIVERTER AND DELIVERY SYSTEMS

CROSS REFERENCE TO RELATED APPLICATION DATA

The present application claims the benefit under 35 USC § 119(e) of U.S. Provisional Appln. No. 63/313,205 filed Feb. 23, 2022; the full disclosure which is incorporated herein by reference in its entirety for all purposes.

BACKGROUND

An aneurysm is a bulge in a blood vessel caused by a weakness in the blood vessel wall which balloons and fills with blood. Aneurysms frequently occur where a blood vessel branches. As blood passes through the weakened blood vessel, the blood pressure causes a small area to bulge outwards like a balloon. While an aneurysm can form in any blood vessel in the body, they are most common in arteries that transport blood away from the heart, such as the aorta, or in the brain.

An aneurysm that forms inside the brain is referred to as an intracranial aneurysm or as a cerebral aneurysm. Brain aneurysms typically only cause noticeable symptoms if they burst, rupture, or leak. Rupture or bursting of a brain aneurysm creates a serious life-threatening condition known as a subarachnoid hemorrhage. Symptoms of such a hemorrhage include a sudden and agonizing headache, a stiff neck, sickness and vomiting, and pain when looking at light. A subarachnoid hemorrhage is life threatening and is a very serious medical emergency.

Because of the grave risks posed by such hemorrhage, prevention, early detection, and safe and efficacious treatment of cerebral aneurysms is desired. However, the complex nature of the neural vasculature, including the small diameter and tortuous anatomy of many of the blood vessels make such treatments difficult. In light of the risks posed by subarachnoid hemorrhage and the challenges in treating cerebral aneurysms, improved treatment systems and methods are desired.

BRIEF SUMMARY

The present relates to systems, devices, and methods for delivery of a flow diverter to a blood vessel, and specifically to a neurovascular blood vessel. The systems can include an introducer sheath, a catheter, a deployable flow diverter that can be contained in the introducer sheath or in the catheter, a core wire, and one or several deployment features coupled to the core wire and engaging the flow diverter. The core wire can be tapered. The deployment features can include a pusher, one or several friction bumps, one or several deployment coils, a claw mechanism, a self-expanding element, a supporting coil, a tip coil, and/or an atraumatic tip. These deployment features can be arranged in different combinations to facilitate deployment of the flow diverter.

In some embodiments, deployment features can include a pusher and at least one friction bump. Both the pusher and the at least one friction bump can be located on a tapered, distal portion of the core wire, with at least one friction bump located distal of the pusher. The pusher can be a pusher coil, and can have a distal end that abuttingly engages with a proximal end of the flow diverter. The pusher can completely deploy the flow diverter regardless whether the remaining deployment features are engaged with the flow diverter.

In some embodiments, at least one friction bump can be a plurality of friction bumps spread along a portion of the core wire extending distally beyond the pusher. Some or all of the plurality of friction bumps can include a radiopaque element, which radiopaque element can be a radiopaque wire coil.

Each of the friction bumps can engage with the flow diverter when the flow diverter is contained within the introducer sheath or the catheter. However, as the flow diverter is deployed from the catheter, the flow diverter expands and disengages from the friction bumps. Multiple spread out friction bumps increase a length over which the friction bumps contact the flow diverter, and increase control of the movement of the flow diverter. Specifically, as a friction bump only engages with the flow diverter when a portion of the flow diverter is between a friction bump and an interior wall of the catheter, multiple friction bumps spread distally from the pusher can increase the amount of the flow diverter that can be deployed while still maintaining control of the flow diverter.

In some embodiments, the deployment features include a single friction bump. This single friction bump can be distal of the pusher and can cover and extend beyond the distal end of the core wire. In some embodiments, the single friction bump abuts the pusher. By having the single friction bump directly contacting the pusher, the friction retains engagement with the flow diverter until the flow diverter is fully deployed. This increases flexibility of treatment by enabling retraction of the flow diverter at any state of partial deployment and as long as a portion of the flow diverter remains in the catheter. Further, embodiments with a single friction bump can decrease the length of the deployment features, and can terminate in a proximal portion of the flow diverter. This decreased length enables use of such an embodiment in treating smaller and further distal vasculature.

The deployment features can further include a support coil that extends along and around all or parts of the distal portion of the core wire. In some embodiments, the support coil can start proximal of the pusher, underneath the pusher, or distal of the pusher. The support coil can extend from its starting location to the pusher, to a position underneath the pusher, or to a location distal of the pusher. The support coil strengthens the core wire, and specifically strengthens the tapered, distal portion of the core wire. Specifically, the support coil strengthens the core wire so that the core wire does not buckle when subjected to a compressive load, such as when the core wire is used to deploy the flow diverter.

In some embodiments, deployment features can include a proximal delivery coil, a distal delivery coil, and a friction bump located intermediate between the proximal delivery coil and the distal delivery coil. Each of the proximal delivery coil and the distal delivery coil can extend along and around portions of the core wire, and specifically around portion of the distal portion of the core wire. Each of the proximal delivery coil and the distal delivery coil can strengthen the distal portion of the core wire to prevent buckling under compressive load, and each of the proximal delivery coil and the distal delivery coil engage with the flow diverter to deploy the flow diverter.

Similar to the friction bumps, the proximal delivery coil and the distal delivery coil engage with the flow diverter when a portion of the flow diverter is compressed between the respective one of the proximal delivery coil and/or the distal delivery coil and the interior wall of the catheter. In some embodiments, the proximal delivery coil can engage portions of the flow diverter including the proximal end of the flow diverter and the distal delivery coil can engage portions of the flow diverter including the distal end of the flow diverter. By engaging portions of the flow diverter including both the proximal end and the distal end of the flow diverter, this embodiment retains control over the deployment of the flow diverter as long as a portion of the flow diverter remains in the catheter, or in other words, until immediately before a last portion of the flow diverter is completely deployed from the catheter. This increases flexibility of treatment by enabling retraction of the flow diverter at any state of partial deployment and up until a last portion of the flow diverter is fully deployed from the catheter.

In some embodiments, the deployment features can include a pusher and a claw mechanism. Each of the pusher and the claw mechanism can be coupled to the core wire, with the claw mechanism coupled to the core wire at a location distal of the pusher. In some embodiments, the claw mechanism can be coupled to a distal end of the core wire.

The claw mechanism can include an elongate body and a grabber element. The elongated body and/or the grabber element can be rigid. The grabber body can radially extend from the elongated body and can include one or several engagement features that can engage with the flow diverter. These engagement features can be sized and shaped to insert into gaps in the flow diverter, and specifically to insert into gaps between strands of the flow diverter.

The claw mechanism can replace, for example, one or several friction bumps, and provides the benefit of engaging with the flow diverter without applying a radial force to the flow diverter. As the claw mechanism does not apply a radial force to the flow diverter, compressing the flow diverter against the interior wall of the catheter, the claw mechanism eases deployment of the flow diverter, which force presses the flow diverter into the catheter and makes it more difficult to deploy the flow diverter from the catheter.

In some embodiments, the deployment features can include an expanding element that can be either a self-expanding element or a controlled expanding element. The expanding element can be positioned within the catheter and within the inner diameter of a flow channel of the flow diverter, thereby compressing the flow diverter via the expanding element and the interior wall of the catheter. The expanding element can engage with the flow diverter when the expanding element pushes the flow diverter into the interior wall of the catheter. Thus, the expanding element can facilitate deployment of the flow diverter from the catheter and/or retraction of the flow diverter into the catheter.

When deployed, the expanding element can expand and can assist in expanding the deployed flow diverter. For example, the expanding element can generate greater forces biasing the expanding element to an expanded configuration than those generated by the flow diverter. Thus, when positioned inside of the flow channel of the flow diverter, these radial forces can bias the flow diverter towards greater and/or more full expansion against the vessel wall.

In some embodiments, upon exiting the catheter, the expanding element, which can be in the flow channel of a portion of the flow diverter, can expand. This expanding of the flow diverter can either be by self-expansion or by controlled expansion. The expansion of the flow diverter can bias the flow diverter at the location of the expanding element toward greater and/or full expansion against the vessel wall. The expanding element can then be moved through the flow diverter, for example, by distally advancing the expanding element through the flow diverter and/or by proximally retracting the expanding element through the flow diverter. Through the combination of the expansion of the expanding element and the movement of the expanding element through the deployed flow diverter, the flow diverter can be fully expanded and/or can be further expanded. This improved expansion of the flow diverter improves contact along the length of the flow diverter and between the flow diverter and the walls of the blood vessel, prevents "fish-mouthing" phenomenon, endoleaks, and minimizes fore-shortening of the flow diverter. The improved expansion of the flow diverter further results in an easier and more reliable deployment. Specifically, the improved expansion of the flow diverter eliminates the need for any post processing of a flow diverter, such as post processing including the use of balloon angioplasty. The easier and more reliable deployment arising from the improved expansion by the expanding element reduces procedure time and improves patient safety.

In addition to this, each of the expanding element and any friction bumps improve control of the flow diverter during the deployment of the flow diverter. This can include benefits of one or several friction bumps positioned proximal of the expanding element. Such proximal placement of one or several friction bumps can improve control of the flow diverter during deployment, and specifically can increase flexibility of treatment by enabling retraction of the flow diverter at more stages of deployment of the flow diverter.

Each of these embodiments of deployment features can be utilized in deploying a flow diverter to treat an aneurysm in a neurovascular blood vessel. Such a deployment can include advancing a catheter proximal to a treatment location in a neurovascular blood vessel, advancing a core wire through the catheter, and deploying the flow diverter from the catheter and into the neurovascular blood vessel to treat an aneurysm. The flow diverter can be deployed by advancing the deployment features via advancement of the core wire, which deployment features are engaged with the flow diverter.

The deployment of the flow diverter can be monitored via imaging. In some embodiments, this can include imaging of the catheter marker band, the flow diverter, for example, the flow diverter braid as it is deployed, and/or of one or several deployment features, such as one or several deployment features that are radiopaque and/or include a radiopaque element. Via this imaging, the positioning of the flow diverter can be monitored with respect to the distal end of the catheter. In some embodiments, the position of the flow diverter and/or the distal end of the catheter can be monitored with respect to the most proximal of the deployment features, which deployment feature enables retraction of the flow diverter.

When the flow diverter is to be repositioned, and if the most proximal of the deployment features that enables retraction of the flow diverter is wholly or partly in the lumen of the catheter and engaged with the flow diverter, then the flow diverter can be wholly or partially retracted into the catheter and can be repositioned. In some embodiments, deployment features that enable retraction of the flow diverter can include, for example, a friction bump such as the proximal most of one of the friction bumps, a deployment coil such as the proximal deployment coil, the expanding element, or the claw mechanism.

In some embodiments, the deployment features can improve control of the deployment of the flow diverter, which can beneficially improve the positioning of the flow diverter and the effectiveness of the flow diverter. This improved positioning can be of particular significance when multiple flow diverters are being deployed. This improved control over the deployment of the flow diverter can help ensure that multiple flow diverters have a desired position with respect to each other, including for example, that they sufficiently overlap each other to achieve the desired treatment effect.

In embodiments in which the deployment features include the expanding element, the further benefit of improved expansion of the flow diverter can be attained. This can beneficially improve the contact between the flow diverter and the wall of the blood vessel, thereby increasing the integrity of flow diverter performance. Such improved expansion can be of additional significance when deploying multiple flow diverters, as the use of the expanding element can facilitate complete expansion of the flow diverter, resulting in more consistent and uniform expansion between the multiple layers of flow diverters. Such improved consistency of expansion can improve the effectiveness of the flow diverters in preventing blood flow into one or several aneurysms.

The flow diverter can initially be contained within a lumen of the introducer sheath. The core wire can extend into this lumen of the introducer sheath and can engage with the flow diverter. The introducer sheath can be inserted into a lumen of the catheter, and the core wire can be advanced to push both the core wire and the flow diverter into the catheter. The catheter can be advanced to a position at, near, or beyond a treatment location, and the flow diverter can be deployed. In some embodiments, the catheter can be advanced to a position distal of the treatment location, and the flow diverter can be deployed. The deployment of the flow diverter can include the distal advancing of the core wire to distally push the flow diverter out of the catheter.

The deployment of the flow diverter can be monitored via imaging to ensure the proper placement of the flow diverter. If desired, the flow diverter can be wholly or partially retrieved into the catheter, and the catheter can be repositioned, if desired.

One or several flow diverters can be delivered to the treatment location. These flow diverters can be delivered to wholly or partially overlap. The delivery of multiple flow diverters to the treatment location can, for example, improve the diversion of flow, or can extend the length of the treated portion of the blood vessel.

One aspect of the present disclosure relates to a system for delivering a flow diverter into a neurovascular blood vessel to treat an aneurysm. The system includes an elongated tubular member having a proximal end and a distal end. The tubular member can include an interior wall defining a lumen. The system can include a flow diverter that can be or include a self-expanding member having a proximal end and a distal end. The flow diverter can define a flow channel, which flow channel can extend through the flow diverter such that the flow diverter is tubular. The flow diverter can be contained in a constrained configuration within the lumen of the tubular member. The system can include a deployment wire extending into the lumen of the tubular member and into the flow channel of the flow diverter. The deployment wire can have a proximal end, a distal end, and a distal portion having a taper. The deployment wire can include at least one deployment feature coupled to the flow diverter such that movement of the deployment wire relative to the tubular member moves the flow diverter relative to the tubular member and into the neurovascular blood vessel. At least one deployment feature can include a pusher extending along and around the distal portion of the deployment wire, at least one friction bump positioned along a portion of the deployment wire extending distally beyond the pusher, and a support coil extending along and around the distal portion of the deployment wire. The pusher can have a distal end that can engage with a proximal end of the flow diverter, and at least one friction bump can be inside of the flow channel of the flow diverter, and engaged with a portion of the flow diverter.

In some embodiments, at least one friction bump can be a plurality of friction bumps, which plurality of friction bumps can be equally spaced. In some embodiments, at least one friction bump can include a radiopaque element. In some embodiments, the radiopaque element can be a coil of wire.

In some embodiments, at least one friction bump can include a first friction bump, a second friction bump, and a third friction bump. In some embodiments, the first friction bump can be closer to the pusher than the second friction bump and the third friction bump. In some embodiments, the third friction bump is closer to the distal end of the deployment wire than the first friction bump and the second friction bump. In some embodiments, the support coil extends at least partially through the pusher and distally beyond the third friction bump and terminates to form an atraumatic tip.

In some embodiments, the pusher can be a pusher coil. In some embodiments, the pusher coil is soldered to the deployment wire. In some embodiments, the pusher coil comprises a radiopaque element.

In some embodiments, at least one friction bump comprises a single friction bump. In some embodiments, the single friction bump covers and extends distally beyond the distal end of the deployment wire. In some embodiments, the single friction bump abuts the pusher.

One aspect relates to a system for delivering a flow diverter into a neurovascular blood vessel to treat an aneurysm. The system can include an elongated tubular member having a proximal end and a distal end. In some embodiments, the tubular member can include an interior wall defining a lumen. The system can include a flow diverter that can be a self-expanding member having a proximal end and a distal end. In some embodiments, the flow diverter can define a flow channel, which flow channel can extend through the flow diverter. In some embodiments, the flow diverter is contained within the lumen of the tubular member in a constrained configuration. The system can include a deployment wire extending into the lumen of the tubular member and into the flow channel of the flow diverter. In some embodiments, the deployment wire can have a proximal end, a distal end, and a distal portion having a taper. In some embodiments, the deployment wire can include at least one deployment feature coupled to the flow diverter, such that movement of the deployment wire relative to the tubular member moves the flow diverter relative to the tubular member and into a neurovascular blood vessel. In some embodiments, at least one deployment feature can include a proximal delivery coil, a distal delivery coil extending to the distal end of the deployment wire, and at least one friction bump located between the proximal delivery coil and the distal delivery coil. The proximal delivery coil can extend along and around the distal portion of the deployment wire and can engage with a proximal portion of the flow diverter inside the flow channel. The distal delivery coil can extend along and around the distal portion of the deployment wire and can engage with a distal portion of the flow diverter inside the flow channel. At least one friction bump can be located inside of the flow channel of the flow diverter and engaged with an intermediate portion of the flow diverter.

In some embodiments, at least one of the friction bumps can include a radiopaque element. In some embodiments, each of the proximal delivery coil and the distal delivery coil comprises a wire winding.

In some embodiments, each of the proximal delivery coil and the distal delivery coil are coupled to the deployment wire via at least one spacer. In some embodiments, a distal end of the proximal delivery coil is coupled to the deployment wire via a first spacer, a proximal end of the distal delivery coil is coupled to the deployment wire via a second spacer, and the distal end of the distal delivery coil is coupled to the deployment wire via a third spacer. In some embodiments, a height of each of the first spacer, the second spacer, and the third spacer is such that the proximal delivery coil and the distal delivery coil have the same diameter. In some embodiments, a height of each of the first spacer, the second spacer, and the third spacer counteracts the taper of the distal portion of the deployment wire.

In some embodiments, at least one deployment features further includes a pusher coil extending along and around a portion of the deployment wire, which pusher coil is proximal of the proximal delivery coil. In some embodiments, at least one deployment feature further includes a support coil extending along and around the distal portion of the deployment wire. In some embodiments, at least one of the proximal delivery coils and the distal delivery coil is radiopaque.

One aspect relates to a system for delivering a flow diverter into a neurovascular blood vessel to treat an aneurysm. The system includes an elongated tubular member having a proximal end and a distal end. The tubular member can include an interior wall defining a lumen. The system can include a flow diverter including a self-expanding member having a proximal end and a distal end. The flow diverter can define a flow channel extending there through. In some embodiments, the flow diverter can be contained within the lumen of the tubular member in a constrained configuration. The system can include a core wire extending into the lumen of the tubular member and into the flow channel of the flow diverter. The core wire can have a proximal end, a distal end, and a distal portion having a taper. The system can include a pusher extending around part of the distal portion of the core wire, which pusher can have a distal end engaged with a proximal end of the flow diverter. In some embodiments, the core wire distally protrudes past the pusher. The system can include a claw mechanism coupled to the distal end of the core wire. The claw mechanism can include a grabber element engaged with the flow diverter. In some embodiments, the pusher and the claw mechanism are engaged with a portion of the flow diverter inside the flow channel such that a movement of the core wire relative to the elongated tubular member moves the flow diverter relative to the tubular member to a deployed configuration within a neurovascular blood vessel.

In some embodiments, the claw mechanism includes an elongated body have a proximal end and a distal end. In some embodiments, the proximal end of the elongate body can be coupled to the distal end of the core wire. In some embodiments, the grabber element is at the distal end of the elongate body of the claw mechanism. In some embodiments, the elongate body of the claw mechanism is rigid.

In some embodiments, the proximal end of the elongated body of the claw mechanism is coupled to distal end of the core wire at a junction. In some embodiments, the junction is flexible. In some embodiments, the system includes a support coil extending along and around at least part of the distal portion of the deployment wire. In some embodiments, the support coil extends across the junction and over a portion of the elongate body of the claw mechanism.

In some embodiments, the system includes a flexible tip coil extending distally from the distal end of the elongate body of the claw mechanism. In some embodiments, the tip coil distally terminates with an atraumatic tip. In some embodiments, the system includes a friction bump. In some embodiments, the friction bump is radiopaque. In some embodiments, the friction bump is located at the junction. In some embodiments, at least a portion of the claw mechanism is radiopaque. In some embodiments, the grabber element radially extends from the elongate body of the claw mechanism. In some embodiments, the pusher can be a pusher coil.

One aspect relates to a system for delivering a flow diverter into a neurovascular blood vessel to treat an aneurysm. The system includes an elongated tubular member having a proximal end and a distal end, the tubular member including an interior wall defining a lumen. The system can include a core wire extending at least partially through the lumen of the tubular member, the core wire having a proximal end, a distal end, and a distal portion having a taper. In some embodiments, the distal portion of the core wire can extend from an intermediate portion of the core wire to a distal end of the core wire. The system can include a self-expanding element that can include a first end coupled to the distal end of the core wire and extending distally to a second end. The system can include a first friction bump located at one of the first end and the second end of the self-expanding element and a support coil extending along and around at least the distal end of the core wire. The system can include a flow diverter, which can be an expandable member. The expandable member of the flow diverter can define a flow channel, which flow channel can extend through the flow diverter. In some embodiments, the flow diverter can be positioned in the lumen of the tubular member and circumferentially between the wall of the tubular member and the self-expanding element. In some embodiments, the self-expanding element is disposed within the flow channel and can move the flow diverter relative to the tubular member and into a neurovascular blood vessel while the self-expanding element is deployed out of the tubular member to expand the flow diverter.

In some embodiments, the self-expanding element can be a stent. In some embodiments, the stent can be laser cut. In some embodiments, the flow diverter can be a braided, expandable member. In some embodiments, the flow diverter can be self-expanding.

In some embodiments, the first friction bump can be a radiopaque element. In some embodiments, the radiopaque element can be a coil of wire.

In some embodiments, the system includes a second friction bump located at the other of the first end and the second end of the self-expanding element. In some embodiments, the system can include a flexible tip coil extending distally from the second end of the self-expanding element. In some embodiments, the tip coil distally terminates with an atraumatic tip. In some embodiments, the tubular member can be an introducer sheath. In some embodiments, the tubular member can be a catheter.

One aspect relates to a method for delivering a flow diverter into a neurovascular blood vessel to treat an aneurysm. The method includes advancing a microcatheter proximal to a treatment location within a neurovascular blood vessel, advancing a core wire through the microcatheter, and deploying the flow diverter from the microcatheter and into the neurovascular blood vessel to treat an aneurysm by advancing the pusher and the at least on friction bump via advancement of the core wire. The core wire can have a proximal end, a distal end, and distal portion having a taper. In some embodiments, the distal end of the core wire can extend into a flow channel of a flow diverter. In some embodiments, the flow diverter can be contained in a constrained configuration within the microcatheter. In some embodiments, the core wire can be coupled to the flow diverter via at least one deployment feature. In some embodiments, at least one deployment feature can include a pusher extending along and around a distal portion of the core wire. In some embodiments, the pusher can have a distal end that can engage with a proximal end of the flow diverter. At least one deployment feature can include at least one friction bump along a portion of the core wire extending distally beyond the pusher. In some embodiments, the at least one friction bump is inside the flow channel of the flow diverter and engaged with a portion of the flow diverter.

In some embodiments, at least one friction bump comprises a plurality of friction bumps distributed along the portion of the core wire, which plurality of friction bumps are equally spaced. In some embodiments, at least one of the plurality of friction bumps can include a radiopaque element. In some embodiments, each of the plurality of friction bumps can facilitate retraction of the flow diverter into the microcatheter when the flow diverter is partially deployed from the microcatheter and can facilitate deployment of the flow diverter from the microcatheter. In some embodiments, the plurality of friction bumps can include a first friction bump, a second friction bump, and a third friction bump. In some embodiments, the first friction bump is closer to the pusher than the second friction bump and the third friction bump, and the third friction bump is closer to the distal end of the core wire than the first friction bump and the second friction bump.

In some embodiments, at least one deployment feature can include a support coil. In some embodiments, the support coil can extend along and around the distal portion of the core wire. In some embodiments, the support coil extends at least partially through the pusher and distally beyond the third friction bump. In some embodiments, the support coil extending distally beyond the third friction bump terminates to form an atraumatic tip.

In some embodiments, at least one friction bump can be a single friction bump. In some embodiments, the single friction bump covers the distal end of the core wire and abuts the pusher. In some embodiments, the pusher coil and the single friction bump together form a shorted delivery system and/or shortened deployment features. The shortened delivery system can terminate in a proximal portion of the flow diverter. In some embodiments, termination of the shortened delivery system in the proximal portion of the flow diverter can facilitate deployment and enable treatment of smaller blood vessels. In some embodiments, the single friction bump remains engages with the flow diverter until the flow diverter exits the microcatheter. In other words, as long as a portion of the flow diverter remains within the microcatheter, the single friction bump engages with the flow diverter. In some embodiments, the flow diverter is retractable via the single friction bump as long as a portion of the flow diverter remains in the catheter, or in other words, until immediately before a last portion of the flow diverter is fully deployed from the microcatheter.

In some embodiments, the method includes retracting the flow diverter into the microcatheter, adjusting positioning of the microcatheter with respect to the treatment location, and advancing the core wire through the microcatheter to fully deploy the flow diverter from the microcatheter. In some embodiments, at least one of the pusher and the at least one friction bump is radiopaque. In some embodiments, the method further includes imaging at least one of the pusher and the at least one friction bump to determine a position of the flow diverter in the neurovascular blood vessel and a position of the pusher and/or the at least one friction bump with respect to the microcatheter. In some embodiments, the at least one of the pusher and the at least one of the friction bump that are imaged can be radiopaque. In some embodiments, the flow diverter is retracted into the microcatheter when at least one of the at least one friction bump has not exited the microcatheter. In some embodiments, the positioning of the microcatheter is adjusted with respect to the treatment location based on the imaging.

In some embodiments, the method includes loading the flow diverter into the microcatheter. In some embodiments, loading the flow diverter into the microcatheter includes inserting an introducer sheath containing the flow diverter through an access device into the microcatheter, and advancing the core wire through the introducer sheath to advance the flow diverter from the introducer sheath into the microcatheter.

One aspect relates to a method for delivering a flow diverter into a neurovascular blood vessel to treat an aneurysm. The method includes advancing a microcatheter to a position at, near, or beyond, such as distal to, a treatment location within a neurovascular blood vessel, advancing a core wire through the microcatheter, and deploying the flow diverter from the microcatheter and into the neurovascular blood vessel to treat an aneurysm by advancing the proximal and distal delivery coils via the coil wire. In some embodiments, the core wire can have a proximal end, a distal end, and distal portion having a taper. The core wire can be coupled to a flow diverter via at least one deployment feature, which at least one deployment feature can include a proximal delivery coil, a distal delivery coil extending to the distal end of the core wire, and at least one friction bump located between the proximal delivery coil and the distal delivery coil. The flow diverter can be contained in a constrained configuration within the microcatheter. The proximal delivery coil can extend along and around the distal portion of the deployment wire and can engage with a proximal portion of the flow diverter inside the flow channel. The distal delivery coil can extend along and around the distal portion of the deployment wire and can engage with a distal portion of the flow diverter inside the flow channel. The at least one friction bump can be located inside of the flow channel of the flow diverter and engaged with an intermediate portion of the flow diverter.

In some embodiments, the method further includes retracting the core wire to at least partially retract the flow diverter into the microcatheter, and advancing the core wire through the microcatheter to fully deploy the flow diverter from the microcatheter. In some embodiments, the flow diverter can be retracted, also referred to herein as retrieved, and deployed at the same location or at different locations. In some embodiments, the method further includes adjusting positioning of the microcatheter with respect to the treatment location. In some embodiments, at least one of the proximal delivery coil, the distal delivery coil, and the at least one friction bump is radiopaque. In some embodiments, the method further includes imaging the at least one of the proximal delivery coil, the distal delivery coil, and the at least one friction bump to determine a position of the flow diverter in the neurovascular blood vessel and a position of the at least one of the proximal delivery coil, the distal delivery coil, and the at least one friction bump with respect to the microcatheter. In some embodiments, the at least one of the proximal delivery coil, the distal delivery coil, and the at least one friction bump that is imaged can be radiopaque. In some embodiments, the flow diverter is retracted into the microcatheter when the at least one of the proximal delivery coil, the distal delivery coil, and the at least one friction bump has not exited the microcatheter. In some embodiments, the positioning of the microcatheter is adjusted with respect to the treatment location based on the imaging.

In some embodiments, the method includes loading the flow diverter into the microcatheter. In some embodiments, loading the flow diverter into the microcatheter includes inserting an introducer sheath containing the flow diverter through a rotating hemostatic valve into the microcatheter, and advancing the core wire through the introducer sheath to advance the flow diverter from the introducer sheath into the microcatheter.

One aspect relates to a method for delivering a flow diverter into a neurovascular blood vessel to treat an aneurysm. The method includes advancing a microcatheter to a position at, near, or beyond, including distal to, a treatment location within a neurovascular blood vessel, advancing a core wire through the microcatheter, and deploying the flow diverter from the microcatheter and into the neurovascular blood vessel to treat an aneurysm by advancing the pusher and the claw mechanism via the core wire. In some embodiments, the core wire can have a proximal end, a distal end, and distal portion having a taper. In some embodiments, the distal end of the core wire extends into a flow channel of a flow diverter. The flow diverter can be contained in a constrained configuration within the microcatheter. The core wire can couple to the flow diverter via at least one deployment feature. In some embodiments, the at least one deployment feature can include a pusher extending around part of the distal portion of the core wire. In some embodiments, the pusher can have a distal end engaged with a proximal end of the flow diverter. In some embodiments, the core wire distally protrudes past the pusher. The at least one deployment feature can include a claw mechanism coupled to the distal end of the core wire. In some embodiments, the claw mechanism can include a grabber element engaged with the flow diverter. In some embodiments, the pusher and the claw mechanism are engaged with the flow diverter such that a movement of the core wire relative to the microcatheter moves the flow diverter relative to the microcatheter.

In some embodiments, the claw mechanism can have an elongate body have a proximal end and a distal end. In some embodiments, the proximal end of the elongate body of the claw mechanism can be coupled to the distal end of the core wire. In some embodiments, the elongate body of the claw mechanism can be rigid. In some embodiments, the grabber element is at the distal end of the elongate body of the claw mechanism. In some embodiments, the proximal end of the elongate body of the claw mechanism is coupled to distal end of the core wire at a junction. In some embodiments, the at least one deployment feature further includes a support coil extending along and around at least part of the distal portion of the core wire and across the junction and over a portion of the elongate body. In some embodiments, the at least one deployment feature further includes a flexible tip coil extending distally from the distal end of the elongate body of the claw mechanism. In some embodiments, the tip coil distally terminates with an atraumatic tip.

In some embodiments, the method includes retracting the core wire to at least partially retract the flow diverter into the microcatheter, adjusting positioning of the microcatheter with respect to the treatment location, and advancing the core wire through the microcatheter to fully deploy the flow diverter from the microcatheter. In some embodiments, at least a portion of the claw mechanism is radiopaque. In some embodiments, the method further includes imaging the radiopaque portion of the claw mechanism to determine a position of the flow diverter in the neurovascular blood vessel and a position of the claw mechanism with respect to the microcatheter. In some embodiments, the flow diverter is retracted into the microcatheter when the claw mechanism has not exited the microcatheter. In some embodiments, the positioning of the microcatheter is adjusted with respect to the treatment location based on the imaging.

In some embodiments, the method includes loading the flow diverter into the microcatheter. In some embodiments, loading the flow diverter into the microcatheter includes inserting an introducer sheath containing the flow diverter through an access device into the microcatheter, and advancing the core wire through the introducer sheath to advance the flow diverter from the introducer sheath into the microcatheter.

One aspect relates to a method for delivering a flow diverter into a neurovascular blood vessel to treat an aneurysm. The method includes advancing a microcatheter to a position at, near, or beyond, including distal to, a treatment location within a neurovascular blood vessel, advancing a self-expanding element coupled to a distal end of a core wire through the microcatheter to unsheath a flow diverter from the microcatheter, deploying the self-expanding element out of the microcatheter and into the neurovascular blood vessel to treat an aneurysm by advancing the self-expanding element via the core wire, and pushing the self-expanding element through the delivered flow diverter to expand the flow diverter. In some embodiments, the flow diverter is contained in a constrained configuration within the microcatheter. In some embodiments, the self-expanding element is expanded when pushed through the delivered flow diverter to expand the flow diverter.

In some embodiments, pushing the self-expanding element through the flow diverter to expand the flow diverter includes distally pushing the expanded self-expanding element through the flow diverter. In some embodiments, the method includes proximally retracting the self-expanding element through the flow diverter and into the microcatheter. In some embodiments, the self-expanding element can be a stent. In some embodiments, the flow diverter can be a tubular braided member.

In some embodiments, the self-expanding element includes a first end coupled to the distal end of the core wire and distally extending to a second end. In some embodiments, the self-expanding element can include a first friction bump located at the first end of the self-expanding element and a second friction bump located at the second end of the self-expanding element.

In some embodiments, the microcatheter includes an interior wall defining a lumen. In some embodiments, the flow diverter defines a diverter lumen. In some embodiments, the self-expanding element is at least partially in the diverter lumen. In some embodiments, the flow diverter is positioned in the lumen of the microcatheter and circumferentially between the interior wall of the microcatheter and the self-expanding element.

In some embodiments, the method includes, before deploying the self-expanding element out of the microcatheter, retracting the self-expanding element coupled to the distal end of the core wire to at least partially retract the flow diverter into the microcatheter, and before deploying the self-expanding element out of the microcatheter, adjusting positioning of the microcatheter with respect to the treatment location. In some embodiments, at least the self-expanding element is radiopaque. In some embodiments, the method further includes imaging the radiopaque self-expanding element to determine a position of the flow diverter in the neurovascular blood vessel and a position of the self-expanding element with respect to the microcatheter. In some embodiments, the flow diverter is retracted into the microcatheter when the self-expanding element has not exited the microcatheter. In some embodiments, the positioning of the microcatheter is adjusted with respect to the treatment location based on the imaging.

In some embodiments, the method includes loading the flow diverter into the microcatheter. In some embodiments, loading the flow diverter into the microcatheter includes inserting an introducer sheath containing the flow diverter through a rotating hemostatic valve into the microcatheter, and advancing the core wire through the introducer sheath to advance the flow diverter from the introducer sheath into the microcatheter.

In some embodiments, the self-expanding element intermittently contacts an inner wall of the flow diverter to thereby expand the flow diverter. In some embodiments, the self-expanding element intimately contacts an inner wall of the flow diverter to thereby expand the flow diverter.

Further areas of applicability of the present disclosure will become apparent from the detailed description provided hereinafter. It should be understood that the detailed description and specific examples, while indicating various embodiments, are intended for purposes of illustration only and are not intended to necessarily limit the scope of the disclosure.

BRIEF DESCRIPTION OF THE DRAWINGS

FIG. 3 is a depiction of the flow diverter in a constrained delivery state.
FIG. 4 is a depiction of the flow diverter in an expanded deployed state.
FIG. 5 is a close-up view of a braid of a flow diverter.
FIG. 6 is an illustration of a first flow diverter delivery system.
FIG. 7 is a depiction of the first delivery system in a partially deployed configuration.
FIG. 8 is a depiction of a second delivery system.
FIG. 9 is a depiction of the second delivery system in a partially deployed configuration.

DETAILED DESCRIPTION

The present relates to flow diverters, flow diverter delivery systems, and methods of delivering a flow diverter. A flow diverter is a device that can be placed within vasculature to divert flow away from portions of the vasculature covered by the flow diverter. As used herein, a flow diverter can be any device that is positionable within a patient's blood vessel and can divert a portion of the blood flow through that blood vessel. In some embodiments, a flow diverter can be an endovascular prosthesis used in treating intracranial aneurysms. A flow diverter can include, for example, a stent such as a laser cut stent, a braided member, or the like. In some embodiments, a flow diverter can comprise a braided member comprising a plurality of braided wires, which wires can be, for example, cobalt-chrome, Nitinol, or the like.

A flow diverter can be used to treat an intracranial aneurysm including, for example, saccular aneurysm and particularly an unerupted saccular aneurysm, or a fusiform shape or circumferential aneurysm. A flow diverter can be placed in a blood vessel to extend across and cover an aneurysm. The flow diverter can divert blood flow away from the aneurysm, thereby reducing blood flow in the aneurysm. Having reduced blood flow, over time, the aneurysm can close and heal.

While simple in principle, the reality of accurately placing a flow diverter in frequently small and tortuous vasculature of the brain can be very complicated. Accordingly, devices are desired that have high flexibility to enable the navigation of this vasculature. Further, such devices should be able to accurately position a flow diverter within a blood vessel. Accurately positioning of a flow diverter can include adjusting the position of the flow diverter, and in some embodiments can include, positioning multiple flow diverters to wholly or partially overlap. The use of multiple partial or wholly overlapping flow diverters can be of particular benefit in dealing with multiple closely spaced aneurysms or with a larger aneurysm. In some embodiments, multiple flow diverters can be positioned to wholly or partially overlap to further reduce blood flow to an aneurysm.

Embodiments disclosed herein provide several beneficial improvements. These include, for example, a decrease in the size of the system. This decrease in size of the system enables the accessing and treating of smaller blood vessels. This increases range of treatable aneurysms, and thus improves patient outcomes. Further, embodiments disclosed herein improve flexibility of the system, thereby also increasing the range of treatable aneurysms.

Figure 1:
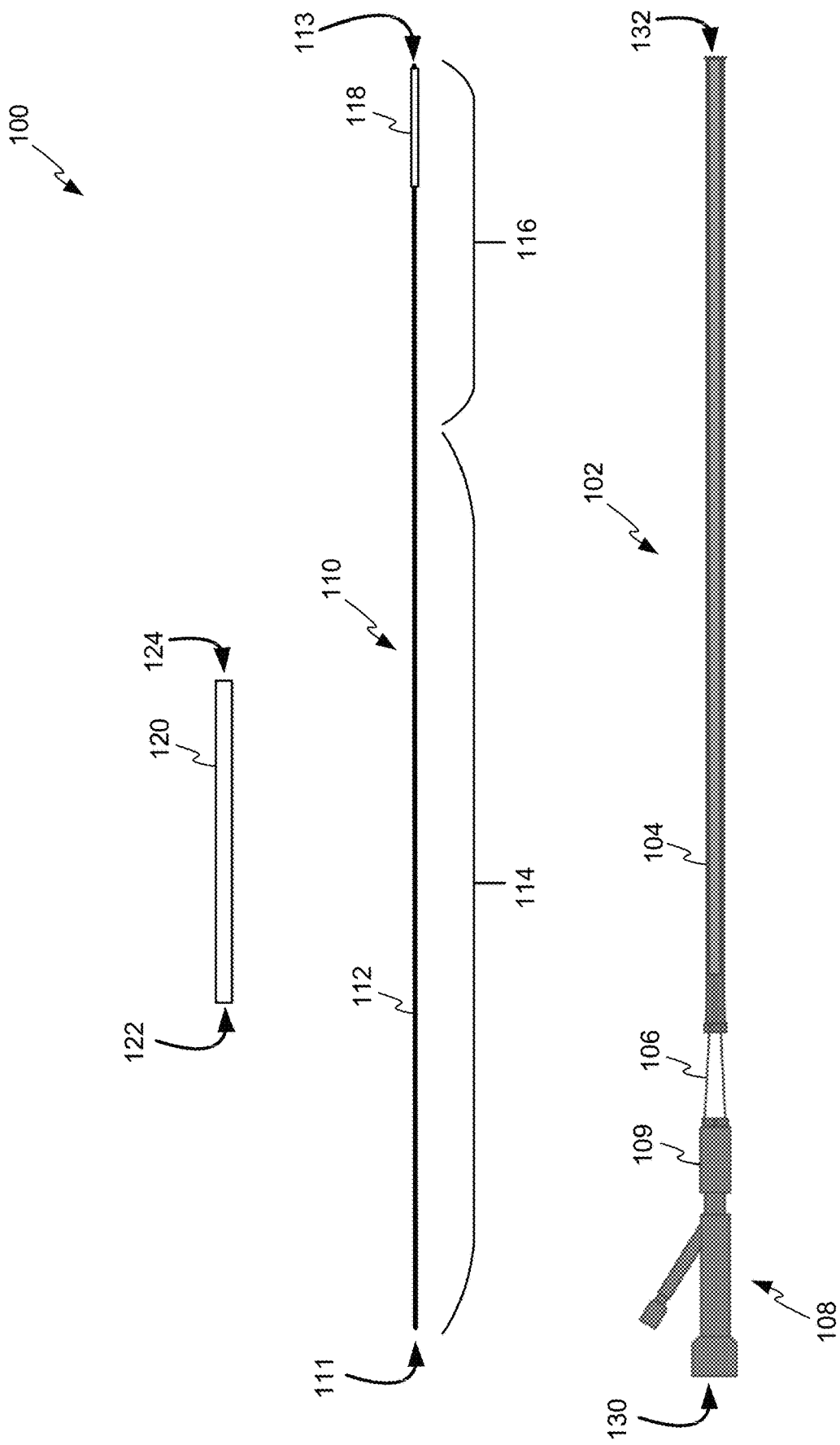
FIG. 1 is a depiction of one embodiment of a system for placement of a flow diverter.

With reference now to FIG. 1 a depiction of one embodiment of a system 100 for placement of a flow diverter is shown. The system 100 can include a catheter system 102. The catheter system 102 can be configured to provide access to the patient's vasculature, and specifically to the patient's neurovasculature. In some embodiments, the catheter system 102 can be configured for insertion into the patient's vasculature at an access point, and for navigating through the patient's vasculature to a location at which the flow diverter is to be delivered.

The catheter system 102 can comprise a proximal end 130 and a distal end 132. The catheter system 102 can comprise an elongate catheter 104 defining a lumen extending through all or portions of the catheter 104. Accordingly, in some embodiments, the catheter system 102 can comprise an elongate tubular member defining a lumen, and specifically the elongate tubular member comprising an interior wall defining a lumen. The catheter 104 can comprises a variety of sizes, materials, and/or manufactures. In some embodiments, the catheter 104 can be flexible and can comprise a biocompatible material. The catheter 104 can comprise, for example, an elongate tubular member can have a diameter of, for example, 0.005 inches, 0.01 inches, 0.017 inches, 0.02 inches, 0.021 inches, 0.027 inches, 0.03 inches, or any other or intermediate diameter.

The catheter 104, which can include a catheter hub 106 can be coupled to an access device. The access device 108 can be a valve such as, for example, a rotating hemostasis valve (RHV) 109. The access device 108 can be a hemostasis valve that can be configured to provide selectable and/or controllable access to the lumen of the catheter 104. In some embodiments, the access device 108 can be configured to minimize blood loss while the catheter 104 is being used. The access device 108 can be sized for use in connection with the catheter 104.

The system 100 for placement of the flow diverter can include a deployment wire 110 comprising a proximal end 111 and a distal end 113. The deployment wire 110 can be configured to facilitate and/or control the advance of the flow diverter into and/or through the catheter system 102, and specifically into and/or through the lumen of the catheter 104. In some embodiments, the proximal end 111 of the deployment wire 110 is configured to be controlled to control the advance of the flow diverter into and/or through the catheter system 102, and the distal end 113 can be configured to be coupled to and/or to interact with the flow diverter to cause the flow diverter to advance into and/or through the catheter system 102.

The deployment wire 110 can comprise a core wire 112. The core wire 112 can comprise an elongate wire that can be flexible to enable navigation vasculature. In some embodiments, the core wire 112 can comprise a unibody reinforced delivery wire. The core wire 112 can comprise a variety of shapes and sizes and can be made from a variety of materials. The core wire 112 can comprise a biocompatible wire that can be, for example, a Nitinol wire.

The core wire 112 can, comprise a proximal portion 114 and a distal portion 116. Compared to the distal portion 116, the proximal portion 114 is relatively closer to the proximal end 111 of the deployment wire 110. Likewise, compared to the proximal portion 114, the distal portion is relatively closer to the distal end 113 of the deployment wire 110.

During a procedure, a distal end of the distal portion 116 can be first inserted into the patient. The core wire 112 can comprise a variety of shapes and sizes. In some embodiments, the core wire 112 can have a constant diameter along its length, and in some embodiments, the core wire 112 can have a non-constant diameter along its length. In some embodiments, the core wire 112 comprises a tapered core wire 112, which tapered core wire 112 comprises a portion having a decreased diameter. In some embodiments, the tapered portion can taper to a point, and in some embodiments, the tapered portion can taper to a flattened delivery tip. The tapered portion can be, all or portions of, for example, the distal portion 116 of the core wire 112. In some embodiments, the portion of the core wire 112 having a decreased diameter can be, for example, up to a distal 5% of the core wire 112, up to a distal 10% of the core wire 112, up to a distal 15% of the core wire 112, up to a distal 20% of the core wire 112, up to a distal 25% of the core wire 112, up to a distal 30% of the core wire 112, up to a distal 40% of the core wire 112, up to a distal 50% of the core wire 112, or any other or intermediate portion.

In some embodiments, for example, the core wire 112 can have a length that is as long as, or longer than the catheter system 102. The core wire 112 can have a maximum outer diameter of, for example, up: 0.1 inches; 0.05 inches, 0.04 inches, 0.03 inches, 0.02 inches, 0.015 inches, 0.01 inches, 0.005 inches, or any other or intermediate value.

The deployment wire 110 can include one or several deployment features 118. The deployment features 118 can be located on the distal portion 116 of the core wire 112. The deployment features 118 can comprise one or several features configured to interact with the flow diverter to enable the core wire 112 to control and/or manipulate the core wire 112. In some embodiments, the deployment features can be configured to enable the core wire 112 to interact with the flow diverter to push the flow diverter into and/or move the flow diverter in and/or through the lumen of the catheter 104. In some embodiments, the deployment features 118 can be configured to couple the flow diverter to the core wire 112 such that the flow diverter can be deployed from the catheter 104 into the patient. Details of the deployment features 118 will be discussed at greater length below.

The flow diverter placement system 100 can include an introducer sheath 120. The introducer sheath 120 can comprise an elongate tubular member having a proximal end 122 and a distal end 124. In some embodiments, each of the proximal end 122 and the distal end 124 of the introducer sheath 120 can be open. The introducer sheath 120 can comprising an interior wall defining a lumen extending through the introducer sheath 120.

Figure 2:
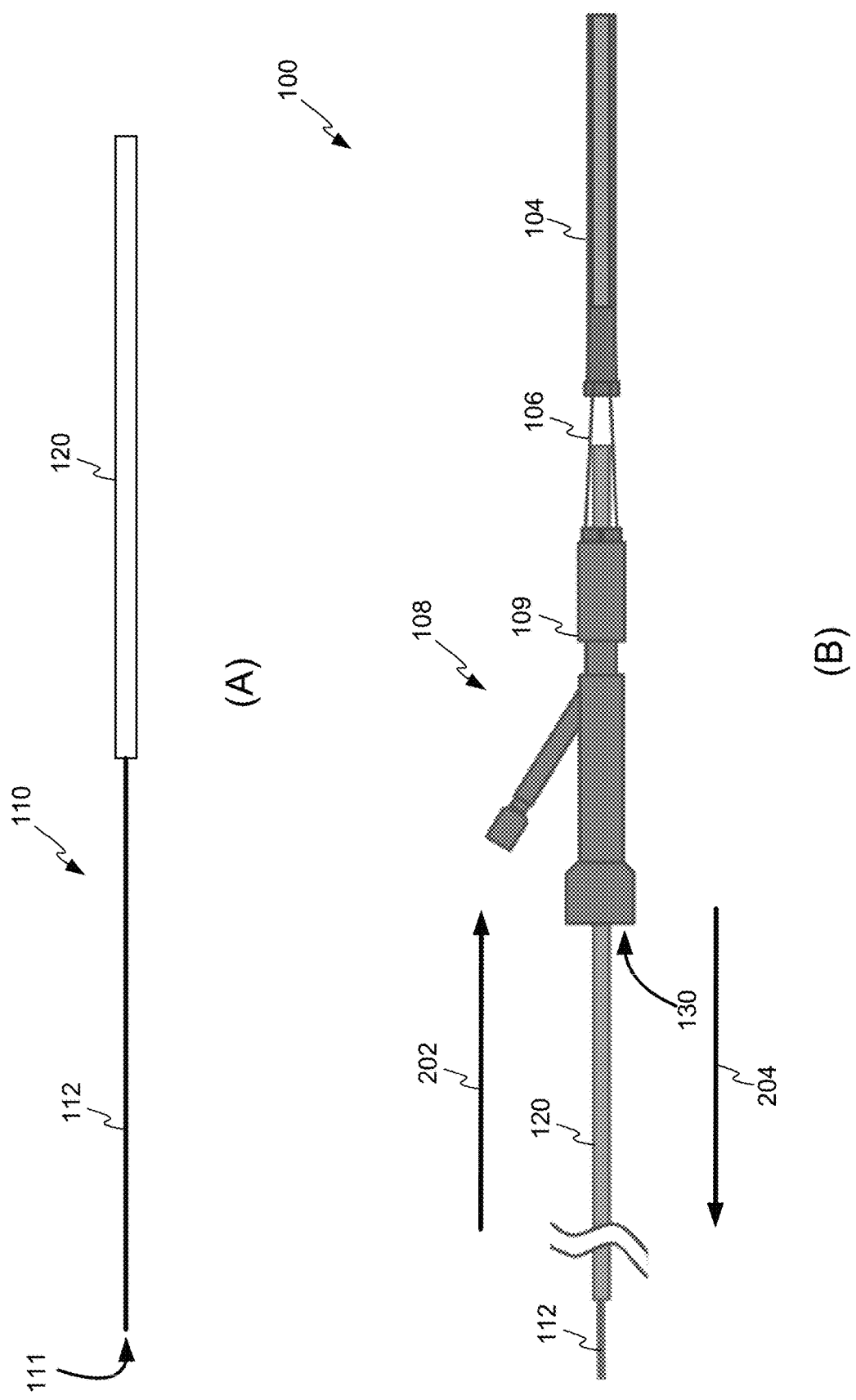
FIG. 2 is a depiction of the introducer sheath and the delivery of the flow diverter to the catheter via the introducer sheath.

The introducer sheath can be configured to hold the flow diverter before the flow diverter is inserted into the catheter system 102, and specifically into the proximal end 130 of the catheter system 102. In some embodiments, the introducer sheath 120 can be configured to hold the flow diverter in the lumen of the introducer sheath. In some embodiments, and as shown in FIG. 2(A), the introducer sheath 120 is holding the flow diverter in the lumen of the introducer sheath 120, and the deployment wire 110 is at least partially inserted into the lumen of the introducer sheath coupling the deployment features 118 of the deployment wire 110 with the flow diverter. As shown in FIG. 2(B), the introducer sheath 120, and specifically the distal end 124 of the introducer sheath 120 can be inserted into and through the access device 108 and into the catheter 104 and specifically into the catheter hub 106 of the catheter 104. In some embodiments, this can include inserting the combination of the introducer sheath containing the flow diverter and the deployment wire 110 into the catheter system 102 and specifically into the catheter 104.

In some embodiments, the introducer sheath 120 can be advanced through the access device 108 and into the catheter 104 in the direction indicated by arrow 202. The core wire 112 can inserted into the catheter system 102, and specifically into the proximal end 130 of the catheter system 102. In some embodiments, the core wire 112 can be inserted into the introducer sheath 120, which introducer sheath can be inserted into the catheter system 102.

The core wire 112 can be advanced in the direction indicated by arrow 202 through the introducer sheath 120 to advance the flow diverter from the introducer sheath 120 into the catheter 104. After the flow diverter is advanced into the catheter 104, the introducer sheath 120 can be retracted from the catheter 104 and from the access device 108 in the directed indicated by arrow 204.

With reference now to FIGS. 3 and 4, perspective view of an embodiment of a flow diverter 300 is shown. The flow diverter 300 can be, for example, a stent, a braided member, or the like. In some embodiments, a flow diverter can comprise an elongate braided member comprising a plurality of braided wires, which wires can be, for example, cobalt-chrome, Nitinol, or the like. The flow diverter 300 can, in some embodiments, comprise a tubular member defined by an external wall 302 having a first end 304, also referred to as a proximal end 304, and a second end 306, also referred to herein as a distal end 306. As seen in FIG. 4, the elongate tubular member of the flow diverter 300 can have a central axis 400 and can extend from a proximal end 402 to a distal end 404. A flow channel 406, also referred to herein as a diverter lumen 406, can be defined by an inner wall 403 of the flow diverter 300 and can extend along the central axis 400 and through the flow diverter 300. In some embodiments, each of the proximal end 402 and the distal end 404 can comprise an opening into the flow channel 406 such that fluid, and specifically blood can flow through the flow channel 406, flowing into the proximal end 402 and out the distal end 404.

The flow diverter 300 can be in a compressed state, also referred to herein as a constrained state, a delivery configuration, or as a constrained configuration as shown in FIG. 3, or can be in an expanded state, also referred to herein as an unconstrained stated and/or unconstrained configuration as shown in FIG. 4. In the constrained configuration, the flow diverter 300 can have a compressed outer diameter 308, in other words, cannot the flow diverter 300 in the constrained configuration is not fully expanded and/or is constrained so as not to be able to fully expand. In some embodiments, the flow diverter 300 can be held in the constrained state when the flow diverter is contained and/or constrained within the introducer sheath 120 and/or in the catheter 104. In some embodiments, the flow diverter can be sized to have a compressed outer diameter 308 that fits in the introducer sheath 120 and/or in the catheter.

In the unconstrained state, the flow diverter 300 can have an expanded outer diameter 408. The expanded diameter 408 can be larger than the compressed outer diameter 308.

In some embodiments, the flow diverter 300 can be self-expanding such that when the flow diverter 300 exits the catheter 104 into a patient's blood vessel, the flow diverter 300 automatically expands to match the inner diameter of that blood vessel. In some embodiments, the flow diverter 300 can be made in a variety of sizes for use in blood vessels of different sizes. In some embodiments, the flow diverter 300 can have an expanded diameter 408 of up to 20 mm, up to 12 mm, up to 10 mm, up to 8 mm, up to 7 mm, up to 6 mm, up to 5 mm, up to 4 mm, between 0.5 mm and 10 mm, between 1 mm and 8 mm, between 1.25 mm and 6.5 mm, or any other or intermediate diameter or range of diameters.

The flow diverter can be deployed into a patient's blood vessel through use of the system 100 of FIG. 1. The deployment can involve use of deployment features 119 of the deployment wire 110. Embodiments of deployment features 118 are depicted in FIGS. 5 through 21 below.

The flow diverter 300 can, in some embodiments, comprise a braided member. One embodiment of the braid of the flow diverter is depicted in 450, shown in detail in FIG. 5. As seen in FIG. 5, the braided member can be made from a plurality of wires 452, also referred to herein as strands 452. These wires 452 can comprise a variety of shapes and sizes and can be made from a variety of materials. In some embodiments, for example, the wires 452 can have a diameter of between approximately 0.0002 inches and approximately 0.01 inches, between approximately 0.0005 inches and approximately 0.005 inches, between approximately 0.0007 inches and approximately 0.002 inches, of approximately 0.0008 inches, of approximately 0.001 inches, of approximately 0.0012 inches, or any other or intermediate diameter.

In some embodiments, the wires 452 can comprise a variety of types and/or materials. In some embodiments, the wires 452 can comprise drawn filled tube (DFT). In some embodiments, the DFT can include an inner core and an outer tube. Each of the inner core and the outer tube can comprise a material. In some embodiments, one or both of the inner core and the outer tube can be radiopaque. In some embodiments, for example, the outer tube can provide strength to the braided member of the flow diverter 300 and the inner core can be radiopaque.

In some embodiments, for example, the inner core can comprise platinum and/or a platinum allow that can include, for example, platinum and tungsten. In some embodiment, the platinum alloy can comprise, for example, approximately 28% platinum. In some embodiments, the outer tube can comprise an alloy such as, for example, stainless steel, nitinol, cobalt chromium alloy such as 35N LT alloy, or the like.

In some embodiments, the wires can be cold worked, and specifically can have a minimum cold work of at least 30%, of at least 60%, of approximately 60.8%, or any other or intermediate amount of cold work. In some embodiments, the wires 452 can have a tensile strength minimum of at least approximately 50,000 PSI, of at least approximately 100,000 PSI, of at least 200,000 PSI, of approximately 235,000 PSI, of approximately 250,000 PSI, or any other or intermediate tensile strength minimum.

The braid of the flow diverter 300 can include any desired number of strands. In some embodiments, the braid of the flow diverter 300 can include between approximately 10 strands and approximately 200 strands, between approximately 20 strands and approximately 150 strands, between approximately 40 strands and approximately 100 strands, of approximately 64 strands, or any other or intermediate number of strands. As seen in FIG. 5, the wires 452 can include wires 452-A extending in a first direction and braided with wires 452-B extending in a second direction. The wires 452 can be braided in any desired way including, for example, a 1 wire over 1 under 1 braid, a 1 wire over 2 under 2 braid as shown in FIG. 5, or any other braid.

With reference now to FIG. 6, a schematic illustration of a first delivery system 500 is shown. The system 500 can include a flow diverter 300 that can be held in a constrained configuration within a lumen 502 defined by an interior wall 504 of a catheter 104 or of an introducer sheath 120.

The lumen 502 can comprise a variety of shapes and sizes. In some embodiments, the lumen 502 can comprise a cylindrical lumen, and specifically can have a circular cross section. The size of the lumen 502 can, in some embodiments, be defined by an internal diameter. In some embodiments, the lumen 502 can have an internal diameter of, for example, up to: 0.2 inches, 0.1 inches; 0.05 inches, 0.04 inches, 0.03 inches, 0.025 inches, 0.021 inches, 0.02 inches, 0.017 inches, 0.015 inches, 0.01 inches, 0.005 inches, or any other or intermediate value.

The deployment wire 110 can extend at least partially into both the flow diverter 300 and the lumen 502 of the catheter 104 or of the introducer sheath 120. The deployment wire 110, can include the core wire 112 which can extend into the lumen 502 of the catheter 104 and/or of the introducer sheath 120, and the deployment features 118, which are shown wholly within the lumen 502 of the catheter 104 and/or of the introducer sheath 120.

In the embodiment shown in FIG. 6, the deployment features 118 include a pusher 505 such as a pusher coil 506 wrapping around a portion of the core wire 112, one or several friction bumps 508. These one or several friction bumps can include, for example, a first friction bump 508-A, a second friction bump 508-B, and third friction bump 508-C. In some embodiments, these one or several friction bumps 508 can comprises a plurality of friction bumps 508 can be distributed along a portion of the deployment wire 110, and specifically can be distributed along a portion of the core wire 112. In some embodiments, and as shown in FIG. 6, the friction bumps 508 can be positioned inside of the flow channel 406 of the flow diverter 300 and can engage with the flow diverter 300.

In some embodiments, the one or several friction bumps 508 can comprise a single friction bump. This single friction bump can, for example, extend from the pusher 505 to the position of the third friction bump 508-C of FIG. 6. Thus, instead of having multiple friction bumps 508 across this length of the core wire 112, and single friction bump 508, also referred to herein as a friction pad can extend across all or portions of this length of the core wire 112. In some embodiments, this single friction pad can extend beyond a proximal portion of the flow diverter 300 and into a distal portion of the flow diverter 300.

In some embodiments, a single, long friction pad can provide for better engagement with the flow diverter 300. However, embodiments with multiple, spaced-apart friction bumps can provide for improved flexibility of the core wire 112. In some embodiments, the single, long friction pad can comprise the same material as the friction bumps 508, and in some embodiments, the single, long friction pad can comprise a material configured to improve flexibility.

The deployment features 118 further include a support coil 510, also referred to herein as a supporting coil 510, wrapping around a portion of the core wire 112, and particularly winding around the distal portions of the core wire 112, which distal portions can be tapered. As seen in FIG. 3, the supporting coil 510 can extend at least partially through the pusher coil 506, and can extend along the core wire 112 between friction bumps 508 and distally beyond a final friction bump 508, or as shown in FIG. 3, beyond the third friction bump 508-C. Specifically, and as seen in FIG. 6, the support coil 510 can begin at a location between the proximal end 514 and the distal end 516 of the pusher 505 and/or of the pusher coil 506, and can distally extend to a location distally beyond the final friction bump 508. In such an embodiment, the support coil 510 can be intermediate between at least a portion of the pusher 505 and/or the pusher coil 506 and the core wire 112. The deployment features 118 can also include an atraumatic tip 512 at a distal most end of the deployment wire 110.

In some embodiments, the portion of the support coil 510 extending distally beyond the final friction bump 508 can support the flow diverter 300. Specifically, the portion of the support coil 510 extending distally beyond the final friction bump 508 can extend through at least a portion of the length of the flow diverter 300 and can, in some embodiments, strengthen those portions of the flow diverter 300. Specifically, and in some embodiments, the portion of the support coil 510 extending distally beyond the final friction bump 508 can prevent the flow diverter from collapsing and/or buckling.

The deployment wire 110, including the deployment features 118 can be configured for navigating a patient's vasculature, and specifically for navigating a patient's neurovasculature. Thus, in some embodiments, the deployment features 118 can be configured to facilitate and/or maintain flexibility of the core wire 112, and specifically of the distal portion 116 of the core wire 112.

The pusher coil 506 can be configured to apply a force to the flow diverter 300 when the deployment wire 110 is distally advanced into and/or through the catheter 104 and/or the introducer sheath 120. The pusher coil 506 can comprise a coil formed by wire winding. The wire forming the wire winding can comprise a variety of materials and sizes. In some embodiments, the wire forming the pusher coil 506 can comprise a biocompatible wire such as a Nitinol wire. The wire forming the pusher coil 506 can comprise a diameter of, for example, between 0 and 0.01 inches, between 0 and 0.005 inches, between 0 and 0.002 inches, approximately 0.002 inches, or any other or intermediate diameter.

The pusher coil 506 can have an outer diameter that is sized to fit in the lumen 502 of the catheter 104 and/or of the introducer sheath 120. In some embodiments, the pusher coil 506 can have a diameter that is less than the diameter of the lumen 502 of the catheter 104 and/or less than the inner diameter of the lumen of the introducer sheath 120. The outer diameter of the pusher coil can be sized with respect to the diameter of the lumen 502 of the catheter 104 and/or of the introducer sheath 120 such that flow diverter 300 does not fit between pusher coil 506 and the interior wall 504 of the catheter 104 and/or of the introducer sheath 120. In some embodiments in which the lumen 502 of the catheter 104 and/or of the introducer sheath 120 has an internal diameter of 0.017 inches, the pusher coil 506 can have an outer diameter of, for example, 0.015 inches. In some embodiments in which the lumen 502 of the catheter 104 and/or of the introducer sheath 120 has an internal diameter of 0.021 inches, the pusher coil 506 can have an outer diameter of, for example, 0.019 inches.

The pusher coil 506 can have a proximal end 514 and a distal end 516. In some embodiments, one or both of the proximal end 514 and the distal end 516 of the pusher coil 506 can be configured to affix the pusher coil 506 to the deployment wire 110. In some embodiments, one or both of the proximal end 514 and the distal end 516 of the pusher coil 506 can comprise solder affixing the pusher coil 506 to the deployment wire 110, or in other words, the pusher coil 506 can be soldered to the deployment wire 110. In some embodiments, the distal end 516 of the pusher coil 506 can be further configured to provide a bearing surface with which the pusher coil 506 can apply a force to the flow diverter 300. In some embodiments, the bearing surface can be formed in the solder of the distal end 516. In some embodiments, the distal end 516 of the pusher coil 506 can comprise a bumper portion configured to engage with the flow diverter 300. The bumper portion can be convex to better engage with the flow diverter 300. In some embodiments, the bumper portion can comprise a flattened tube.

The deployment features 118 can comprise one or several friction bumps 508. In some embodiments, a friction bump is configured to press a portion of the flow diverter 300 into the interior wall 504 of the catheter 104 and/or the introducer sheath 120 when that portion of the flow diverter 300 in within the catheter 104 and/or the introducer sheath 120. In some embodiments, the friction bump 508 can comprise a material that engages, and specifically that deformably engages, with the flow diverter 300 such that a friction force between the flow diverter 300 and the friction bump 508 is greater than a friction force between the flow diverter 300 and the internal wall 504 of the catheter 104 and/or introducer sheath 120. Due to the comparatively greater friction force between the friction bump 508 and the flow diverter 300, each friction bump 508 facilitates control of the flow diverter 300, and specifically facilitates control of the position of the flow diverter 300 with respect to the catheter 104 and/or introducer sheath 120. In some embodiments, the interaction between a friction bump 508 and the flow diverter 300 can enable the deployment wire 110 to deploy the flow diverter 300 from the catheter 104 and/or retract and/or partially retract a partially deployed flow diverter 300 back into the catheter 104.

The friction bump 508 can comprise, for example, a deformable material such as an elastomer. In some embodiments, the friction bumps 508 can comprise a polymer that can encase a radiopaque element such as, for example, a platinum coil and/or platinum wire. In some embodiments, the friction bumps 508 can comprise a tungsten loader polymer or a tungsten loaded elastomer. In some embodiments, the friction bumps can comprise a UV glue, which can be, for example, doped with a radiopaque material such as, for example, tantalum powder. In some embodiments some or all of the friction bumps 508 can be radiopaque and/or include a radiopaque element. In some embodiments, the radiopaque element can comprise one or several radiopaque particles embedded in the friction bump 508, and in some embodiments, and as shown in FIG. 6, the friction bump can comprise a radiopaque coil 509, which can comprise, for example, a piece of wire such as a coil of platinum wire.

In some embodiments in which the deployment wire 110 comprises a plurality of friction bumps 508, the friction bumps 508 can be equally or unequally spaced. In some embodiments, the friction bumps 508 can be spaced apart so as to be separated by between 1 mm and 20 mm, by between 1 mm and 15 mm, by between 2 mm and 10 mm, by between 3 mm and 8 mm, by approximately 5 mm, or by any other or intermediate value.

In some embodiments, the deployment features 118 can include support coil 510. Support coil 510 can prevent the core wire 112 from buckling when the core wire 112 is distally advancing the flow diverter 300 in the catheter 104 and/or in the introduction sheath 120. For example, to increase the flexibility of the core wire 112, the core wire 112 can taper at its distal portion 116. This taper can increase the flexibility of the core wire 112, but also decreases the strength of the core wire 112. This decrease in strength of the core wire 112 can result in the core wire 112 buckling when the core wire 112 is used to distally advance the flow diverter 300 in the catheter 103 and/or in the introduction sheath 120. The supporting coil 510 can extend along portions of the core wire 112 to prevent the core wire 112 from buckling. Thus, through the combination of the tapered core wire 112 and the support coil 510, the deployment wire 110 can be flexible to navigate tortuous vasculature while also having sufficient strength to deploy the flow diverter 300.

As seen in FIG. 6, the support coil 510 can extend over portions of the core wire 112, and specifically over all or portions of the distal portion 116 of the core wire 112. As further seen in FIG. 16, the support coil 510 can extend over the core wire 112 between the friction bumps 508, and distally beyond the last friction bump 508, or more specifically, distally beyond the third friction bump 508-C.

The wire forming the support coil can comprise a diameter of, for example, between 0 and 0.01 inches, between 0 and 0.005 inches, between 0 and 0.002 inches, approximately 0.002 inches, or any other or intermediate diameter. In some embodiments, the wire forming the support coil 510 can have the same diameter as the wire forming the pusher coil 506, and in some embodiments, the wire forming the support coil 510 can have a different diameter than the wire forming the pusher coil 506. In some embodiments, the supporting coil 510 can have an outer diameter of, for example, up to 0.04 inches, up to 0.03 inches, up to 0.02 inches, up to 0.015 inches, up to 0.01 inches, up to 0.005 inches, up to 0.001 inches, or any other or intermediate value.

The deployment wire 110 can extend distally beyond the friction bumps 508, and in some embodiments, distally beyond the third friction bump 508-C. The deployment wire 110 can terminate with an atraumatic tip 512 that can be located at the distal end of the deployment wire 110. In some embodiments, the portion of the deployment wire 110 extending distally beyond the friction bump 508 can include a portion of the support coil 510. The atraumatic tip 512 can be configured to not damage tissue it may be bumped into during the performing of a procedure, and specifically during the deploying of a flow diverter 300 in a patient's vasculature. The atraumatic tip 512 can be attached to the distal end of the core wire 112 and/or to the distal end of the support coil 510. The atraumatic tip can have a diameter matching the outer diameter of the supporting coil 510. In some embodiments, the atraumatic tip 512 can be spaced apart from the last friction bump 508 by between 1 mm and 20 mm, by between 1 mm and 15 mm, by between 2 mm and 10 mm, by between 3 mm and 8 mm, by approximately 5 mm, or by any other or intermediate value.

In some embodiments, the delivery system, and as shown in FIG. 6, the first delivery system 500 can include a retraction sleeve 520. The retraction sleeve 520 can be coupled to the deployment wire 110 and can extend over a proximal portion 522 of the flow diverter 300. In some embodiments, the retraction sleeve 520 can extend over the proximal portion 522 of the flow diverter 300 when the flow diverter 300 is contained within the introducer sheath 120 and/or the catheter 104. In some embodiments, the retraction sleeve 520 can extend some or all of the length of the deployment features 118, and thus can extend over some or all of the proximal portion 522 of the flow diverter 300 engaging with the deployment features 118.

In some embodiments the retraction sleeve 520 can be positioned intermediate between the proximal portion 522 of the flow diverter 300 and the introducer sheath 120 and/or the catheter 104 and can thereby reduce friction between the proximal portion 522 of the flow diverter 300 and the introducer sheath 120 and/or the catheter 104. In some embodiments, the retraction sleeve 520 can not only decrease friction between the proximal portion 522 of the flow diverter 300 and the introducer sheath 120 and/or the catheter 104, but can also protect the proximal portion 522 of the flow diverter from damage that may arise from movement of the flow diverter 300 with respect to the introducer sheath 120 and/or the catheter 104 such as can occur during the deployment and/or retraction of the flow diverter 300.

The retraction sleeve 520 can comprise a flexible polymer that can be coupled to the deployment wire 110. In some embodiments, the retraction sleeve 520 can be coupled to the deployment wire 110 at a position distal of all or portions of the deployment features 118, as shown in FIG. 6. In some embodiments, the retraction sleeve 520 can comprise a heat-shrink polymer tube that can be position over the proximal portion 522 of the flow diverter 300 and over a portion of the deployment wire 110 distal of the flow diverter 300. The retraction sleeve 520 can then be heat-shrunk around the flow diverter 300 to snugly fit around the flow diverter 300.

The retraction sleeve 520 can further include one or move slits extending proximally from a distal end of the retraction sleeve 520. The one or more slits separate the portion of the retraction sleeve 520 extending over the proximal portion 522 of the flow diverter 300 into a plurality of segments. For example, in an embodiment of the retraction sleeve 520 containing two slits, the retraction sleeve 520 can be divided into two pieces, which can be two equal halves. The one or more slits can allow the retraction sleeve 520 to open and separate from the flow diverter 300 as the flow diverter 300 is deployed. Thus, as seen in FIG. 7, as the retraction sleeve 520 protrudes distally beyond the catheter 104. As seen the retraction sleeve 520 extending distally beyond the catheter 104 has split and separated from the flow diverter 300, allowing the flow diverter 300 to expand, and allowing the retraction of the retraction sleeve 520 into the catheter 104 upon full deployment of the flow diverter 300.

With reference now to FIG. 7, a schematic depiction of the first delivery system 500 in a partially deployed configuration is shown. As seen in FIG. 7, the catheter 104 containing the deployment wire 110 and the flow diverter 300 is in a blood vessel 600. As further seen in FIG. 7, the deployment wire 110 has been distally advanced, as indicated by arrow 602, with respect to the catheter 104, thereby partially deploying the flow diverter 300. The combination of the friction bumps 508 and the pusher coil 506 engage with the flow diverter 300 to cause the flow diverter 300 to distally advance in and out of the catheter 104 when the deployment wire 110 is distally advanced. As the deployment wire 110 is distally advanced, the flow diverter 300 deploys from the catheter 104 and begins to expand. This distal advance continues until the flow diverter 300 is fully deployed. Alternatively, if the flow diverter 300 has not been fully deployed from the catheter 104, and in the event that at least one of the friction bumps 508 is still within the catheter 104 and engaging with the flow diverter 300, the flow diverter 300 can be retracted and/or partially retracted into the catheter 104. In some embodiments, a successful deployment of a flow diverter 300 can be achieved by only distally advancing the deployment wire 110, and in some embodiments, a successful deployment of the flow diverter 300 can be achieved by alternatingly distally advancing and proximally retracting the flow diverter 300 until a desired positioning and/or deployment is achieved.

With reference now to FIG. 8, a schematic depiction of a second delivery system 700 is shown. The system 700 can include a flow diverter 300 that can be held in a constrained state within a lumen 502 defined by an interior wall 504 of a catheter 104 or of an introducer sheath 120.

The deployment wire 110 can extend at least partially into both the flow diverter 300 and the lumen 502 of the catheter 104 or of the introducer sheath 120. The deployment wire 110, can include the core wire 112 which can extend into the lumen 502 of the catheter 104 and/or of the introducer sheath 120, and the deployment features 118, which are shown wholly within the lumen 502 of the catheter 104 and/or of the introducer sheath 120.

The deployment features 118 include at least one friction bump 508 and delivery coils 702. The friction bump 508 and the delivery 702 can engage with, and as shown in FIG. 8, can be engaged with the flow diverter 300 when the flow diverter is within the catheter 300 and/or within the introducer sheath 120. Each of the friction bump 508 and the delivery coils 702 can be coupled to the delivery wire 100, and specifically can be coupled to the core wire 112. In some embodiments the friction bump 508 and/or one or more of the delivery coils 702 can be radiopaque and/or can comprise a radiopaque element.

The delivery coils 702 can include proximal delivery coils 702-A and distal delivery coils 702-B. Each of the delivery coils 702 can comprise a proximal end and a distal end, the proximal end of a delivery coil 702 relatively more proximate to the proximal end of the core wire 112 than is the distal end of that delivery coil 702.

The delivery coils 702 can each comprise a wire winding. The wire forming the delivery coil 702 can comprise a diameter of, for example, between 0 and 0.01 inches, between 0 and 0.005 inches, between 0 and 0.002 inches, approximately 0.002 inches, or any other or intermediate diameter. In some embodiments, and as shown in FIG. 8, the distal delivery coils 702-B extend to a distal end 704 of the deployment wire 110, and at least one friction bump 508 can be located between the proximal delivery coil 702-A and the distal delivery coil 702-B.

The delivery coils 702 can be configured to press a portion of the flow diverter 300, and specifically the portion of the flow diverter 300 contacting the delivery coils, into the interior wall 504 of the catheter 104 and/or the introducer sheath 120 when that portion of the flow diverter 300 in within the catheter 104 and/or the introducer sheath 120. In some embodiments, the delivery coils 702 can engage with the flow diverter 300 such that a friction force between the flow diverter 300 and the delivery coils 702 is greater than a friction force between the flow diverter 300 and the internal wall 504 of the catheter 104 and/or introducer sheath 120. Due to the comparatively greater friction force between the delivery coils 702 and the flow diverter 300, each delivery coil 702 facilitates control of the flow diverter 300, and specifically facilitates control of the position of the flow diverter 300 with respect to the catheter 104 and/or introducer sheath 120. In some embodiments, the interaction between a delivery coil 702 and the flow diverter 300 can enable the deployment wire 110 to deploy the flow diverter 300 from the catheter 104 and/or retract and/or partially retract a partially deployed flow diverter 300 back into the catheter 104.

The delivery coils 702 can have an outer diameter that is sized to fit in the lumen 502 of the catheter 104 and/or of the introducer sheath 120. In some embodiments, the delivery coils 702 can have a diameter that is less than the diameter of the lumen 502 of the catheter 104 and/or less than the inner diameter of the lumen of the introducer sheath 120. The outer diameter of the delivery coils 702 can be sized with respect to the diameter of the lumen 502 of the catheter 104 and/or of the introducer sheath 120, and with respect to the dimensions of the flow diverter 300 such that the flow diverter 300 is pressed by the delivery coil 702 into the interior wall 504 of the catheter 104 and/or introducer sheath 120 with a force such that flow diverter 300 moves with the deployment wire 110 when the deployment wire 110 is moved with respect to the catheter 104 and/or introducer sheath 120.

The delivery coils 702 can be mounted directly on the core wire 112, or in some embodiments, can be coupled to the core wire 112 via one or several spacers 706. In some embodiments, each of the proximal delivery coil 702-A and the distal delivery coil 702-B are coupled to the deployment wire 110, and specifically to the core wire 112 via at least one spacer 706.

The one or several spacers 706 can increase the diameter of the delivery coils 702 and can counteract to the taper of the core wire 112 to provide constant diameter of the delivery coils 702. The spacers 706 can comprise a metal, a polymer, an elastomer, or any desired material.

The spacers 706 can include a first spacer 706-A coupling a distal end of the proximal delivery coil 702-A to the core wire 112, a second spacer 706-B coupling a proximal end of the distal delivery coil 702-B to the core wire 112, and a third spacer 706-C coupling a distal end of the distal delivery coil 702-B to the core wire 112. In some embodiments, and as shown in FIG. 8, the proximal end of the proximal delivery coil 702-A directly couples to the core wire 112.

The spacers 706 counteract the taper of the core wire 112 such that each of the delivery coils 702 has a constant diameter, and such that the proximal delivery coil 702-A and the distal delivery coil 702-B have the same diameter. Thus, in some embodiments, the height of each of the first spacer 706-A, the second spacer 706-B, and the third spacer 706-C is configured such that the proximal delivery coil 702-A and the distal delivery coil 702-B have the same diameter and such that each of the proximal delivery coil 702-A and the distal delivery coil 702-B have a constant diameter. In some embodiments, the height of the spacers 706, and specifically of each of the first spacer 706-A, the second spacer 706-B, and the third spacer 706-C counteracts the taper of the distal portion 116 of the core wire 112.

Although not shown in FIG. 8, in some embodiments, the second delivery system 700 can include a pusher 505 and/or a support coil 510. In some embodiments, the pusher 505 can be a pusher coil 506. In some embodiments, the pusher 505 can extend along and around a portion of the deployment wire 110. In some embodiments, the pusher 505 can be located proximal of the proximal delivery coil 702. In some embodiments, the support coil 510 can extend along and around a distal portion 116 of the deployment wire 110 and specifically around a distal portion 116 of the core wire 112.

With reference now to FIG. 9, a schematic depiction of the second delivery system 700 in a partially deployed configuration is shown. As seen in FIG. 9, the catheter 104 containing the deployment wire 110 and the flow diverter 300 is in a blood vessel 600. As further seen in FIG. 9, the deployment wire 110 has been distally advanced, as indicated by arrow 602, with respect to the catheter 104, thereby partially deploying the flow diverter 300. The combination of the friction bump 508 and the delivery coils 702 engage with the flow diverter 300 to cause the flow diverter 300 to distally advance in and out of the catheter 104 when the deployment wire 110 is distally advanced.

As the deployment wire 110 is distally advanced, the flow diverter 300 deploys from the catheter 104 and begins to expand. This distal advance continues until the flow diverter 300 is fully deployed. Alternatively, if the flow diverter 300 has not been fully deployed from the catheter 104, and in the event that at least a portion of the proximal delivery coil 702-A is still within the catheter 104 and engaging with the flow diverter 300, the flow diverter 300 can be retracted and/or partially retracted into the catheter 104. In some embodiments, a successful deployment of a flow diverter 300 can be achieved by only distally advancing the deployment wire 110, and in some embodiments, a successful deployment of the flow diverter 300 can be achieved by alternatingly distally advancing and proximally retracting the flow diverter 300 until a desired positioning and/or deployment is achieved.

Figure 10:
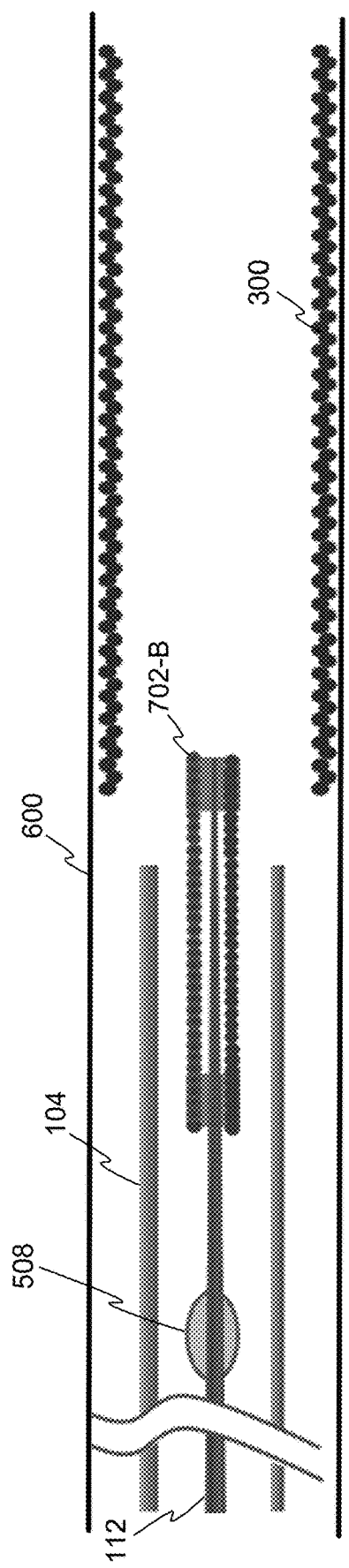
FIG. 10 is a depiction of the second delivery system in a deployed configuration.

With reference now to FIG. 10, a schematic depiction of the second delivery system 700 in a deployed configuration is shown. As seen in FIG. 10, the flow diverter 300 has exited the catheter 104 and has expanded to abut the blood vessel 600. Because the flow diverter 300 has expanded, the deployment wire 110 can be retracted into the catheter 104 without retracting the flow diverter 300.

Figure 11:
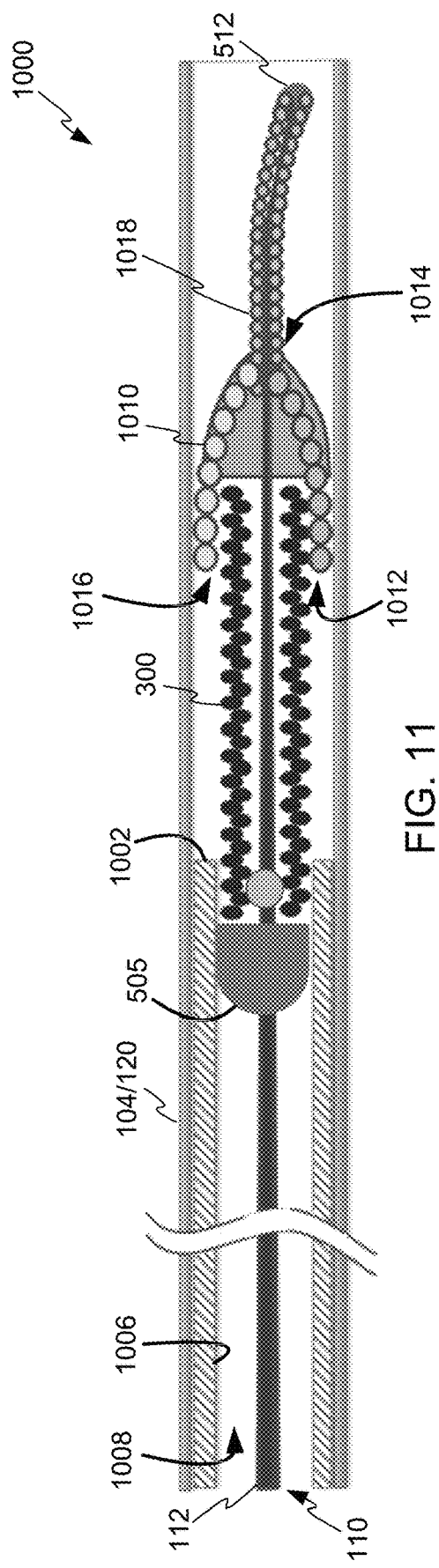
FIG. 11 is a depiction of a third delivery system.

With reference now to FIG. 11, a schematic depiction of a third delivery system 1000 is shown. The system 1000 can include a flow diverter 300 that can be held in a constrained configuration within the lumen 502 of the catheter 104 via a combination of a tube 1002 and a compression coil 1010.

The tube 1002 can comprise any elongate tubular member having an inner wall 1006 defining a lumen 1008 and that can be slidably contained within the catheter 104. In some embodiments, the tube 1002 can comprise a flexible tube configured to navigate neurovasculature, and in some embodiments, the tube 1002 can comprise a slotted and/or spiral-cut hypotube. In some embodiments, the slots and/or the spiral-cuts of the hypotube can be configured to increase the flexibility of the hypotube.

In some embodiments, the tube 1002 can comprise a proximal end (not shown) and a distal end 1004. The tube 1002 can comprise a tube inner wall 1006 that can define a tube lumen 1008. As seen in FIG. 11, the core wire 112 can extend through the tube lumen 1008 and distally beyond the tube 1002. As further seen in FIG. 11, a portion of the flow diverter 300 can be received within the lumen 1008 of the tube 1002, and specifically, a portion of the flow diverter 300 including the first end 304 can be received in the distal end 1004 of the lumen 1008 of the tube 1002.

The compression coil 1010 can comprise a member coupled to the deployment wire 110 and configured to receive a portion of the flow diverter 300, and specifically a portion of the flow diverter 300 including the second end 306. In some embodiments, the compression coil 1004 can compress this portion of the flow diverter 300 to maintain that portion of the flow diverter 300 in a compressed state.

The compression coil 1010 can include a proximal end 1012 and a distal end 1014. The proximal end 1012 can be open to an internal volume 1016. The internal volume 1016 as seen in FIG. 11 can be proximally facing such that a distal portion, including the second end 306, of the flow diverter 300 can be received within the internal volume 1016. In some embodiments, the portion of the flow diverter received within the internal volume 1016 of the compression coil 1010 can be held in a constrained state.

The compression coil 1010 can comprise, a wire wound in a coil, which coil can be a conical coil having a point at the distal end 1014 of the flow diverter 300 and a base at the proximal end 1012 of the flow diverter 300. The compression coil 1010 can have a diameter that is less than a diameter of the catheter 104 and can be slidably received within the lumen 502 of the catheter 104.

In some embodiments, the compression coil 1010 can engage the flow diverter 300 sufficient that the compression coil 1010 can pull the flow diverter 300 out of the tube 1002. In other words, the friction forces generated between the compression coil 1010 and the flow diverter 300 can be greater than the friction forces generated between the flow diverter 300 and the tube 1002. In some embodiments, however, the friction forces generated between the blood vessel 600 and the flow diverter 300 can be greater than the friction forces generated between the compression coil 1010 and the flow diverter 300. Thus, the advancement of the core wire 112 and the thereto coupled compression coil 1010 can pull the flow diverter 300 out of the tube 1002. The flow diverter 300, as it is pulled from the tube 1002 can expand and can engage the blood vessel 300. Once the flow diverter 300 has sufficiently engaged the blood vessel 600, further distal advancement of the core wire 112 and the thereto coupled compression coil 1010 can release the flow diverter 300 from the compression coil 1010. If any portion of the flow diverter 300 is still within the tube 1002, the proximal retraction of the tube 1002 or the tube 1002 and the catheter 104 can result in the full deployment of the flow diverter 300. Once the flow diverter is fully deployed, the compression coil 1010 can be proximally retracted through the flow diverter 300 and back into the catheter 104.

In some embodiments, and as shown in FIG. 11, the core wire 112 can couple to the proximal end 1014 of the compression coil 1010. In some embodiments, the core wire 112 can extend distally beyond the compression coil 1010. In some embodiments, a tip coil 1018, which can be a flexible tip coil 1018, can distally extend from the compression coil 1010, and specifically from the distal end 1014 of the compression coil 1010. The tip coil 1018 can extend along and around all or portions of the core wire 112 extending distally beyond the compression coil 1010. The tip coil 1018 and/or the core wire 112 can terminate in an atraumatic tip 512. The atraumatic tip 512 can, in some embodiments, be at the distal most point of the core wire 112 and/or of the tip coil 1018. In some embodiments, the flexible tip coil 1018 and/or the flexible tip coil 1018 and the atraumatic tip 512 can facilitate in navigating the system 1200 and/or the core wire 112 through the vasculature, and specifically through tortuous vasculature.

As seen in FIG. 11, the third delivery system 1000 can include at least one friction bump 508. The at least one friction bump 508 can be coupled to the core wire 112 and can be proximally spaced from the compression coil 1010 so as to engage a portion of the flow diverter 300 proximate to the first end 304 when the second end 306 of the flow diverter is received by the compression coil 1010.

In some embodiments, and as shown in FIG. 11, the third delivery system 1000 can include a pusher 505, which pusher 505 can be, for example, a pusher coil 506. The pusher 505 can be coupled to the core wire 112, and specifically can be coupled to the core wire 112 at a distance from proximal end 1012 of the compression coil 1010 such that the flow diverter 300 is held constrained by the tube 1002 and between the compression coil 1010 and the pusher 505 until the first end 304 of the flow diverter 300 deploys from the tube 1002. At which point, the flow diverter 300 can expand, allowing the pusher 505 to push through the flow diverter 300 while allowing the compression coil 1010 to further advance to separate the compression coil 1010 from the flow diverter 300.

In some embodiments, one or more of the friction bump 508, the tube 1002, the pusher 505, and the compression coil 1010 are radiopaque and/or include a radiopaque element. This radiopaque element can include a radiopaque wire, and specifically a radiopaque wire coil. In some embodiments, the wire forming this wire core can be platinum or any other radiopaque material.

Figure 12:
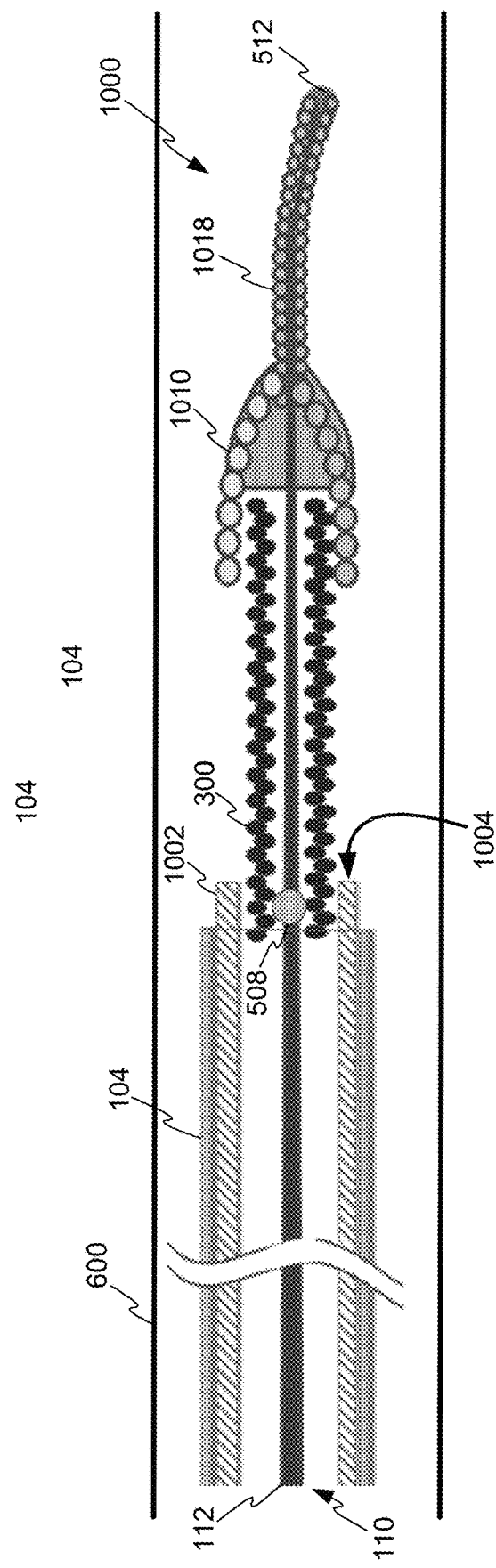
FIG. 12 is a depiction of one embodiment of the deployment of the third delivery system.

With reference now to FIG. 12, a depiction of one embodiment of the deployment of the third delivery system 1000 is shown. As seen in this figure, the catheter 104 has been advanced proximate to a treatment region in a blood vessel 600. The catheter 104 advanced proximate to the treatment region in the blood vessel 600 can be at a position at, near, or beyond the treatment region in the blood vessel 600. In some embodiments, this can include positioning the catheter 104 distal to the treatment region in the blood vessel 600.

The tube 1002 and the core wire 112 have been advanced such that the distal end 1004 of the tube 1002 is at or distally beyond the end of the catheter 104. In some embodiments, the tube 1002 and the core wire 112 can be advanced to a desired location with respect to the treatment site, which desired location can be, in some embodiments, distal of the treatment site or an intermediate location in the treatment site.

Once in the desired location, the flow diverter 300 can be deployed by relatively advancing the core wire 112 with respect to the tube 1002. This can be accomplished by advancing the core wire 112 while maintaining the position of the tuber 1002, retracting the tube 1002 while maintaining the position of the core wire 112, or advancing the core wire 112 while retracting the tube 1002.

In some embodiments, the core wire 112 and the thereto coupled compression coil 1010 are distally advanced, thereby pulling and/or deploying the flow diverter 300 from the tube 1002. As the flow diverter 300 deploys, its deployed portions expand and begin to engage with the blood vessel 600. As both of the ends of the flow diverter 300 are contained within either the compression coil 1010 or the tube 1002, during deployment, an intermediate portion of the flow diverter 300 is first deployed, and then expands. The expanded portion can engage with the wall of the blood vessel, which engagement can assist in deploying the remainder of the flow diverter 300. Specifically, once the flow diverter 300 is deployed from the tube 1002, the engagement between the deployed portions of the flow diverter 300 and the walls of the blood vessel 600 can facilitate in completing deployment of the flow diverter 300 from the compression coil 1010.

Further, as each of the ends of the flow diverter 300 are still contained within one of the compression coil 1010 and the tube 1002, the control of the deployment of the flow diverter 300 is improved. Specifically, the system 1000 maintains control of both ends 402, 404 of the flow diverter 300. Due to this improved control the system 1000 eases repositioning of a partially deployed flow diverter.

As the engagement between the flow diverter 300 and the blood vessel 600 increases, the flow diverter 300 begins to pull out of the compression coil 1010. If any portion of the flow diverter remains in the tube 1002, the core wire 112 can be further distally advanced to deploy the remaining portion of the flow diverter 300 and/or the tube 1002 can be proximally retracted. Due to the engagement between the deployed portions of the flow diverter 300 and the blood vessel 600, the remaining portions of the flow diverter 300 can be pulled from the tube 1002 and can deploy. Once the flow diverter 300 is deployed and expanded, the compression coil 300 can be proximally retracted through the flow diverter 300 and back into the catheter 104.

Figure 13:
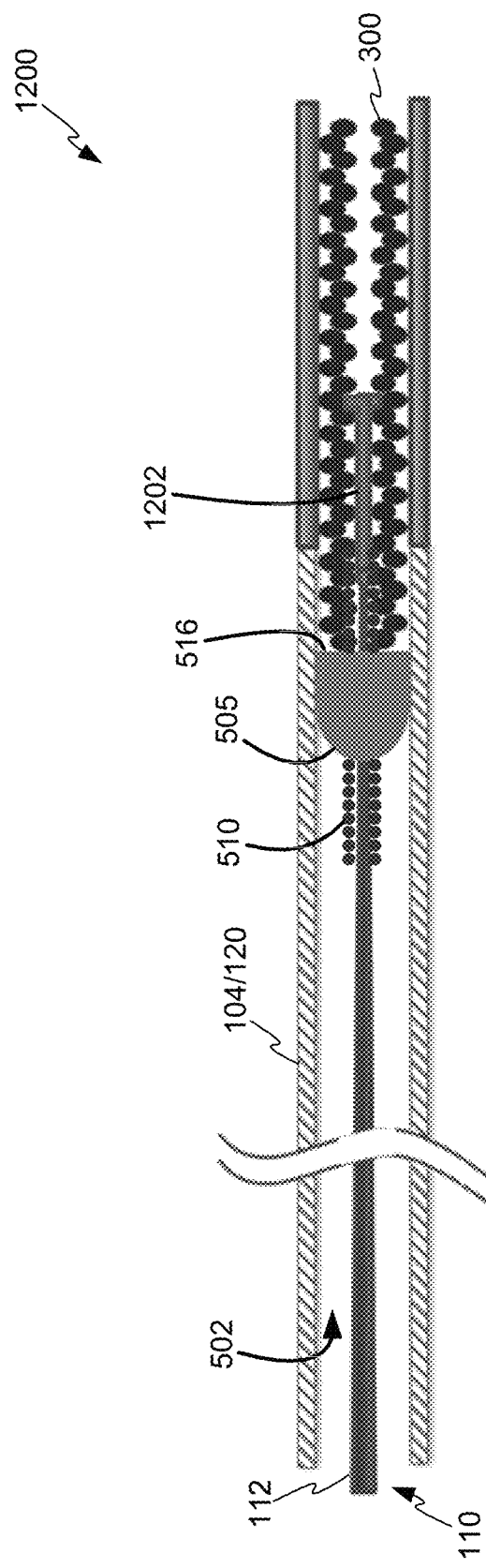
FIG. 13 is a depiction of a fourth delivery system.

With reference now to FIG. 13 a schematic depiction of a fourth delivery system 1200 is shown. The system 1200 can include a flow diverter 300 that can be held in a constrained state within the lumen 502 of the catheter 104 and/or of an introducer sheath 120.

The deployment wire 110 can extend at least partially into both the flow diverter 300 and the lumen 502 of the catheter 104 or of the introducer sheath 120. The deployment wire 110, can include the core wire 112 which can extend into the lumen 502 of the catheter 104 and/or of the introducer sheath 120, and the deployment features 118, which are shown wholly within the lumen 502 of the catheter 104 and/or of the introducer sheath 120.

The deployment features 118 include at least one pusher 505 and a claw mechanism 1202, also referred to herein as grabber mechanism 1202. The claw mechanism 1202 and the pusher 505 shown in FIG. 13 are engaged with the flow diverter such that a movement of the core wire 112 relative to the catheter 104 and/or the introducer sheath 120 likewise moves the flow diverter 300 relative to the catheter 104 and/or to the introducer sheath 120.

The pusher 505 can be, for example, a pusher coil 506. The pusher 505 can extend around and/or along a part of the distal portion 116 of the core wire 112. In some embodiments, the pusher 505 can include a distal end 516 that can, and, as shown in FIG. 13, is engaged with a first end 304 of the flow diverter 300. The pusher 505 can be coupled to the core wire 112. Specifically, the pusher 505 can be coupled to the core wire 112 proximal of the distal end 113 of the core wire 112 such that the core wire 112 extends distally beyond the pusher 505.

The claw mechanism 1202 can be configured to engage with the flow diverter 300. Via this engagement between the claw mechanism 1202 and the flow diverter 300, the claw mechanism can transfer forces and/or movement from the core wire 112 to the flow diverter 300 such that the flow diverter 300 can be deployed via distally advancing the core wire 112.

The claw mechanism 1202 can comprise a variety of shapes and sizes, and can be made from a variety of materials such as, for example, tungsten, titanium, stainless steel, cobalt chromium, or the like. In some embodiments, all or portions of the claw mechanism can be rigid, flexible, and/or radiopaque. In some embodiments, the claw mechanism 1202 can be sized to be received within the lumen 502 of the catheter 104 and/or of the introducer sheath 120, and to engage with a flow diverter 300 also contained within that lumen 502.

The claw mechanism 1202 can comprise an elongate body 1204. The elongate body 1204 can comprise a variety of shapes and sizes and can be made from a variety of materials. In some embodiments, the elongate body 1204 can be, for example, made of tungsten, titanium, stainless steel, cobalt chromium, or the like. In some embodiments, all or portions of the elongate body 1204 are rigid, flexible, and/or radiopaque.

The elongate body 1204 of the claw mechanism 1202 can comprise a proximal end 1206 and a distal end 1208. In some embodiments, and as shown in the view 1302 of FIG. 14, the proximal end 1206 of the elongate body 1204 can couple to the distal end 113 of the core wire 112. In some embodiments, the proximal end 1206 of the elongate body 1204 can couple to the distal end 113 of the core wire 112 at a junction 1210. In some embodiments, the coupling of the elongate body 1204 to the core wire 112 can be a flexible coupling, and in some embodiments, the junction 1210 is flexible. In some embodiments, the flexibility of the coupling of the elongate body 1204 to the core wire 112 can be the result of the flexibility of the core wire, and specifically of the flexibility of the tapered distal portion 116 of the core wire 112.

The claw mechanism 1202 can comprise one or several claws 1212, also referred to herein as one or several grabbers 1212 or as one or several grabber elements 1212. In some embodiments, the grabber elements 1212 can comprise the same material as the elongate body 1204. In some embodiments, the grabber elements 1212 can be rigid, and in some embodiments, the grabber elements 1212 can be flexible.

Each of the one or several grabbers 1212 can, in some embodiments, radially extend from the elongate body 1204. Some or all of the one or several grabber elements 1212 can be configured to engage with the flow diverter 300. The shape of exemplary grabbers 1212 is shown in the view 1304 of FIG. 14. The view 1303 is taken along view plane A-A, and is perpendicular to the view 1302 of FIG. 14.

In some embodiments, each of which one or several grabber elements 1212 can engage with the flow diverter 300 via one or several engagement features 1306. In some embodiments, each of the engagement features 1308 can comprise a protrusion and/or a point. Some or all of the engagement features of a grabber 1212 can engage with a portion of the flow diverter 300. Specifically, in some embodiments, some or all of the engagement features 1306 can be sized and/or shaped to engage with the structure of the flow diverter 300, and specifically to fit into openings in the flow diverter. Via this engagement, when the core wire 112 is advanced, the engagement features 1306 that are engaged with the structure of the flow diverter 300 apply force to the flow diverter 300 to cause the flow diverter 300 to advance. In some embodiments in which the flow diverter 300 comprises a braided member, the engagement features 1306 are configured to fit and/or partially fit between the braided and/or woven fibers and/or strands forming the braided flow diverter 300.

Figure 14:
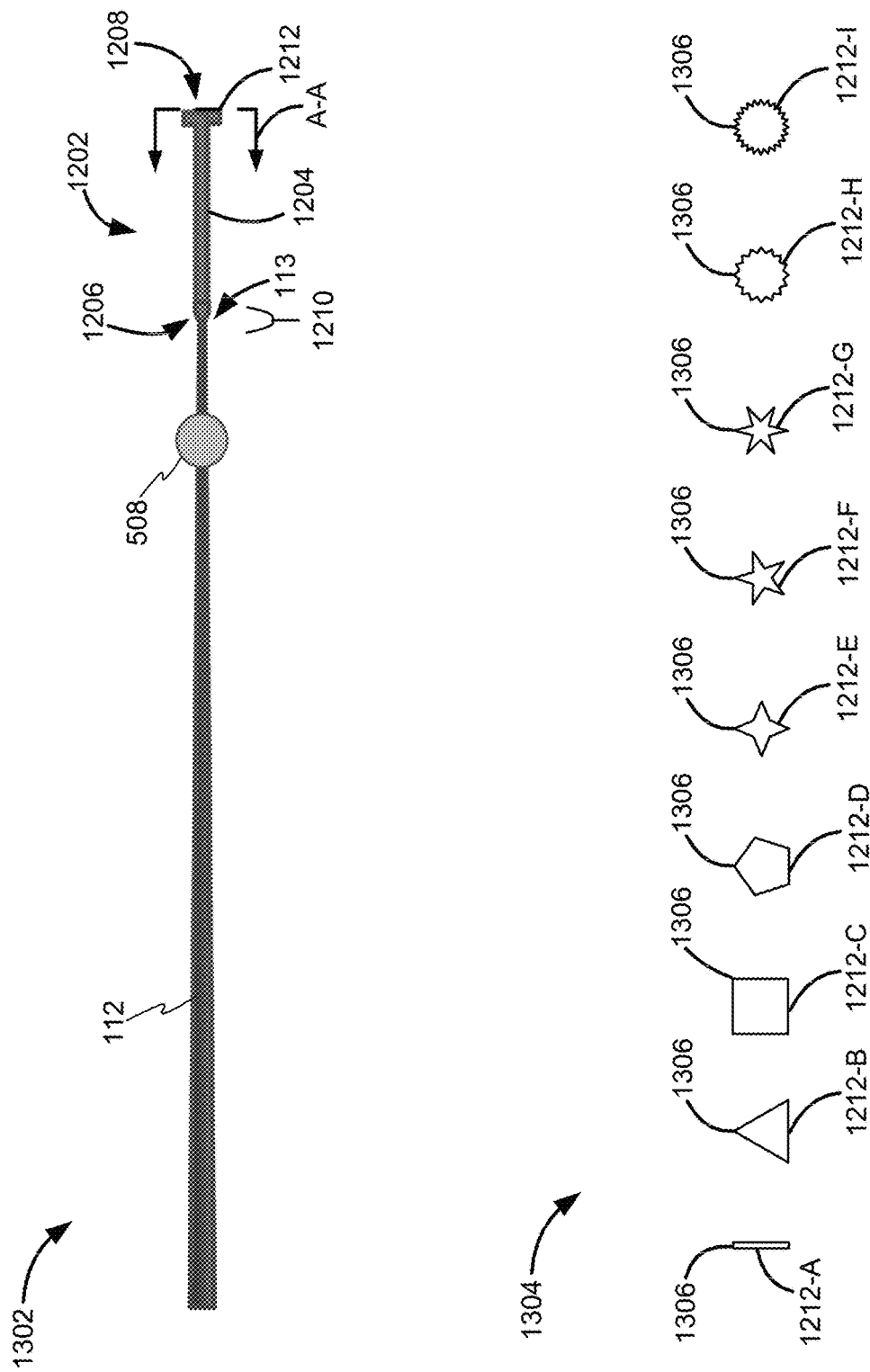
FIG. 14 is depiction of one embodiment of a claw mechanism.

As seen in view 1304 of FIG. 14, the grabber 1212 can comprise a variety of shapes and sizes and can have desired number of engagement members 1306. For example, a grabber 1212-A can comprise a rectangular or cylindrical member that together with the elongate body 1204 forms a T-shape. In such an embodiment, the grabber 1212-A can comprise two engagement members 1306. The grabber 1212-B can comprise a triangle shape that can have three engagement members 1306, the grabber 1212-C can comprise a square and/or rectangle shape having four engagement members 1306, the grabber 1212-D can comprise a pentagon having five engagement members 1306, or in some embodiments, the grabber 1212 can comprise a hexagon having six engagement members 1306, a heptagon having seven engagement members 1306 or an octagon having eight engagement members 1306. In some embodiments, the grabber 1212 can be star shaped such, for example, as grabber 1212-E having four engagement members 1306, grabber 1212-F having five engagement members 1306, and grabber 1212-G having six engagement members 1306. In some embodiments, grabber 1212 can be sprocket shaped such as, for example, grabber 1212-H and grabber 1212-I.

The grabber element 1212 and the grabber mechanism 1202 provide significant benefits in that that the grabber element 1212 engages with the flow diverter 300 via engaging with the structure of the flow diverter 300 as opposed to via a friction force between the flow diverter 300 and an element, for example, compressing the flow diverter 300 into the interior wall 504 of the lumen 502 of the catheter 104 and/or of the introducer sheath 120. In such an engagement between the grabber element 1212 and the structure of the flow diverter 300, one or several of the engagement members 1306 of the grabber 1212 extend into the braid of the flow diverter 300, such that one or several of the fibers forming the braid of the flow diverter overlay portions of the distal end 1208 of the of the grabber mechanism 1202, and specifically overlay the portions of the distal end 1208 of the grabber mechanism formed by the engagement members 1306 of the grabber 1212.

This non-frictional engagement of the grabber element 1212 with the flow diverter 300 eases the deployment of the flow diverter 300. Specifically, as the grabber element 1212 does not compress the flow diverter 300 into the interior wall 504 of the lumen 502, the friction forces between the flow diverter 300 and the interior wall 504 of the lumen 502 are minimized. This minimization of the friction forces between the interior wall 504 of the lumen 502 and the flow diverter 300 also decreases the force applied to the core wire 112 to move the flow diverter 300 within the lumen 502 of the catheter 104 and/or of the introducer sheath 120, which eases deployment of the flow diverter 300 from the catheter 104 and/or movement of the flow diverter 300 with respect to the introducer sheath 120.

In some embodiments, and as shown in FIG. 14, the grabber 1212 can be located at the distal end 1208 of the elongate body 1204. Alternatively, in some embodiments, the grabber 1212 can be located at an intermediate position along the elongate body 1204, which intermediate position can be between the proximal end 1206 and the distal end 1208 of the elongate body 1204.

The system 1200 can further include a support coil 510. The support coil 510 can extend along and/or around at least a portion of the distal portion 116 of the core wire 112. As previously discussed, this distal portion 116 can have a taper to increase the flexibility of the distal portion 116 of the core wire 112. The support coil 510 can prevent the core wire 112, and specifically prevent the tapered distal portion 116 of the core wire from buckling under compressive loads such as when the core wire 112 is distally advanced to deploy the flow diverter 300.

The support coil 510 can, in some embodiments, extend from a location proximal to the pusher 505 to the pusher 505, and can extend distally beyond the pusher 505. In some embodiments, the support coil 510 can extend around and/or along at least part of the distal portion 116 of the core wire 112, including, along and/or around the distal end 113 of the core wire 112. In some embodiments, the support coil 510 can extend across the junction 1210 and along and/or around at least a part of the elongate body 1204. In some embodiments, the support coil 510 can extend along and/or around the elongate body 1204 up to the claw 1212.

In some embodiments, the system 1200 can include a friction bump 508 coupled to the core wire 112. The friction bump 508 can, in some embodiments, be radiopaque, or include a radiopaque element such as a wire coil. The friction bump 508 can, in some embodiments, be included instead of the pusher 505, or can be included in addition to the pusher 505. In the event that the friction bump 508 is included in addition to the pusher 505, the friction bump 508 can be coupled to the core wire 112 at a position distal of the pusher 505. In embodiments in which the friction bump 508 replaces the pusher 505, the friction bump 508 can be positioned such that both the friction bump 508 and the claw mechanism 1202 can simultaneously engage with the flow diverter 300. In some embodiments, the friction bump 508 can be located at the junction 1210.

Figure 15:
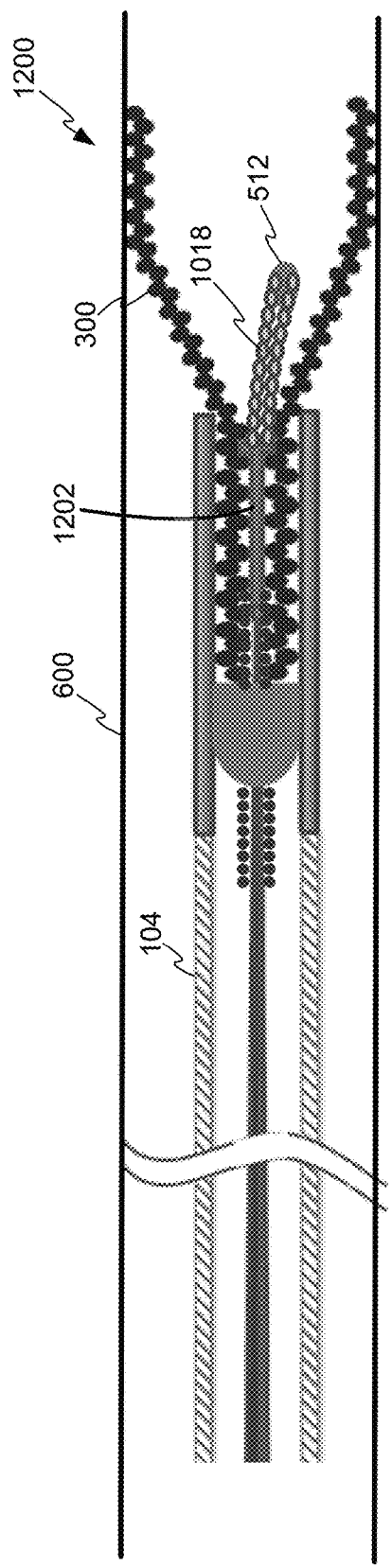
FIG. 15 is a depiction of a fourth delivery system in a first partially deployed configuration.

In some embodiments, and as seen in FIGS. 14 and 15, the system 1200 can include a tip coil 1018, which tip coil 1018 can be a flexible tip coil 1018. The tip coil 1018 can distally extend from claw mechanism 1202, and specifically from the distal end 1208 of the claw mechanism 1202. The tip coil 1018 can terminate in an atraumatic tip 512. The atraumatic tip 512 can, in some embodiments, be at the distal most point of the tip coil 1018. In some embodiments, the flexible tip coil 1018 and/or the flexible tip coil 1018 and the atraumatic tip 512 can facilitate in navigating the system 1200 and/or the core wire 112 through the vasculature, and specifically through tortuous vasculature.

In some embodiments, the flexible tip coil 1018 can support the flow diverter 300. Specifically, the flexible tip coil 1018 can extend through at least a portion of the length of the flow diverter 300 and can, in some embodiments, strengthen those portions of the flow diverter 300. Specifically, and in some embodiments, the flexible tip coil 1018 can prevent the flow diverter from collapsing and/or buckling.

As seen in FIG. 15, the flow diverter 300 is partially deployed from the catheter 104. The flow diverter 300 has been partially deployed from the catheter 104 by distally moving the core wire 112, and thus the flow diverter 300 relative to the catheter 104. In some embodiments, this relative movement can be achieved by, for example, holding the position of the catheter 104 and distally advancing the core wire 112 and thus the flow diverter 300. In some embodiments, this relative movement can be achieved by, for example, holding the position of the core wire 112 and proximally retracting the catheter 104. In some embodiments, the relative movement can be achieved by a combination of both movement of the core wire 112 and the catheter 104 to achieve the relative distal advance of the core wire 112 and the flow diverter 300 with respect to the catheter 104.

Figure 16:
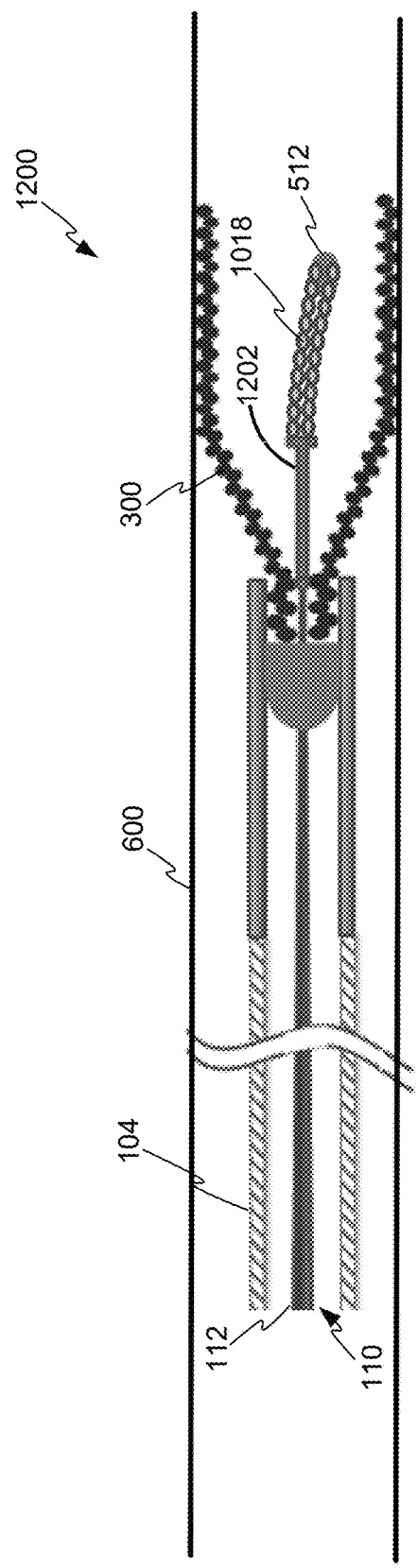
FIG. 16 is a depiction of a fourth delivery system is a second partially deployed configuration.

As seen in FIG. 16, this relative distal advance of the core wire 112 and the flow diverter 300 with respect to the catheter 104 can ultimately lead to the claw mechanism 1202 exiting the catheter 104. As the claw mechanism 1202, and the portions of the flow diverter 300 to which the claw mechanism 1202 is engaged, exits the catheter 104, the flow diverter 300 expands and disengages with the claw mechanism 1202. Further advance of the core wire 112 relative to the catheter 104 results in the complete deployment of the flow diverter 300, at which point the catheter 104 and/or the core wire 112 can be retracted from the blood vessel 600.

Figure 17:
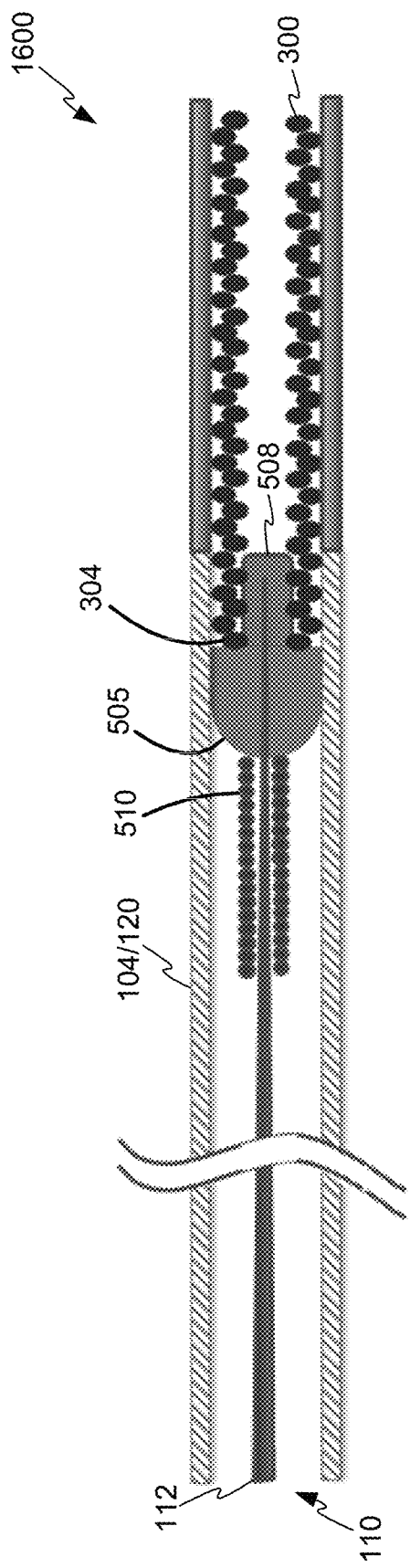
FIG. 17 is a depiction of a fifth delivery system.

With reference now to FIG. 17 a schematic depiction of a fifth delivery system 1600 is shown. This system 1600 is a shortened delivery system that terminates in the proximal end 402 of the flow diverter 300. This shortened delivery system provides advantages over other delivery embodiments as the distance that the delivery system 1600 extends into the neurovasculature is decreased, thereby increasing the ability to treat smaller, and further distal vasculature.

In some embodiments, for example, the flow diverter 300 significantly shortens as it is deployed. Due to this shortening of the flow diverter 300, the core wire 112 is advanced significantly further than the length of the deployed flow diverter 300. Because of this, the core wire 112, and specifically the distal end 113 of the core wire 112 can extend beyond the flow diverter 300 into the blood vessel. Pushing the core wire 112 into the blood vessel 600 distally beyond the flow diverter 300 can result in significant problems. These problems can especially arise in the neurovasculature where blood vessels tend to be smaller and more tortuous. In such an environment, the portion of the core wire 112 extending distally beyond the flow diverter 300 can damage, or even pierce the wall of the blood vessel 600. This risk can be mitigated by, for example, the inclusion of a tip coil 1018. The embodiment of FIGS. 16 through 18 mitigates these risks with a shortened delivery system, that in some embodiments, does not extend beyond the deployed flow diverter 300.

Specifically, a flow diverter 300 in the constrained configuration within the catheter 104 is frequently multiple times longer than that same flow diverter 300 in an unconstrained and expanded configuration. Due to the shortening of the flow diverter 300 resulting from deployment of the flow diverter 300, distally extending portions of the deployment wire 110 can easily end up extending distally beyond the distal end 404 of the flow diverter 300. This can be particularly problematic with small and tortuous vessels as that portion extending distally beyond the flow diverter 300 may damage the blood vessel 600, and in extreme circumstances, may penetrate the wall of that blood vessel 600.

Figure 18:
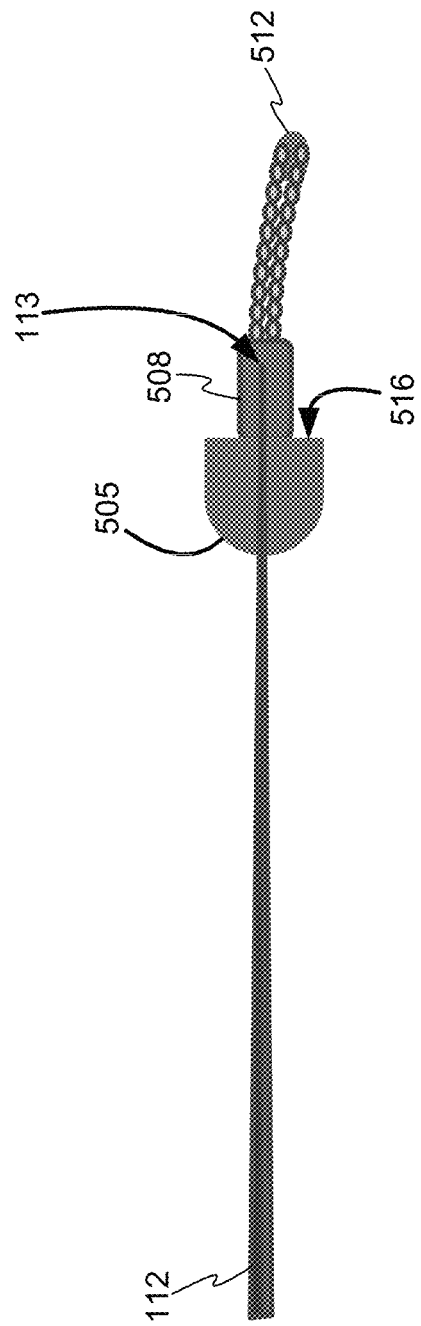
FIG. 18 is a depiction of the deployment features of the fifth delivery system.

As seen in FIG. 18, the friction bump 508 abuts the pusher 505 and covers the distal end 113 of the core wire 112, and as seen in FIG. 17, the friction bump 508 remains wholly within the proximal end 402 of the flow diverter 300. Thus, during a deployment, neither the friction bump 508 nor the deployment wire 110 extends distally beyond the distal end 404 of the deployed flow diverter 300.

The system 1600 can include a flow diverter 300 that can be held in a constrained configuration within the lumen 502 of the catheter 104 and/or of an introducer sheath 120. The deployment wire 110 can extend at least partially into both the flow diverter 300 and the lumen 502 of the catheter 104 or of the introducer sheath 120. The deployment wire 110, can include the core wire 112 which can extend into the lumen 502 of the catheter 104 and/or of the introducer sheath 120, and the deployment features 118, which are shown wholly within the lumen 502 of the catheter 104 and/or of the introducer sheath 120. As seen in FIG. 17, these deployment features are coupled to the flow diverter such that movement of the deployment wire 110 and/or of the core wire 112 with respect to the catheter 104 and/or the introducer sheath 120 likewise moves the flow diverter 300 relative to the catheter 104 and/or the introducer sheath 120.

The deployment features 118 include a pusher 505 and a friction bump 508. The friction bump 508 and the pusher 505 shown in FIG. 17 are engaged with the flow diverter 300 such that a movement of the core wire 112 relative to the catheter 104 and/or the introducer sheath 120 likewise moves the flow diverter 300 relative to the catheter 104 and/or to the introducer sheath 120.

The pusher 505 can be, for example, a pusher coil 506. The pusher 505 can extend around and/or along a part of the distal portion 116 of the core wire 112. In some embodiments, the pusher 505 can include a distal end 516 that can engage with a first end 304 of the flow diverter 300, and, as shown in FIG. 17, is engaged with a first end 304 of the flow diverter 300. The pusher 505 can be coupled to the core wire 112. Specifically, the pusher 505 can be coupled to the core wire 112 proximal of the distal end 113 of the core wire 112 such that the core wire 112 extends distally beyond the pusher 505.

The friction bump 508 can be coupled to the deployment wire 110, and specifically can be coupled to the core wire 112. The friction bump 508 can, in some embodiments, be radiopaque, or include a radiopaque element such as a wire coil. The friction bump 508 can comprise a single friction bump 508 that can be a cylindrical friction bump 508. In some embodiments, and as shown in FIG. 18, the friction bump 508 can cover the distal end 113 of the deployment wire 110, and specifically can cover the distal end 113 of the core wire 112. In some embodiments, the friction bump 508 abuts the pusher 505, and specifically, in some embodiments, a proximal end of the friction bump 508 abuts the distal end 516 of the pusher 505.

Figure 19:
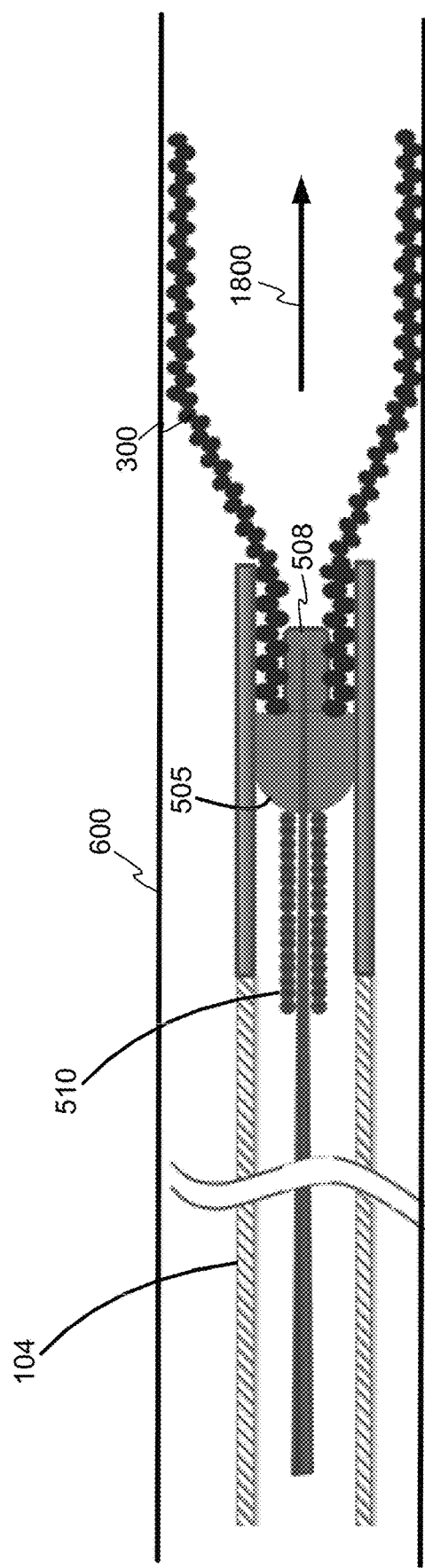
FIG. 19 is a depiction of a fifth delivery system in a partially deployed configuration.

An embodiment of the deployment of the flow diverter with the system 1600 is shown in FIG. 19. As seen in that figure, the deployment wire 110 and the flow diverter 300 are distally advanced in the direction indicated by arrow 1800 until the flow diverter 300 exits the catheter 104. As the flow diverter 300 exits the catheter 104, the flow diverter 300 can begin to expand and can begin to engage the interior of the blood vessel 600. In some embodiments, the distal advance of the deployment wire 110 and the flow diverter 300 can continue until the flow diverter 300 is fully deployed. Alternatively, if the flow diverter 300 has not been fully deployed from the catheter 104, the flow diverter 300 can be retracted and/or partially retracted into the catheter 104. Due to the position of the friction bump 508 at the distal end 113 of the core wire 112, the friction bump 508 remains engaged with the flow diverter 300 until the flow diverter 300 leaves the catheter 104 and is fully deployed. Due to this, the flow diverter 300 remains retractable as long as a last portion of the flow diverter 300 remains in the catheter 105, or in other words, until immediately before the flow diverter 300 is fully deployed. Thus, the use of the friction bump 508 as shown in the system 1600 can provide a high degree of flexibility and control of the deployment of the flow diverter 300.

Figure 20:
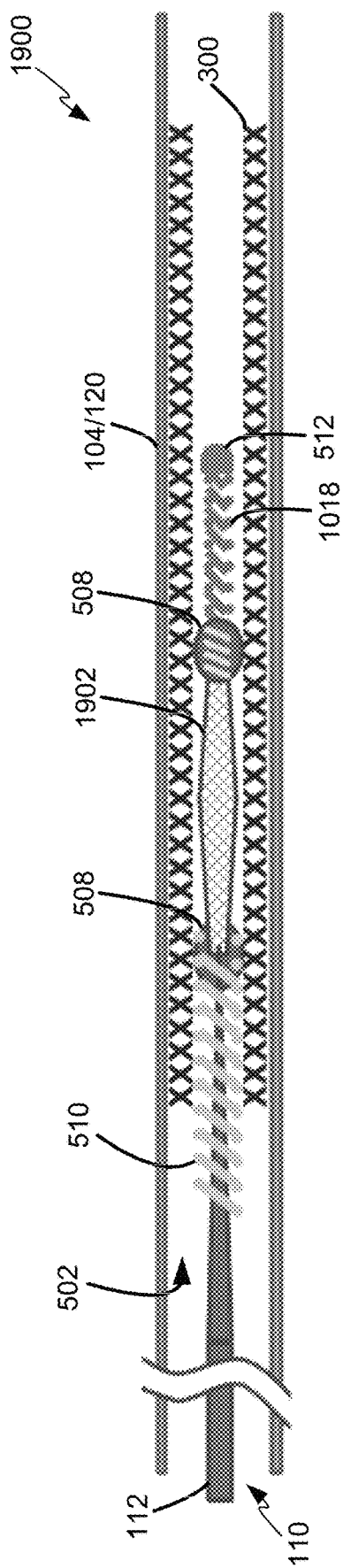
FIG. 20 is a depiction of one embodiment of an active delivery system.

With reference now to FIG. 20, a schematic depiction of one embodiment of a dynamic delivery system 1900 is shown. The system 1900 can include a flow diverter 300 that can be held in a constrained state within the lumen 502 of the catheter 104 and/or of an introducer sheath 120. In some embodiments, the flow diverter 300 can comprise an expandable, braided member that can define a flow channel 406. In some embodiments, the flow diverter 300 can comprise a self-expanding braided member.

The flow diverter 300 can be positioned in a lumen 502 of the catheter 104 and/or of the introducer sheath 120. In some embodiments, the flow diverter 300 can be positioned in a lumen 502 of the catheter 104 and/or of the introducer sheath 120 circumferentially between the interior wall 504 defining the lumen 502 of the catheter 104 and/or of the introducer sheath 120 and the expanding element, which can be a self-expanding element, discussed at greater length below.

The deployment wire 110 can extend at least partially into both the flow diverter 300 and the lumen 502 of the catheter 104 or of the introducer sheath 120. The deployment wire 110, can include the core wire 112 which can extend into the lumen 502 of the catheter 104 and/or of the introducer sheath 120, and the deployment features 118, which are shown wholly within the lumen 502 of the catheter 104 and/or of the introducer sheath 120. As seen in FIG. 20 these deployment features 118 are coupled to the flow diverter such that movement of the deployment wire 110 and/or of the core wire 112 with respect to the catheter 104 and/or the introducer sheath 120 likewise moves the flow diverter 300 relative to the catheter 104 and/or the introducer sheath 120.

The deployment features 118 include one or more friction bumps 508, the supporting coil 510, an expanding element 1901, a tip coil 1018, and an atraumatic tip 512. The tip coil can be a flexible tip coil 1018. In some embodiments, the flexible tip coil 1018 and/or the flexible tip coil 1018 and the atraumatic tip 512 can facilitate in navigating the system 1200 and/or the core wire 112 through the vasculature, and specifically through tortuous vasculature.

In some embodiments, some or all of these deployment features 118 engage with, or as shown in FIG. 20, are engaged with the flow diverter 300. The deployment features 118 are engage and/or can be engaged with the flow diverter 300 such that movement of the core wire 112 results in corresponding movement of the flow diverter 300.

The expanding element 1901 can comprise a self-expanding element 1902 or a controlled expanding element. In some embodiments, the self-expanding element 1902 can expand upon exiting the catheter 104. In some embodiments, the controlled expanding element can expand when controlled to expand. The controlled expanding element can comprise, for example, a stent, a braid, a balloon, or the like. In some embodiments in which the expanding element 1902 comprises a braided member, the thickness of the stands of the braid can be varied to achieve a desired effect. For example, the strands can be thicker to provide increased expansion force, or the stands can be thinner to provide increased flexibility. In some embodiments, the strands can comprise a variety of material including, for example, DFT, which can be, for example, radiopaque. In some embodiments, the strands can comprise a polymer such as a high tensile strength polymer. In some embodiments, a polymer used in the strands can advantageously increase friction between the expanding element 1902 and the flow diverter 300, thereby increasing the ability of the expanding element 1902 to retract the flow diverter 300. In embodiments in which the stands comprise a polymer, that polymer can be treated and/or doped to be radiopaque.

In some embodiments, the materials of the flow diverter 300 and/or the expanding element 1902 can be selected to minimize a compressed diameter of the flow diverter 300 around the expanding element 1902. In some embodiments, for example, the selection and use of a high tensile strength material, such as a material having a tensile strength at or above 100 kpsi, 150 kpsi, 200 kpsi, 250 kpsi, or the like, the fully compressed expanding element 1902 can have an outer diameter, for example, between approximately 0.005 inches and 0.035 inches, between approximately 0.01 inches and 0.015 inches, of approximately 0.013 inches, or any other or intermediate outer diameter. In such an embodiment, when the flow diverter 300 is axially positioned around and over the expanding element 1902, the combination of the expanding element 1902 and the flow diverter 300, both in a compressed state can have an outer diameter of between, for example, approximately 0.01 inches 0.04 inches, between approximately 0.015 inches and 0.035 inches, an outer diameter of approximately 0.017 inches, or any other or intermediate outer diameter. As used herein, "approximately" indicates values falling within: +/−5% of the associated value, +/−10% of the associated value, and/or +/−20% of the associated value. Thus, the combination of the flow diverter 300 and the expanding element 1902 can fit in a catheter 104 having an inner diameter between, for example, approximately 0.01 inches and 0.04 inches, between approximately 0.015 inches and 0.035 inches, of approximately 0.017 inches, or any other or intermediate inner diameter.

In some embodiments, the controlled expanding element can include one or several features configured to enable control of the expansion of the controlled expanding element. These features can include one or several wires, catheters, rods, or the like. In some embodiments, the controlled expanding element can be expanded by bring axially compressing the controlled expanding element such that a proximal end of the controlled expanding element is brought closer to a distal end of the controlled expanding element. While the following discussion focuses on use of the self-expanding element 1902, it will be appreciated that the self-expanding element 1902 can be replaced with the controlled expanding element.

Figure 21:
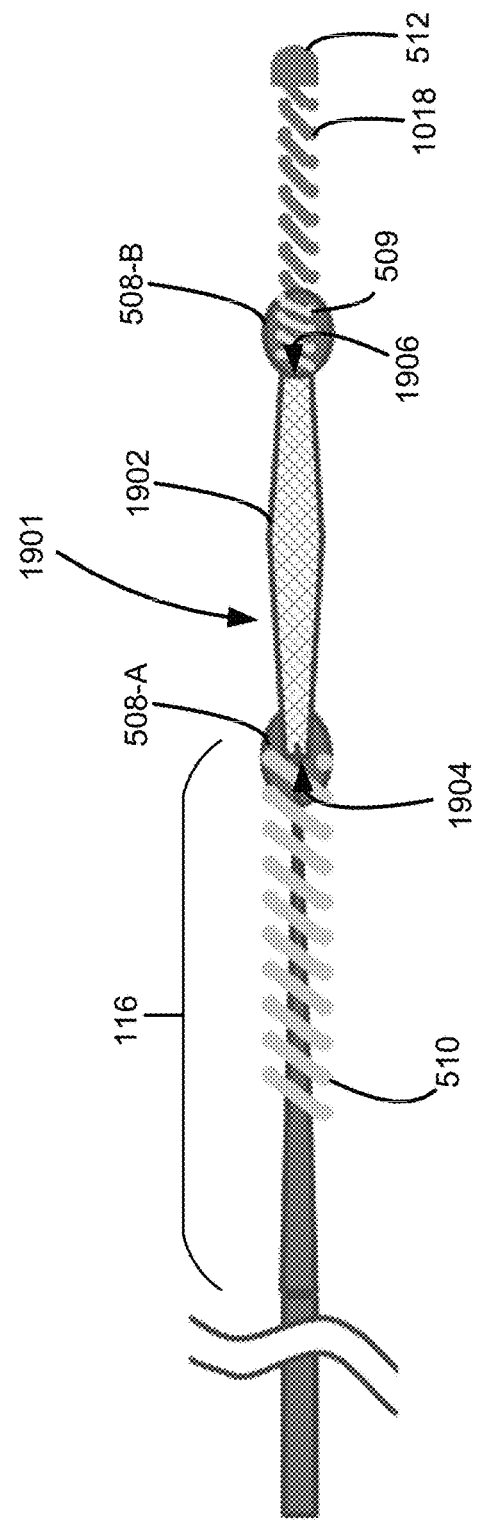
FIG. 21 is a depiction of one embodiment of deployment features of the active delivery system.

As shown in FIG. 21, the self-expanding element 1902 comprises a proximal end 1904, also referred to herein as a first end 1904, and a distal end 1906, also referred to herein as a second end 1906. The proximal end 1904 of the self-expanding element 1902 can be coupled to the distal end 113 of the deployment wire 110, and more specifically to the distal end 113 of the core wire 112. The self-expanding element 1902 can, as shown in FIG. 21, distally extend from the proximal end 1904 to the distal end 1906 of the self-expanding element 1902.

The self-expanding element 1902 can comprise a stent or a braided member. In some embodiments, the self-expanding element comprises a laser cut stent. The self-expanding element 1902 can comprise a variety of shapes and sizes, and can be made from a variety of materials. In some embodiments, the self-expanding element 1902 can be made from Nitinol, a drawn filled tube which can comprise, for example, Nitinol, a cobalt chromium exterior and a platinum interior, a mixture of, for example, Nitinol and cobalt chromium, or the like. In some embodiments, the self-expanding element 1902 can comprise a plurality of braided strands, at least some of which can be radiopaque.

The self-expanding member 1902 can be configured to engage with the flow diverter 300 when the flow diverter is contained within the catheter 104 and/or in the introducer sheath 120 such that movement of the deployment wire 110, and specifically of the core wire 112, results in corresponding movement of the flow diverter 300. When the self-expanding element 1902 has deployed from the catheter 104, the self-expanding element 1902 expands to a fully expanded state, or to a maximum expanded state allowed by the blood vessel in which the self-expanding element 1902 is contained. In some embodiments, the self-expanding element 1902 can be distally advanced and/or proximally retracted through the flow diverter 300.

In some embodiments, the expanding element 1902, such as the controlled expanding element or the self-expanding element 1902 can generate radial forces which can expand the flow diverter 300 to a greater degree than would otherwise occur. For example, even if the flow diverter 300 is self-expanding, the expanding element 1901 such as the controlled expanding element or the self-expanding element 1902 may generate greater radial, expansive forces than generated by the flow diverter 300. By moving the expanding element 1901 through the flow diverter 300, these greater radial, expansive forces generated by the expanding element 1901 can be applied to the flow diverter 300 and can further expand the flow diverter 300. This increased expansion can increase and/or improve the contact between the flow diverter 300 and the blood vessel 600. In some embodiments, the use of an expanding element 1901 such as the controlled expanding element or as the self-expanding element.

In some embodiments, the expanding element 1902, when unconstrained, can have a diameter greater than a diameter of the unconstrained flow diverter 300, and in some embodiments, the expanding element 1902, when unconstrained, can have a diameter less than a diameter of the unconstrained flow diverter 300. Thus, in some embodiments, and when unconstrained, the expanding element 1902 can have a diameter greater than, or less than the diameter of the blood vessel 600. In some embodiments, when deploying a flow diverter 300, kinks, twists, compression, or bends can occur in the flow diverter 300, which can prevent the expansion of the flow diverter 300. In some embodiments, the expanding element 1902 can straighten, remedy, and/or eliminate these kinks, twists, compression, or bends in the flow diverter 300 by expanding to a diameter less than the diameter of the blood vessel 600. In such an embodiment, an expansion by the expanding element 1902 of less than the diameter of the blood vessel 600 can straighten, remedy, and/or eliminate these kinks, twists, compression, or bends in the flow diverter 300, which can result in the flow diverter 300 self-expanding to engage with the wall of the blood vessel 600. Thus, in some embodiments, the expanding element 1902 initiates expansion, which is then continued and completed by the flow diverter 300.

In some embodiments, the expansion of the expanding element 1902 can result in the shortening of the expanding element 1902. This shortening can move the distal end 113 of the core wire 112 proximally. This can specifically move the atraumatic tip 512 proximally. This proximal movement of the distal end 113 of the core wire 112 and/or of the atraumatic tip 512 can decrease the distal extension of those portions of the core wire 112 into the blood vessel, thereby decreasing the risk of damage to the blood vessel.

The one or more friction bump 508 can be coupled to the deployment wire 110, and specifically can be coupled to the core wire 112. In some embodiments, the one or more friction bumps 508 can be directly coupled to the deployment wire 110 and specifically to the core wire 112, and in some embodiments, the one or more friction bumps 508 can be indirectly coupled to the deployment wire 110 and specifically to the core wire 112 via, for example, the self-expanding element.

In some embodiments, one or more friction bumps 508 can be located at one or both of the ends of the self-expanding element. Thus, in some embodiments, at least one of the friction bumps 508 is located at one of the proximal end 1904 and the distal end 1906. In some embodiments, at least one of the friction bumps 508 is located at one of the proximal end 1904 and the distal end 1906, and another of the friction bumps is located at the other of the proximal end 1904 and the distal end 1906. As seen in FIG. 21, the friction bumps 508 include a first friction bump 508-A located at, adjacent to, and/or on the proximal end 1904 of the self-expanding element 1902, and a second friction bump 508-B located at, adjacent to, and/or on the distal end 1906 of the self-expanding element 1902. In some embodiments, the friction bump 508 can extend across and/or over a portion of the self-expanding element 1902. In some embodiments, one or more of the friction bumps 508 can be radiopaque, and/or can include a radiopaque element such as a wire coil 509.

The system can include a support coil 510. The support coil 510 can extend around and/or along at least part of the distal portion 116 of the core wire 112, including, along and/or around the distal end 113 of the core wire 112. The support coil 510 can, in some embodiments, extend from a location proximal of the self-expanding element 1902 to the self-expanding element 1902, and/or from a location proximal to the first friction bump 508-A to the first friction bump 508-A. In some embodiments, the support coil 510 can extend at least partially into the first friction bump 508-A.

The system 1900 can, in some embodiments, include a tip coil 1018, which can be a flexible tip coil 1018. The tip coil 1018 can distally extend from the self-expanding element 1902, and specifically can distally extend from the distal end 1906 of the self-expanding element 1902. The tip coil 1018 can extend distally beyond the self-expanding element 1902 and can terminate in an atraumatic tip 512. The atraumatic tip 512 can, in some embodiments, be at the distal most point of the tip coil 1018. In some embodiments, the flexible tip coil 1018 and/or the flexible tip coil 1018 and the atraumatic tip 512 can facilitate in navigating the system 1200 and/or the core wire 112 through the vasculature, and specifically through tortuous vasculature.

Figure 22:
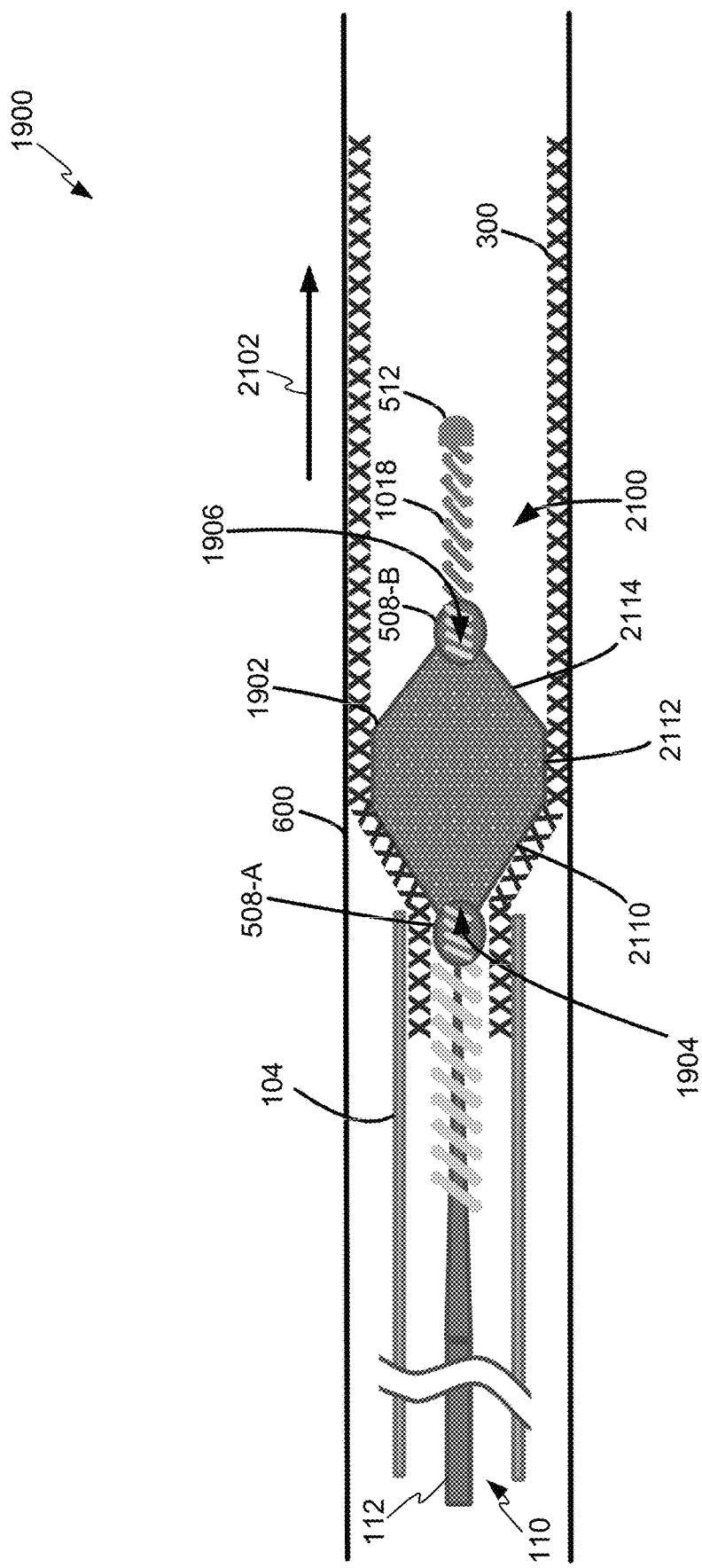
FIG. 22 is a depiction of one embodiment of the active delivery system in a partially deployed configuration.

An embodiment of the deployment of the flow diverter with the system 1900 is shown in FIG. 22. In FIG. 22, the self-expanding member 1902 is shown in a deployed configuration. In some embodiments, the self-expanding member 1902 can comprise a variety of shapes and sizes. In the embodiment shown in FIG. 22, the self-expanding member 1902 includes the proximal end 1904 and the distal end 1906. The self-expanding member 1902 further include a proximal portion 2110 and a distal portion 2114. In some embodiments, intermediate between the proximal portion 2110 and the distal portion 2114 can be an intermediate portion 2112 linking the proximal portion 2110 and the distal portion 2114. In some embodiments, and as shown in FIG. 22, the proximal portion 2110 can distally extend from the proximal end 1904 to the intermediate portion 2112, and the distal portion 2114 can proximally extend from the distal end 1906 to the intermediate portion 2112.

In some embodiments, the proximal portion 2110, in the expanded configuration, can have a progressively increasing diameter as the distance from the proximal end 1904 increases. In some embodiments, the intermediate portion 2112 can have a constant diameter. In some embodiments, the distal portion 2114 can have a progressively decreasing diameter as the distance from the proximal end 1904 increases. In some embodiments, each of the different portions 2110, 2112, 2114 of the self-expanding member 1902 can be configured to engage with the flow diverter 300 to expand and/or to further expand the flow diverter 300.

In some embodiments, and during deployment of the flow diverter 300, the self-expanding member 1902 can intermittently contact the flow diverter 300, and specifically the inner wall 303 of the flow diverter 300 to cause expansion of the flow diverter 300. For example, in some embodiments, portions of the flow diverter 300 may not fully expand, whereas other portions of the flow diverter 300 may fully expand. For example, in embodiments in which a flow diverter 300 extends around a corner of a blood vessel, the portion of the flow diverter 300 that is bending may not fully deploy. In such an embodiment, the self-expanding member 1902 may intermittently contact the flow diverter 300, and specifically may contact the portions of the flow diverter 300 that have not fully deployed. Via this intermittent contact, portions of the flow diverter 300 that have not fully deployed can be deployed by the self-expanding member 1902. In some embodiments, this intermittent contact can occur along one or more of the proximal portion 2110, the intermediate portion 2112, and/or the distal portion 2114 of the self-expanding member 1902. In the embodiment of FIG. 22, contact is occurring between the flow diverter 300 and the self-expanding member 1902 along the proximal portion 2110 and the intermediate portion 2112.

In some embodiments, and during deployment of the flow diverter 300, the self-expanding member 1902 can intimately contact the flow diverter 300, and specifically the inner wall 303 of the flow diverter 300 to cause expansion of the flow diverter. In some embodiments, this intimate contact can cause the flow diverter 300 to fully deploy and/or more fully deploy. In some embodiments, this intimate contact can occur along all or portions of the flow diverter 300. In some embodiments, the intimate contact between the flow diverter 300 and the self-expanding member 1902 can occur along one or more of the proximal portion 2110, the intermediate portion 2112, and/or the distal portion 2114 of the self-expanding member 1902.

As shown in FIG. 22, the catheter 104 has been inserted into the vascular system and has been advanced to a location proximate to a treatment site 2100, which location can be at, near, or beyond the treatment site 2100. In some embodiments, the position of the catheter can be determined via imaging, such as via fluoroscopy.

As seen in that figure, the deployment wire 110 and the flow diverter 300 are distally advanced in the direction indicated by arrow 2102 until the flow diverter 300 exits the catheter 104. As the flow diverter 300 exits the catheter 104, the flow diverter 300 can begin to expand and can begin to engage the interior of the blood vessel 600. In some embodiments, the distal advance of the deployment wire 110 and the flow diverter 300 can continue until the flow diverter 300 is fully deployed. Alternatively, if the flow diverter 300 has not been fully deployed from the catheter 104, the flow diverter 300 can be retracted and/or partially retracted into the catheter 104. In some embodiments, the flow diverter 300 can be retracted and/or partially retracted into the catheter 104 until the proximal most of the friction bumps 508 and/or the self-expanding element 1902 exits the catheter 104. In some embodiments, the position of the flow diverter 300, of the catheter 104, of the friction bumps 508 and/or the self-expanding element 1902 can be determined via imaging, and specifically via imaging of radiopaque elements and/or portions of the catheter 104, of the friction bumps 508, and/or the self-expanding element 1902. In some embodiments, and based on the results of this imaging, it can be determined if the flow diverter 300 can be retracted and/or partially retracted into the catheter 104.

When the self-expanding element 1902 exits the catheter 104, the self-expanding element 1902 expands and applies radially outward forces to the flow diverter 300 causing the flow diverter 300 to further expand. Alternatively, in the event that a controlled expanding element is being used, open exiting the catheter 104, the controlled expanding element can be expanded.

The self-expanding element 1902 can continue to be distally advanced relative to the catheter 104 until the flow diverter 300 is fully deployed. When the flow diverter 300 is fully deployed, the self-expanding element 1902 can be distally advanced through the flow diverter 300 to fully and/or maximally expand the flow diverter 300, at which point the self-expanding element 1902 can be proximally retracted through the flow diverter 300 and then back into the catheter 104. In some embodiments, the distal advance and the proximal retraction of the expanding element 1902 through the flow diverter 300 can be repeated multiple times before retracting the expanding element 1902 into the catheter 104. In some embodiments, the repeated movement of the expanding element 1902 through the deployed flow diverter 300 can facilitate in achieving full deployment of the flow diverter 300, specifically in the event that all or portions of the flow diverter 300 have not fully deployed. This movement of the self-expanding element 1902, first distally and then proximally through the flow diverter 300 can increase the expansion of the flow diverter 300 and improve the connection between the flow diverter and the blood vessel 600.

Once the self-expanding element 1902 has been retracted into the catheter 104, the catheter can be retracted and/or one or several additional flow diverters can be delivered to the treatment site.

With reference now to FIGS. 22 through 30, a graphical depiction of an embodiment of delivering a flow diverter 300, and specifically for delivery a flow diverter 300 into a blood vessel 600 to treat an aneurysm is shown. In some embodiments, the blood vessel can be a neurovascular blood vessel, or in other words, can be a blood vessel in or around the patient's brain. In some embodiments, the delivery of the flow diverter 300 into the blood vessel 600 can include the partial deployment of the flow diverter 300 from a catheter 104, and/or the full or partial retraction of the flow diverter 300 into the catheter 104. As used herein, a full retraction occurs when the flow diverter 300 is retracted until it is completely contained with the catheter 104, and a partial retraction occurs when a portion of the flow diverter 300 remains exterior to the catheter 104 after retraction of the flow diverter 300.

In some embodiments, the flow diverter can be fully or partially deployed subsequent to the retraction of the flow diverter 300 into the catheter 104. In some embodiments, the flow diverter 300 can be partially deployed and retracted once, and in some embodiments, the flow diverter 300 can be repeatedly partially deployed and retracted into the catheter 104.

The flow diverter 300 can be fully or partially retracted for a number of reasons. In some embodiments, for example, the flow diverter 300 can be fully or partially retracted into the catheter 104 to facilitate repositioning of the flow diverter 300 with respect to the treatment location. In some embodiments, the flow diverter 300 can be retracted into the catheter 104 and removed from the blood vessel. In some embodiments, the flow diverter 300 can be replaced with another flow diverter 300 of a different size, such as, for example, a flow diverter having a larger or a smaller diameter. In some embodiments, the flow diverter 300 can be retracted and redeployed to improve expansion of the flow diverter 300. In some embodiments, for example, a retracting and redeploying the flow diverter 300 can result in a more complete opening of the flow diverter 300, and/or improved contact between all or portions of the flow diverter 300 and the blood vessel in which it is deployed.

In some embodiments, the flow diverter 300 can be retracted and/or redeployed to affect the portion of the blood vessel covered by the deployed flow diverter 300. In some embodiments, for example, and by controlling a position and/or movement of both the catheter 104 and the core wire 112 during deployment, the coverage of the flow diverter 300 of the blood vessel in the treatment location can be affected. For example, and after a distal portion of the flow diverter 300 has engaged with the blood vessel, thereby coupling the flow diverter 300 to the blood vessel, the length of the deployed flow diverter can be affected by retracting the catheter 104 while deploying the flow diverter 300. Specifically, the relative speed of the retraction of the catheter 104 with respect to the deployment of the flow diverter 300 can affect the length of the flow diverter 300.

For example, by retracting the catheter 104 relatively slowly with respect to the deployment of the flow diverter 300, the length of the deployed flow diverter can be decreased. Alternatively, by retracting the catheter 104 relatively quickly with respect to the deployment of the flow diverter 300, the flow diverter 300 can be stretched while being deployed and the length of the deployed flow diverter 300 can be increased.

In some embodiments, and by controlling the length of the deployed flow diverter 300, the surgeon can affect the diameter of the deployed flow diverter 300. Specifically, as the length of the deployed flow diverter increases, the deployed, unconstrained diameter of the flow diverter decreases. Thus, in some embodiments in which a flow diverter 300 is deployed into a blood vessel having a larger diameter, the surgeon may decrease the length of the deployed flow diverter to achieve the desired deployed diameter of the flow diverter 300.

Figure 23:
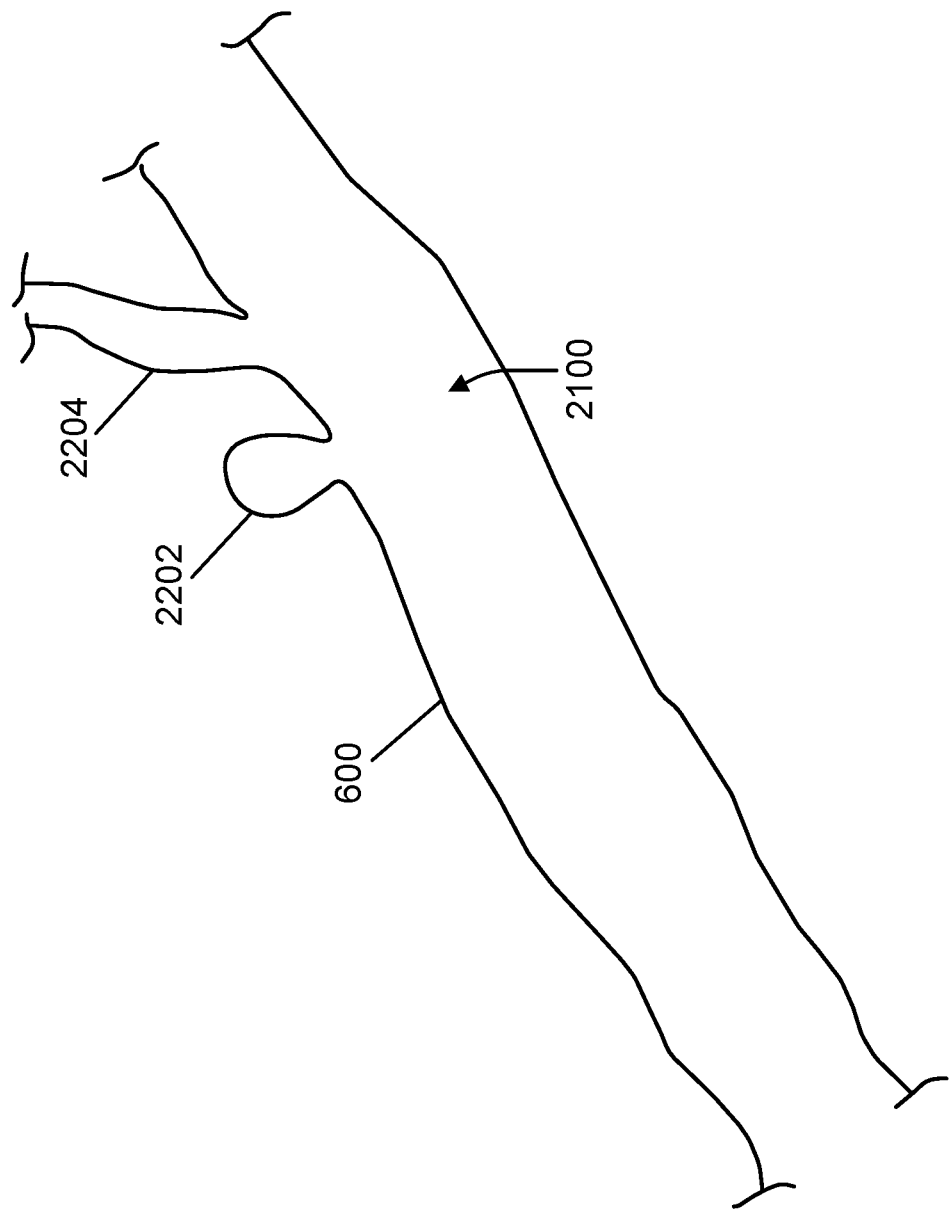
FIG. 23 is a depiction of a treatment site.

The process begins at FIG. 23, wherein a treatment location 2100 is identified. As seen in FIG. 23, this treatment location is in a blood vessel and includes an aneurysm 2202 or other structure to be covered or partially covered by a flow diverter 300. In some embodiments the treatment location 2100 can be adjacent one or several structures to not be covered by the flow diverter 300 such as, for example, one or several branches 2204 of the vessel 600.

Figure 24:
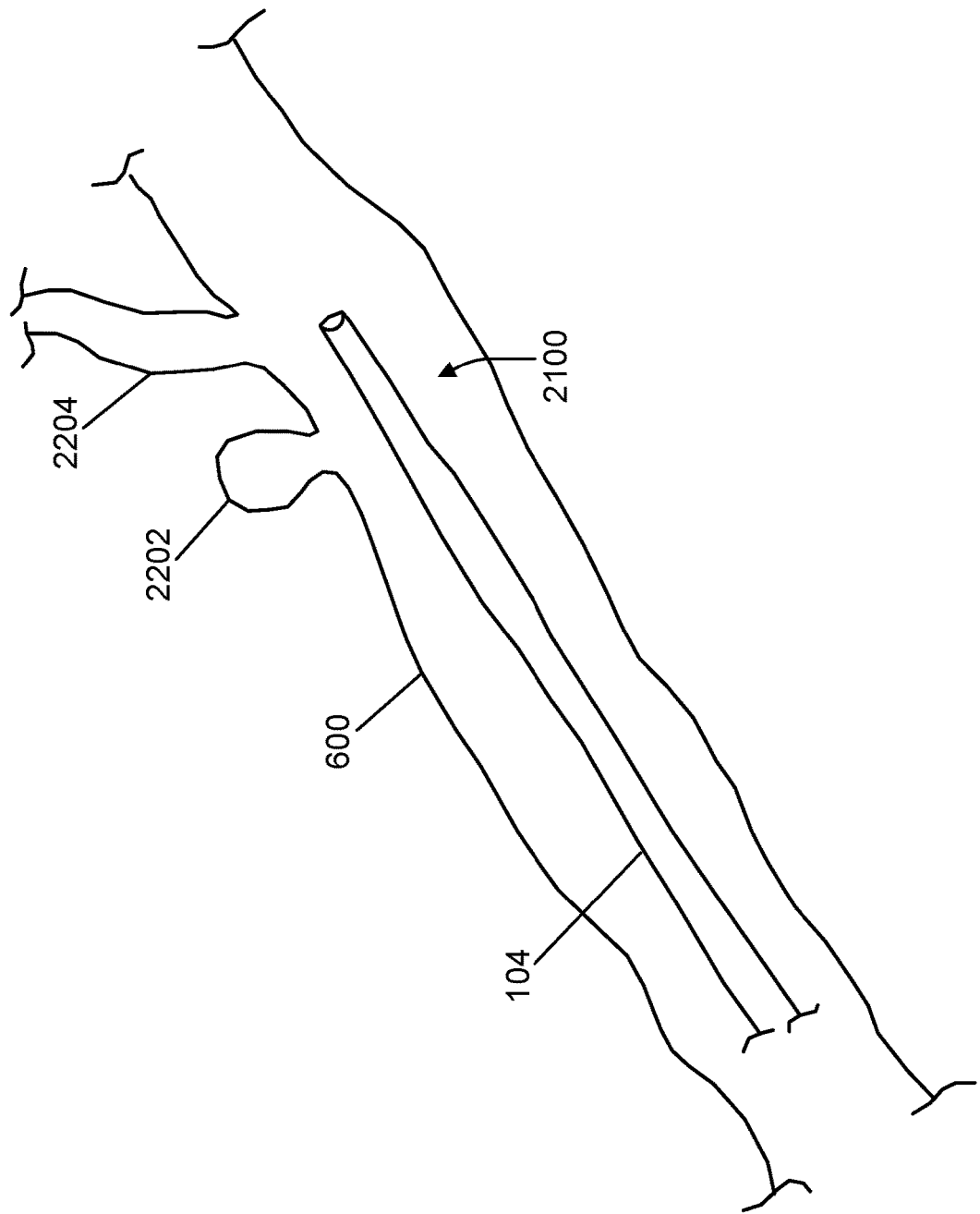
FIG. 24 is a depiction of a catheter at a first position with respect to the treatment site.

After the treatment location 2100 has been identified, a catheter 104, which can be a microcatheter 104 can be inserted into the patient's vasculature via an access point, and the catheter 104 can be advanced in the patient's vasculature until the catheter 104, and specifically until a distal end 132 of the catheter 104 is proximate to the treatment site 2100, or in other words, is at, near, or beyond the treatment location as shown in FIG. 24. In some embodiments, the insertion of the catheter 104 into the patient's vasculature and the location of the catheter 104, and specifically of the distal tip 132 of the catheter 104 in the patient's vasculature can be monitored via imaging.

The flow diverter 300 can be loaded into the lumen 502 of the catheter 104. In some embodiments, this can be performed before the catheter 104 is inserted into the patient's vasculature, and in some embodiments, this can be performed after the catheter 104 is inserted into the patient's vasculature. In some embodiments, the flow diverter 300 can be loaded into the lumen 502 of the catheter 104 after the catheter 104 has be advanced to a position proximate to the treatment location 2100. In some embodiments, the loading of the flow diverter 300 into the catheter 104 can be performed as discussed above with respect to FIG. 2.

Figure 25:
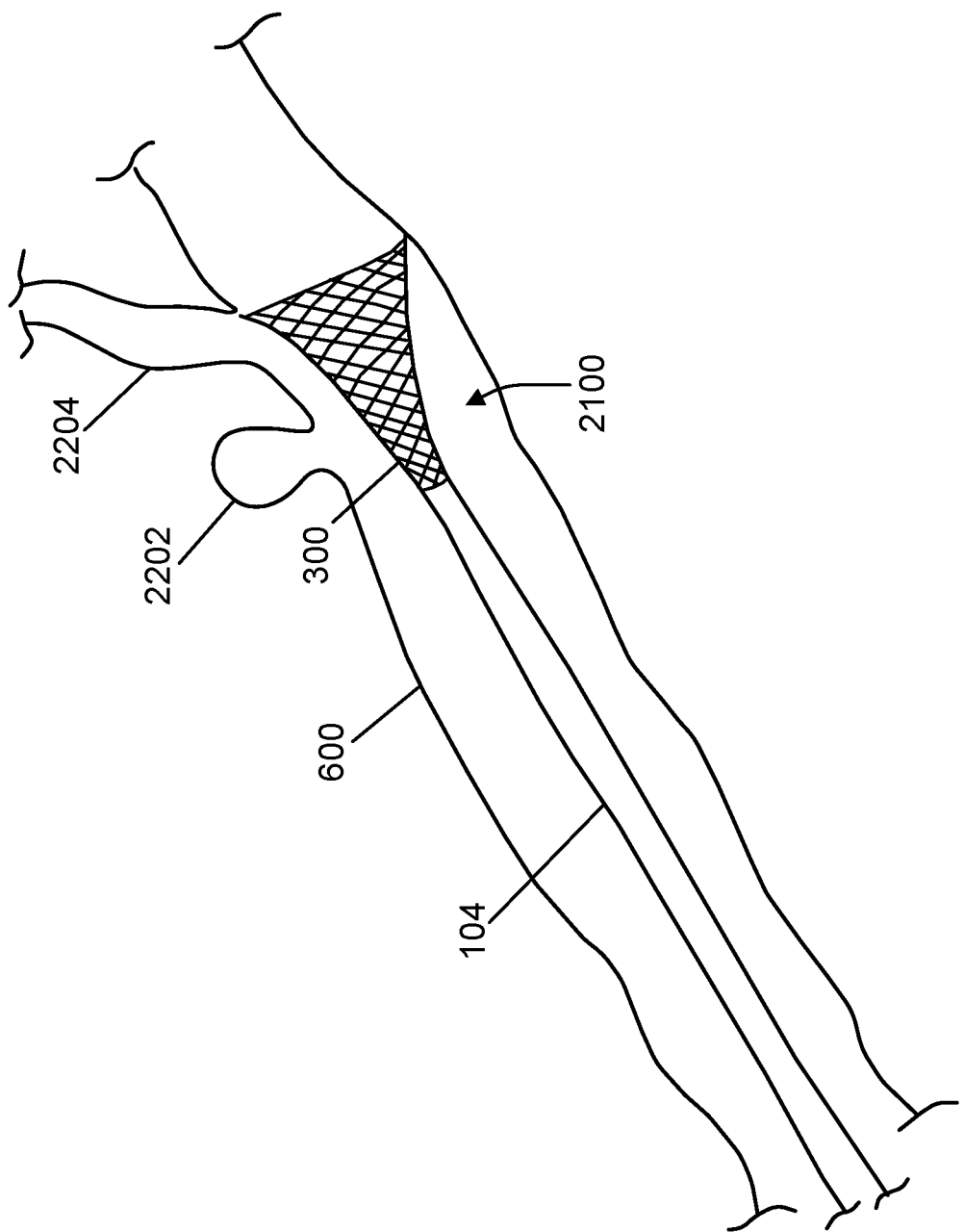
FIG. 25 is a depiction of a partially deployed flow diverter with the catheter at the first position with respect to the treatment site.

As shown in FIG. 25, the core wire 112 can be distally advanced in the catheter 104, thereby causing the flow diverter 300 to begin to deploy from the catheter 104. This can include advancing the core wire 112 through the catheter 104 to partially deploy the flow diverter 300 from the catheter 104. The core wire 112 can be coupled to the flow diverter 300 via one or several deployment features 118. In some embodiments, the distal advance of the core wire 112 with respect to the catheter 104 can likewise cause the flow diverter 300 to distally advance with respect to the catheter 104. In some embodiments, and as shown in FIG. 25, the flow diverter 300 expands and/or begins to expand as the flow diverter 300 exits the catheter 104.

The deployment of the flow diverter 300 can be monitored. In some embodiments, this monitoring can be to determine if the flow diverter 300 is properly positioned, to determine if the flow diverter 300 is expanded and/or expanding to a desired diameter, to determine if the flow diverter 300 is providing a desired length of coverage of the treatment site 2100, to determine if the flow diverter 300 has a desired size or diameter, or the like. In some embodiments, this can include monitoring the position of the flow diverter 300 itself via imaging, which flow diverter 300 can be at least partially radiopaque and/or include one or several radiopaque elements. In some embodiments, this can include monitoring the position of the catheter 104 and/or of the core wire 112 and/or one or several delivery features 118. This monitoring can include monitoring of the position of the flow diverter 300 within the blood vessel 600, and/or the monitoring of relative positions of one or several components and/or features described above with respect to each other.

In some embodiments, the position of the flow diverter 300 in the blood vessel 600 and/or the relative position of one or several components and/or features can be determined by monitoring a position, via imaging, of one or several: friction bumps 508, pushers 505, deployment coils 702, tubes 1002, compression coils 1010, claw mechanisms 1202, self-expanding elements 1902, tip coil 1018, support coil 510, and/or atraumatic tip 512. In some embodiments, the position of the core wire 112 and/or of one or several delivery features 118 can be monitored with respect to the position of the catheter 104 to determine whether the flow diverter 300 can be retracted into the catheter 104 to reposition the catheter 104 and/or the flow diverter 300 with respect to the treatment site 2100.

For example, in the embodiment shown in FIG. 25, the catheter 104 is advanced to far distally into the blood vessel 600 and the flow diverter 300, if deployed at its current location, would obstruct and/or partially obstruct the one or several structures to not be covered by the flow diverter 300, and would specifically obstruct and/or would partially obstruct the branch 2204 of the vessel 600. If it is determined that the flow diverter 300 is improperly positioned, and based on the position of the core wire 112 and/or of one or several delivery features 118 with respect to the position of the catheter 104, the flow diverter 300 can be retracted and/or partially retracted into the catheter 104 via the proximal retraction of the core wire 112. In some embodiments, the positioning of the catheter 104 with respect to the treatment location 2100 can be adjusted based at least in part on the imaging.

Further, if it is determined that the flow diverter 300 is the wrong size or that a different size flow diverter is desired 300, that the expansion of the flow diverter 300 can be improved, that the length of the flow diverter 300 in the treatment site 2100 can be improved, or the like, and based on the position of the flow diverter 300 with respect to the core wire 112 and/or of the one or several delivery features 118, then the flow diverter 300 can be retracted, either fully or partially, into the catheter 104.

Figure 26:
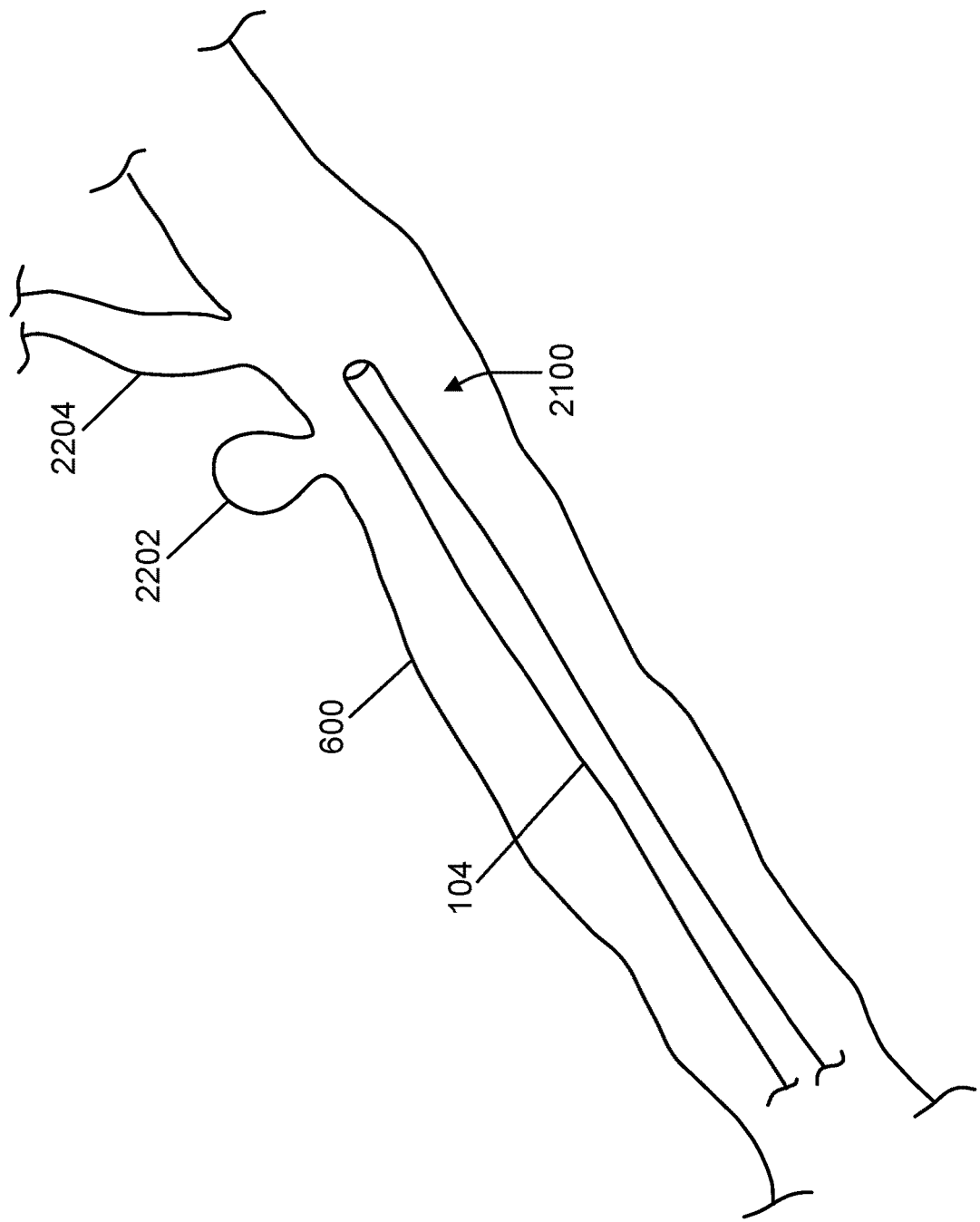
FIG. 26 is a depiction of the catheter at a second position with respect to the treatment site.

The catheter 104 can be repositioned with respect to the treatment area 2100 as shown in FIG. 26, and then the core wire 112 can be distally advanced in the catheter 104, thereby causing the flow diverter 300 to begin to deploy and/or to further deploy from the catheter 104. In some embodiments, and as shown in FIG. 26, the catheter 104 can be positioned distal, and in some embodiments, just distal of the treatment site 2100. In some embodiments, the distal advance of the core wire 112 with respect to the catheter 104 can likewise cause the flow diverter 300 to distally advance with respect to the catheter 104. In some embodiments, the flow diverter 300 can be deployed by advancing the core wire 112 with respect to the catheter 104. In some embodiments, this advancing of the core wire 112 with respect to the catheter 104 can include retracting the catheter 104 in the blood vessel 600 while maintaining the position of the core wire 112 with respect to the blood vessel 600, advancing the core wire 112 with respect to the blood vessel 600 while maintaining the position of the catheter 104 with respect to the blood vessel 600, or simultaneously retracting the catheter 104 with respect to the blood vessel 600 while advancing the core wire 112 with respect to the blood vessel 600.

Figure 27:
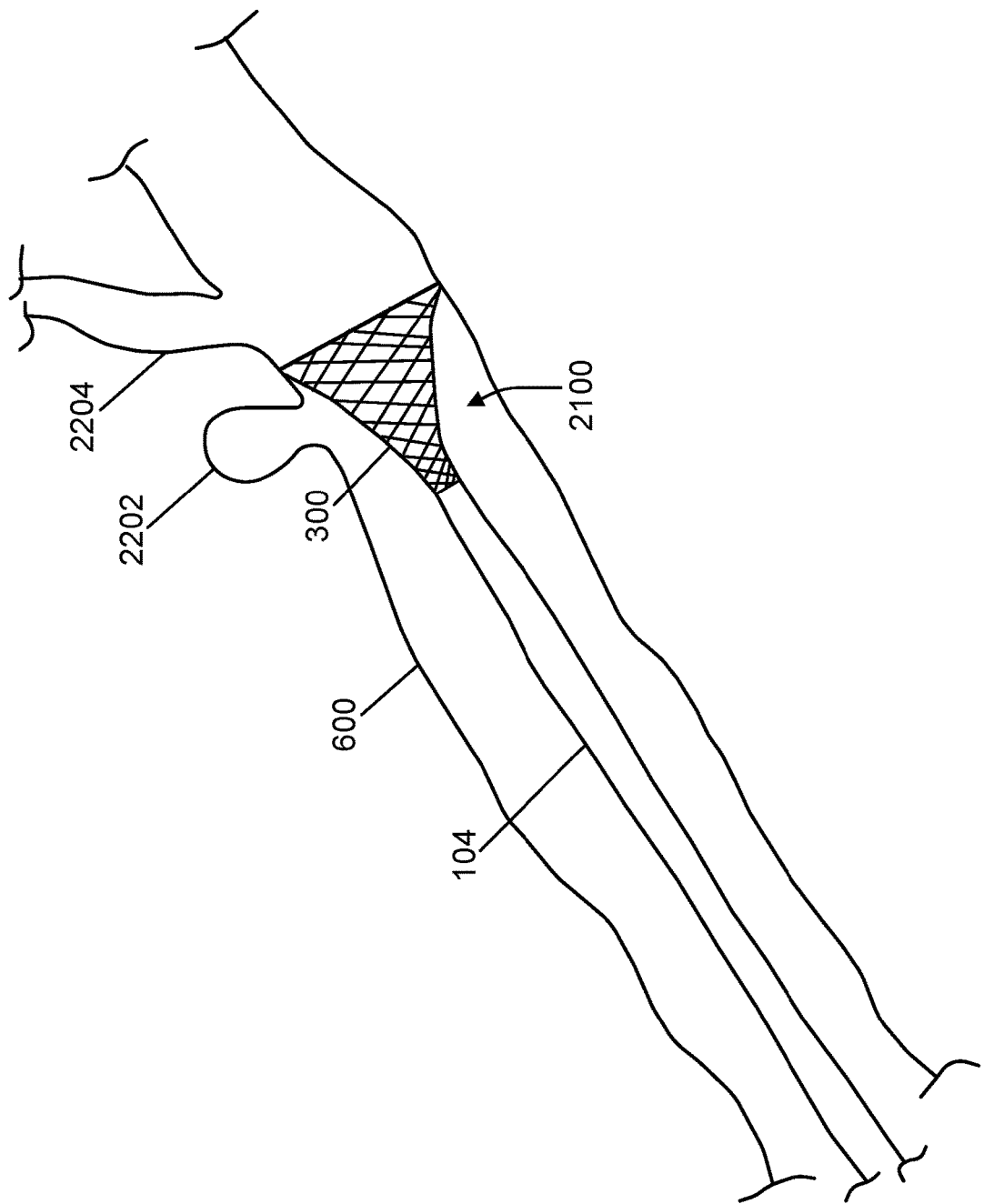
FIG. 27 is a depiction of a partially deployed flow diverter with the catheter at the second position with respect to the treatment site.
Figure 28:
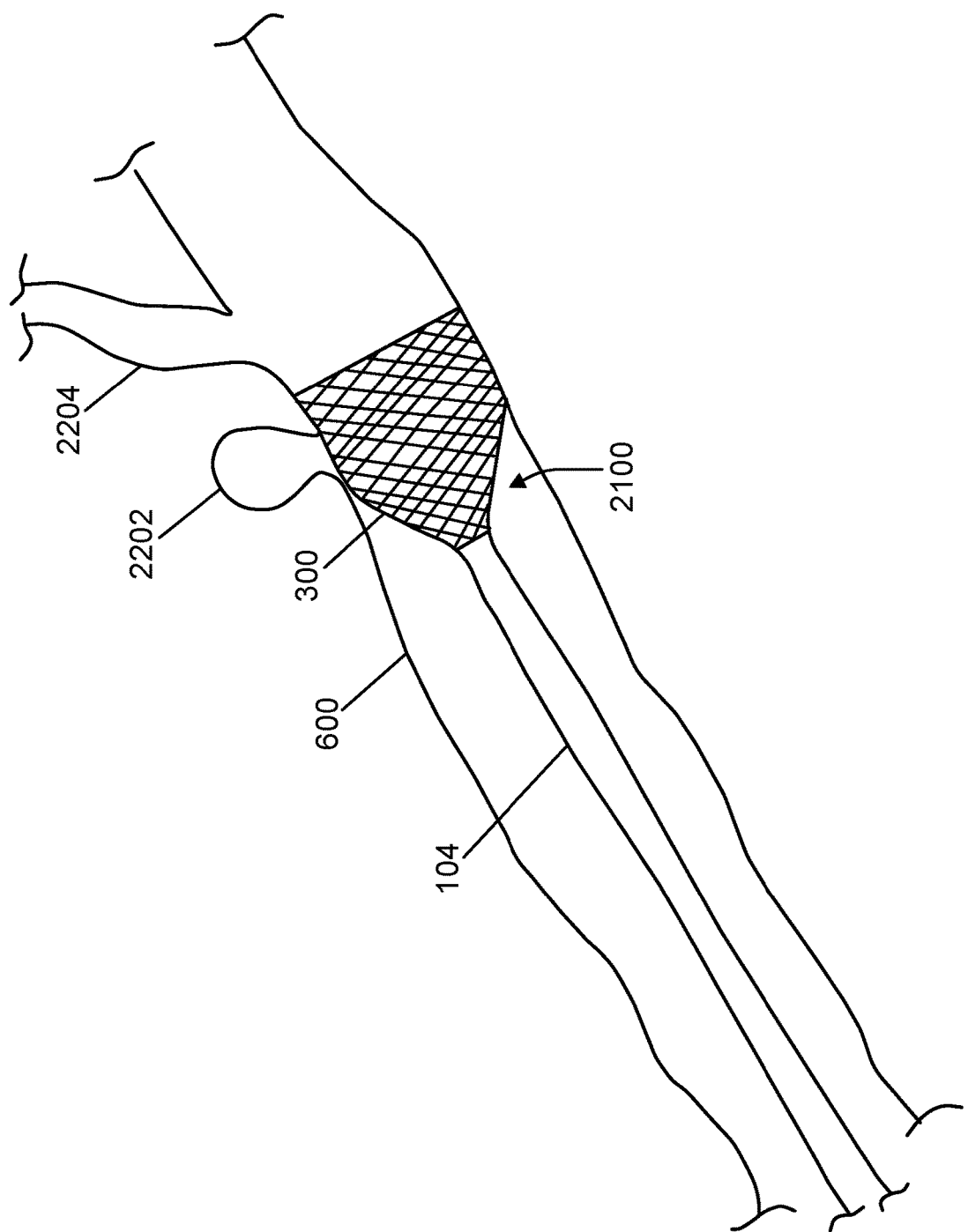
FIG. 28 is a depiction of a further partially deployed flow diverter with the catheter at the second position with respect to the treatment site.
Figure 29:
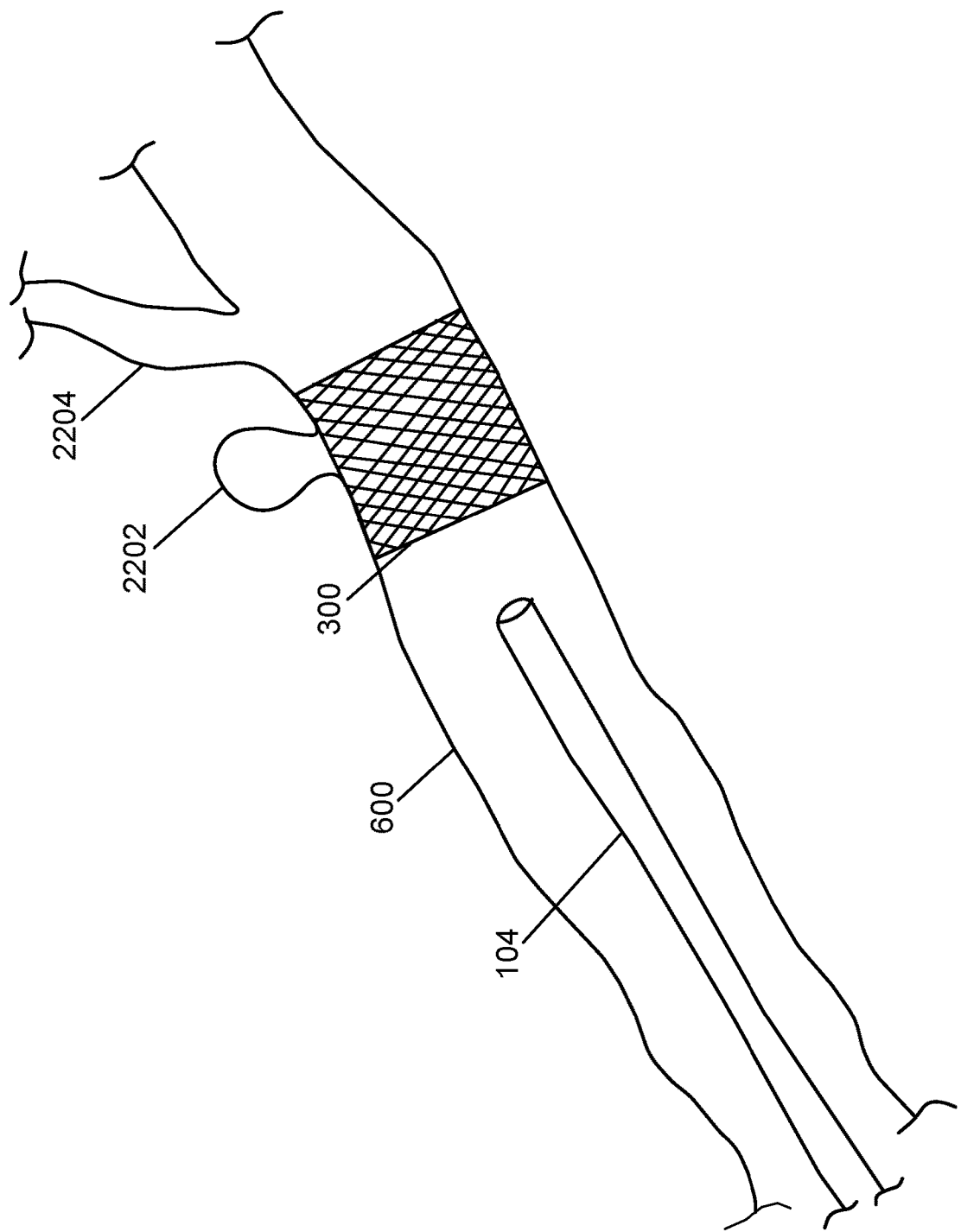
FIG. 29 is a depiction of a fully deployed flow diverter.

In some embodiments, and as shown in FIG. 27, the flow diverter 300 expands and/or begins to expand as the flow diverter 300 exits the catheter 104. The flow diverter 300 can continue to be deployed as shown in FIG. 28 via the further distal advance of the core wire 112 and thus of the flow diverter, and the flow diverter 300 can be fully deployed as shown in FIG. 29.

Figure 30:
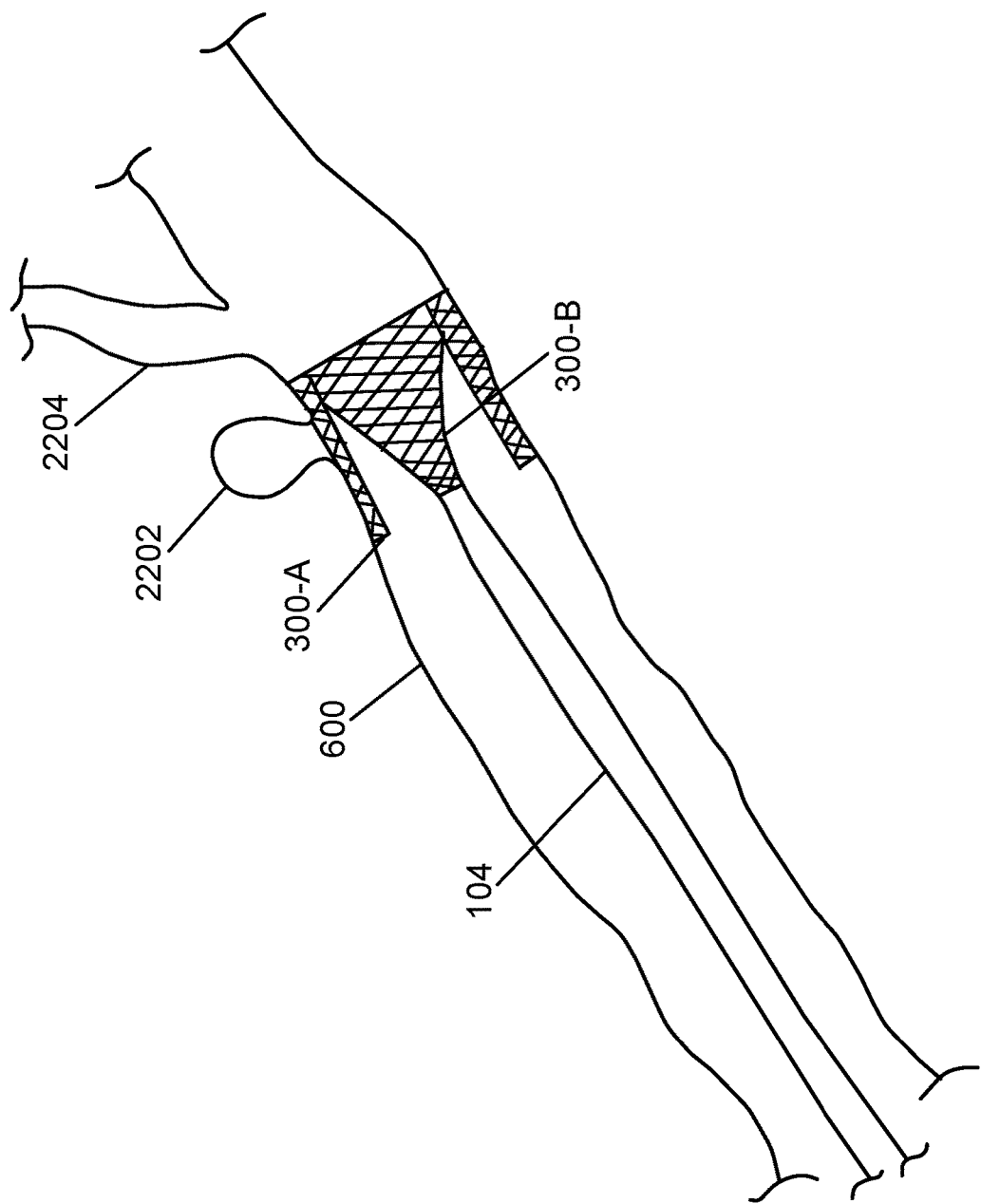
FIG. 30 is a depiction of deployment of an additional flow diverter on top of one or several previously deployed flow diverters.
Figure 31:
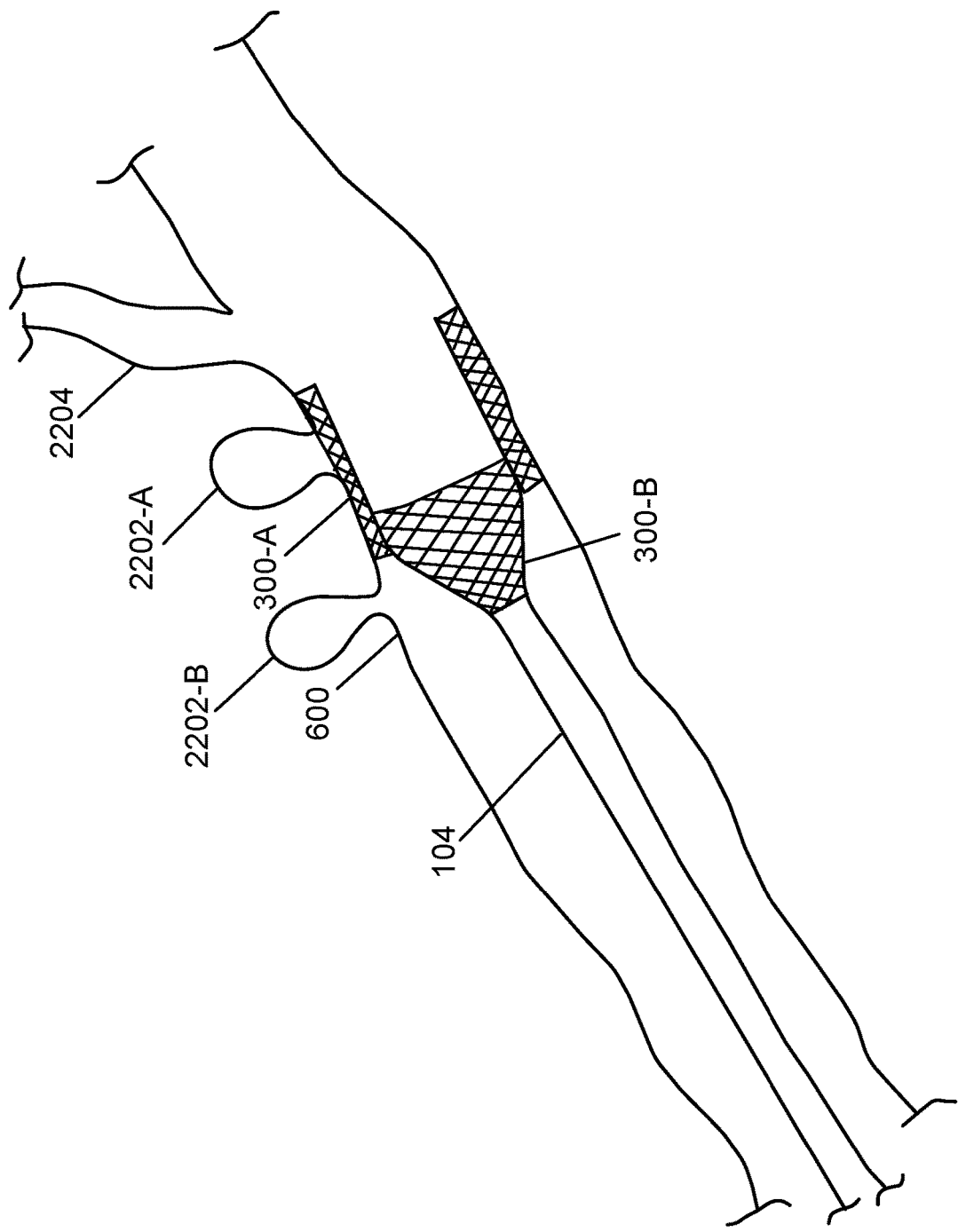
FIG. 31 is a depiction of deployment of an additional flow diverter partially overlapping with one of one or several previously deployed flow diverters.

After the flow diverter 300 has been fully deployed, the core wire 112 can be distally retracted into the catheter 104, and the catheter can be retracted from the treatment location 2100, and from the patient's vasculature. In some embodiments, one or several additional flow diverters 300 can be deployed to the treatment location 2100. This can include placing an additional flow diverter 300-B on top of one or several previously deployed flow diverters 300-A as shown in FIG. 30. Alternatively one or several additional flow diverters 300 can be placed to be partially overlapping to increase the length of treated blood vessel 600. In such an embodiment, and as shown in FIG. 31, a distal end of an additional flow diverter 300-B can be overlappingly placed over the proximal end or a previously placed flow diverter 300.

In the foregoing specification, the invention is described with reference to specific embodiments thereof, but those skilled in the art will recognize that the invention is not limited thereto. Various features and aspects of the above-described invention can be used individually or jointly. Further, the invention can be utilized in any number of environments and applications beyond those described herein without departing from the broader spirit and scope of the specification. The specification and drawings are, accordingly, to be regarded as illustrative rather than restrictive. It will be recognized that the terms "comprising," "including," and "having," as used herein, are specifically intended to be read as open-ended terms of art.

What is claimed is:

1. A system for delivering a flow diverter into a neurovascular blood vessel to treat an aneurysm, the system comprising:
    an elongate tubular member having a proximal end and a distal end, the tubular member comprising an interior wall defining a lumen;
    a core wire extending at least partially through the lumen of the tubular member, the core wire having a proximal end, a distal end, and a distal portion having a taper, the distal portion extending from an intermediate portion of the core wire to the distal end of the core wire;
    a self-expanding element comprising a first end coupled to the distal end of the core wire and extending distally to a second end, wherein the second end of the self-expanding element is located distal of the distal end of the core wire;
    a first friction bump located at one of the first end and the second end of the self-expanding element;
    a support coil extending along and around at least the distal end of the core wire; and
    a flow diverter comprising an expandable member defining a flow channel there through, the flow diverter positioned in the lumen of the tubular member and circumferentially between the wall of the tubular member and the self-expanding element in a constrained configuration, wherein the self-expanding element is disposed within the flow channel and is configured to move the flow diverter relative to the tubular member and into a neurovascular blood vessel while the self-expanding element is deployed out of the tubular member and to expand the flow diverter, and wherein the first friction bump is disposed within the flow channel of the flow diverter and is engaged with a portion of the flow diverter.

2. The system of claim 1, wherein the self-expanding element comprises a stent.

3. The system of claim 2, wherein the stent is laser cut.

4. The system of claim 1, wherein the flow diverter comprises a braided, expandable member.

5. The system of claim 4 wherein the flow diverter is self-expanding.

6. The system of claim 1, wherein the first friction bump comprises a radiopaque element.

7. The system of claim 6, wherein the radiopaque element comprises a coil of wire.

8. The system of claim 7, further comprising a second friction bump located at the other of the first end and the second end of the self-expanding element.

9. The system of claim 8, further comprising a flexible tip coil extending distally from the second end of the self-expanding element.

10. The system of claim 9, wherein the tip coil distally terminates with an atraumatic tip.

11. The system of claim 1, wherein the tubular member comprises an introducer sheath.

12. The system of claim 1, wherein the tubular member comprises a catheter.

13. A method for delivering a flow diverter into a neurovascular blood vessel to treat an aneurysm, the method comprising:
    advancing a microcatheter proximate to a treatment location within a neurovascular blood vessel;
    advancing a self-expanding element comprising a first end coupled to a distal end of a core wire through the microcatheter to deliver a flow diverter from the microcatheter into the neurovascular blood vessel, the flow diverter having a constrained configuration within the microcatheter and an unconstrained configuration outside of the microcatheter, wherein the flow diverter is configured to expand when in the unconstrained configuration, and wherein the self-expanding element extends distally beyond the distal end of the core wire from the first end to a second end;
    deploying the self-expanding element out of the microcatheter by advancing the self-expanding element via the core wire, the self-expanding element having a compressed state within the microcatheter and an expanded state outside of the microcatheter; and
    advancing the self-expanding element through the delivered flow diverter to expand the flow diverter, wherein the self-expanding element is in the expanded state when advanced through the delivered flow diverter to further expand the flow diverter.

14. The method of claim 13, wherein advancing the self-expanding element through the flow diverter to further expand the flow diverter comprises distally advancing the expanded self-expanding element through the flow diverter.

15. The method of claim 14, further comprising proximally retracting the self-expanding element through the flow diverter and into the microcatheter.

16. The method of claim 13, wherein the self-expanding element comprises a stent, and wherein the flow diverter comprises a tubular braided member.

17. The method of claim 16, wherein the self-expanding element comprises a first end coupled to the distal end of the core wire and distally extending to a second end.

18. The method of claim 17, wherein the self-expanding element comprises:
   a first friction bump located at the first end of the self-expanding element; and
   a second friction bump located at the second end of the self-expanding element.

19. The method of claim 18, wherein the microcatheter comprises an interior wall defining a lumen, wherein the flow diverter defines a diverter lumen, wherein the self-expanding element is at least partially in the diverter lumen, and wherein the flow diverter is positioned in the lumen of the microcatheter and circumferentially between the interior wall of the microcatheter and the self-expanding element.

20. The method of claim 13, further comprising:
   before deploying the self-expanding element out of the microcatheter, retracting the self-expanding element coupled to the distal end of the core wire to at least partially retract the flow diverter into the microcatheter; and
   before deploying the self-expanding element out of the microcatheter, adjusting positioning of the microcatheter with respect to the treatment location.

21. The method of claim 20, wherein at least the self-expanding element is radiopaque, the method further comprising imaging the radiopaque self-expanding element to determine a position of the flow diverter in the neurovascular blood vessel and a position of the self-expanding element with respect to the microcatheter, wherein the flow diverter is retracted into the microcatheter when the self-expanding element has not exited the microcatheter, and wherein the positioning of the microcatheter is adjusted with respect to the treatment location based on the imaging.

22. The method of claim 13, further comprising loading the flow diverter into the microcatheter.

23. The method of claim 22, wherein loading the flow diverter into the microcatheter comprises:
   inserting an introducer sheath containing the flow diverter through an access device into the microcatheter; and
   advancing the core wire through the introducer sheath to advance the flow diverter from the introducer sheath into the microcatheter.

24. The method of claim 13, wherein the self-expanding element intermittently contacts an inner wall of the flow diverter to thereby further expand the flow diverter when the self-expanding element is advanced through the delivered flow diverter.

25. The method of claim 13, wherein the self-expanding element intimately contacts an inner wall of the flow diverter to thereby further expand the flow diverter when the self-expanding element is advanced through the delivered flow diverter.

26. The method of claim 13, wherein the self-expanding element in the expanded state has a diameter less than a diameter of the flow diverter when the flow diverter is fully expanded in the unconstrained configuration.

27. The method of claim 13, wherein the delivered flow diverter extends across the aneurysm from a position proximal to the aneurysm to a position distal to the aneurysm.

* * * * *